US006541238B1

(12) United States Patent
Saxena et al.

(10) Patent No.: US 6,541,238 B1
(45) Date of Patent: Apr. 1, 2003

(54) RECOMBINANT CELLULOSE SYNTHASE

(75) Inventors: Inder Mohan Saxena, Austin, TX (US); Fong Chyr Lin, Austin, TX (US); R. Malcom Brown, Jr., Austin, TX (US)

(73) Assignee: Board of Regents, The University of Texas Systems, Austin, TX (US)

( * ) Notice: Subject to any disclaimer, the term of this patent is extended or adjusted under 35 U.S.C. 154(b) by 0 days.

(21) Appl. No.: 08/541,939

(22) Filed: Oct. 10, 1995

Related U.S. Application Data

(63) Continuation of application No. 08/222,322, filed on Apr. 4, 1994, now abandoned, which is a continuation of application No. 07/986,882, filed on Dec. 4, 1992, now abandoned, which is a continuation of application No. 07/494,093, filed on Mar. 15, 1990, now abandoned.

(51) Int. Cl.$^7$ .............................. C12N 1/20; C12N 9/10; C12N 9/12; C12N 15/00
(52) U.S. Cl. ................... 435/252.3; 435/193; 435/194; 435/252.33; 435/257.2; 435/240.2; 435/240.1; 435/240.4; 435/320.1
(58) Field of Search ................................ 435/193, 194, 435/252.3, 320.1, 257.2, 240.1, 240.2, 240.4, 252.33; 536/23.2

(56) References Cited

U.S. PATENT DOCUMENTS

| 4,788,135 A | 11/1988 | Davis et al. .................... 435/6 |
| 5,268,274 A | * 12/1993 | Ben-Bassat et al. ....... 435/69.1 |

FOREIGN PATENT DOCUMENTS

| EP | 0228779 | 10/1985 |
| EP | 0260093 | * 3/1988 |
| WO | WO90/12098 | 10/1990 |

OTHER PUBLICATIONS

Lin et al. "Symposium on the Biogenesis of Cellulose, the Tenth Cellulose Conference" May 29–Jun. 2, 1988, p. 27.*
Bureau et al. PNAS vol. 84, Oct. 1987, pp. 6985–6989.*
Thelen et al. Chemical Abstracts 105:295, #1485609, 1986.*
Li et al., *Plant Physiol.* (1993) 101:1149–1156, "β–Glucan Synthesis in the Cotton Fiber".
Saxena et al., *Plant Molecular Biology*(1991) 16:947–954, "Identification of a new gene in an operon for cellulose biosynthesis in *Acetobacter xylinum*".
Okuda et al., *Plant Physiol.* (1993) 101:1131–1142, "β–Glucan Synthesis in the Cotton Fiber".
Li et al., *Plant Physiol.* (1993) 101:1143–1148, "β–Glucan Synthesis".
Fong Chyr Lin, *Cellulose and Wood Chemistry Technology*, Schuerch, C., Ed. Wiley, New York (1989) pp. 473–492.
Brown et al., *Cellulose and Wood Chemistry Technology*, Schuerch, C., Ed. Wiley, New York (1989) pp. 639–657.
Saxena et al., *Cellulose and Wood Chemistry Technology*, Schuerch, C., Ed. Wiley, New York (1989) pp. 537–557.
Roberts et al., *Cellulose and Wood Chemistry Technology*, Schuerch, C., Ed. Wiley, New York (1989) pp. 689–704.
Benziman et al., *Proc. Natl. Acad. Sci., U.S.A.*, 77:6678–6682 (1980) *Cellulose biogenesis: Polymerization and crystallization are coupled processes in Acetobacter xylinum.*
Aloni et al., *Proc. Natl. Acad. Sci., U.S.A.*, 79:6448–6452 (1982) *Achievement of high rates of in vitro synthesis of 1,4–β–D–glucan: Activation by cooperative interaction of the Acetobacter xylinum enzyme system with GTP, polyethylene glycol, and a protein factor.*
Ross et al., *Nature*, 325:279–281 (1987) *Regulation of cellulose synthesis in Acetobacter xylinum by cyclic diguanylic acid.*
Valla et al., *Mol. Gen. Genet.*, (1989) 217:26–30 *Cloning of a gene involved in cellulose biosynthesis in Acetobacter xylinum: Complementation of cellulose–negative mutants by the UDPG pyrophosphorylase structural gene.*
Sutherland, I.W., *Biosynthesis of Microbial Exopolysaccharides*, 1982.
Hayashi, T., *Annu. Rev. Plant Physiol. Plant Mol. Biol.* (1989) 40:139–68 *Xyloglucans in the Primary Cell Wall.*
Fong Chyr Lin et al., *The Journal of Biolkogical Chemistry*(1990) 265:4782–4784 *Identification of the Uridine 5'–Diphosphoglucose (UDP–Glc) Binding Subunit of Cellulose Synthase in Acetobacter xylinum Using the Photoaffinity Probe 5–Azido–UDP–Glc.*
Fong Chyr Lin et al., *Science*, 230:822–825 *Synthesis of Fibrils in Vitro by a Solubilized Cellulose Synthase from Acetobacter xylinum.*
Drake et al., *The Journal of Biological Chemistry*(1989) 264:11928–11933 *Synthesis and Properties of 5–Azido–UDP–Glucose—Development of Photoaffinity Probes for Nucleotide Diphosphate Sugar Binding Sites.*
Saxena et al., *Plant Molecular Biology*, (1990) 15:673–683 *Cloning and sequencing of the cellulose synthase catalytic subunit gene of Acetobacter xylinum.*
Wong et al., *Proc. Natl. Acad. Sci., U.S.A.*(1990) 87:8130–8134 *Genetic organization of the cellulose synthase operon in Acetobacter xylinum.*

(List continued on next page.)

Primary Examiner—Ponnathapu Achutamurthy
Assistant Examiner—Manjunath N. Rao
(74) Attorney, Agent, or Firm—Fulbright & Jaworski

(57) ABSTRACT

The present invention relates to the compositions and methods associated with the cloning of the catalytic subunit of cellulose synthase responsible for catalyzing cellulose biosynthesis. The invention relates further to compositions and methods for obtaining host cells containing recombinant cellulose synthase as well as compositions and methods for obtaining cellulose synthase from natural sources. In certain aspects, the present invention provides methods for the cloning of an 83 kd subunit of the cellulose synthase enzyme from *Acetobacter xylinum*.

31 Claims, 15 Drawing Sheets

OTHER PUBLICATIONS

Frost et al, *The Journal of Biological Chemistry* (1990) 265:2162–2167 *Identification of the UDP–glucose–binding Polypeptide of Callose Synthase from Beta vulgaris L. by Photoaffinity Labeling with 5–Azido–UDP–glucose.*

Suggs et al., *Proc. Natl. Acad. Sci., U.S.A.*, 78:6613–6617 *Use of Synthetic Oligonucleotides as Hybridization probes: Isolation of cloned cDNA sequences for human $\beta_2$–microglobulin*, 1981.

Thelan et al., *Plant Physiology*, (1986) 81:913–918 *Gel–electrophoretic Separation, Detection, and Characterization of Plant and Bacterial UDP–glucose glucosyl Transferase.*

Aloni et al., *The Journal of Biological Chemistry*, (1983) 258:4419–4423 *Solubilization of the UDP–glucose: 1,4–$\beta$–D–glucan 4–$\beta$–D–glucosyltransferase (Cellulose Synthase) from Acetobacter xylinum.*

Coucheron, D. H., *Journal of Bacteriology*, (1991) 173:5723–5731 *An Acetobacter xylinum Insertion Sequence Element Associated with Inactivation of Cellulose Production.*

*ChemicalWeek*, (1990) p. 7.

Mayer et al., *Cell Walls* (1989) Abstract No. 38, *The Polypeptide Substructure of Bacterial Cellulose Synthase and Its Occurrence in Higher Plants.*

Saxena et al., ASM Annual Meeting (1990) *Cloning and Sequencing of the Cellulose Synthase Catalytic Subunit Gene of Acetobacter xylinum.*

Dunsmuir et al., *Plant Biotechnology Bottlenecks for Commercialization and Beyond*Ed. T. J. Mabry (1987).

Gasser et al., *Genetically Engineering Plants for Crop Improvement.*

Atalla, *Proceedings of the Seventh Annual Symposium in Botany*(1984) pp. 381–391 *Polymorphy in Native Cellulose: Recent Developments.*

Hall et al., *Proc. Royal Soc. B.*, 151:497 (1960) *Oriented Cellulose as a Component of Mammalian Tissue.*

Translation of Article appearing in May 15, 1987 issue of *The Japan Industrial Journal.*

Dillingham et al., *Cellulose and Cellulose–Free Cell Production by Acetobacter xylinum,* 1961.

Wasserman et al., *Identification of the UDPG–Binding Polypeptide of (1,3) –$\beta$–D–glucan Synthase of Higher Plants by Photoaffinity Labeling with 5–Azido–UDPG,* 1990.

Umbeck et al., *Bio/Technology 5:263–266 Genetically Transformed Cotton (Gossypium Hirsutum L.) Plants,* 1987.

Potter & Haley, *Methods in Enzymology*, 91:613–633 *Photoaffinity Labelling of Nucleotide Binding Sites,* 1983.

Thomashow et al., *Journal of Bacteriology* (1987) 169:3209–3216 *Identification of a New Virulence Locus in Agrobacterium tumefaciens that Affects Polysaccharide Composition and Plant Cell Attachment.*

Harding et al., *Journal of Bacteriology* (1987) 169:2854–2861 *Genetic and Physical Analyses of a Cluster of Genes Essential for Xanthan Gum Biosynthesis in Xanthomonas campestris.*

Easson et al., *Journal of Bacteriology* (1987) 169:4518–4524 *Isolation of Zoogloea ramigera I–16–M Exopolysaccharide Biosynthetic Genes and Evidence for Instability within this Region.*

Kang et al., *The Journal of Biological Chemistry*, 259:14966–14972 *Isolation of Chitin Synthetase from Saccharomyces cerevisiae,* 1984.

Delmer, *Ann. Rev. Plant Physiol.* (1987) 38:259–90 *Cellulose Biosynthesis.*

Lawson et al., *Plant Physiol.* (1989) pp. 101–108 *UDP–Glucose:–$\beta$–D–glucan Synthase from Daucus carota L.*

* cited by examiner

```
   1   CGCTTCCCGC ACATCAGCAT CGTCCATAAG TGAGCGTCCG GTGACAGGGT
  51   GTTGCCGATG AATGGAGTCC TGTTCCGAAG CACGCCTCAG CCGCGGGACG
 101   TCCGCGTCCC GGCGATCTGA GCTTTTTCTT TCAGGGGATG CGCGACACCC
 151   GTGATGAAAA GAAGTTCTTT CCCGTGGCGT CCACGCGATC AGTTCGTTCT
 201   AATGTTTCCA GGATGACCAG CATGACCAAG ACAGACACGA ATTCCTCTCA
 251   GGCTTCTCGT CCCGGCAGCC CCGTCGCCTC GCCTGATGGG TCGCCCACAA
 301   TGGCCGAAGT GTTCATGACG CTGGGTGGTC GTGCGACGGA ACTCCTCAGC
 351   CCCCGTCCTT CGCTGCGGGA GGCGCTGTTG CGTCGTCGTG AAAACGAAGA
 401   AGAATCCTAA GGCCCTATAT TCAGGCGACC GCCTGTCCCT GTGTCCTGCC
 451   TGGTGAAATG GCGGGGGCAG GGGCAGACAC GCTGCACTGG CTCGGCGATC
 501   TATTCCGTCT TTGGCCTGGG TGATGTTTCC GCAGCCCAGG CGGCCCGCTT
 551   TGCCCCGATG TGACCGCAGA TGGTCGGGGT CAGGTTTTTT TTGACGTAAT
 601   TTTTCTGTTT TACAGCATTT CGGACGAGTT GTTTATGCCA GAGGTTCGGT
   1                                             M  P  E  V  R
 651   CGTCAACGCA GTCAGAGTCA GGAATGTCAC AGTGGATGGG GAAAATTCTT
        S  S  T  Q  S  E  S  G  M  S  Q  W  M  G  K  I  L
 701   TCCATTCGCG GTGCTGGGCT GACTATTGGT GTTTTTGGCC TGTGTGCGCT
        S  I  R  G  A  G  L  T  I  G  V  F  G  L  C  A  L
 751   GATTGCGGCT ACGTCCGTGA CCCTGCCGCC AGAACAGCAG TTGATTGTGG
        I  A  A  T  S  V  T  L  P  P  E  Q  Q  L  I  V
 801   CATTTGTATG TGTCGTGATC TTTTTTATTG TCGGTCATAA GCCCAGCCGT
        A  F  V  C  V  V  I  F  F  I  V  G  H  K  P  S  R
 851   CGGTCCCAGA TTTTCCTTGA AGTGCTGTCA GGGCTGGTTT CGCTGCGCTA
        R  S  Q  I  F  L  E  V  L  S  G  L  V  S  L  R  Y
 901   TCTGACATGG CGCCTGACGG AAACGCTTTC ATTCGATACA TGGTTGCAGG
        L  T  W  R  L  T  E  T  L  S  F  D  T  W  L  Q
 951   GTCTGCTTGG GACAATGCTT CTGGTGGCGG AACTTTACGC CCTGATGATG
        G  L  L  G  T  M  L  L  V  A  E  L  Y  A  L  M  M
1001   CTGTTCCTCA GCTATTTCCA GACGATCGCG CCATTGCATC GTGCGCCTCT
        L  F  L  S  Y  F  Q  T  I  A  P  L  H  R  A  P  L
```

FIG.1A

```
1051  GCCGCTGCCG CCGAACCCTG ACGAATGGCC CACGGTCGAT ATCTTCGTCC
       P  L  P   P  N  P   D  E  W  P   T  V  D   I  F  V

1101  CGACCTACAA CGAAGAACTG AGCATTGTCC CGCTGACGGT GCTGGGATCA
       P  T  Y  N  E  E  L   S  I  V   P  L  T  V   L  G  S

1151  CTGGGGATTG ACTGGCCACC GGAAAAGGTG CGGGTTCATA TCCTTGATGA
       L  G  I   D  W  P  P   E  K  V   R  V  H   I  L  D  D

1201  CGGTCGTCGT CCTGAATTCG CCGCCTTTGC CGCTGAATGT GGCGCGAATT
       G  R  R   P  E  F   A  A  F  A   A  E  C   G  A  N

1251  ATATCGCCCG CCCGACGAAC GAACATGCAA AGGCCGGTAA TCTTAACTAT
       Y  I  A  R   P  T  N   E  H  A   K  A  G  N   L  N  Y

1301  GCCATTGGTC ATACCGATGG TGATTACATC CTGATCTTTG ACTGCGACCA
       A  I  G   H  T  D  G   D  Y  I   L  I  F   D  C  D  H

1351  CGTCCCGACC CGCGCCTTCC TGCAGTTGAC AATGGGCTGG ATGGTCGAAG
       V  P  T   R  A  F   L  Q  L  T   M  G  W   M  V  E

1401  ACCCGAAGAT CGCGCTGATG CAGACCCCGC ATCACTTCTA TTCCCCCGAC
       D  P  K  I   A  L  M   Q  T  P   H  H  F   Y  S  P  D

1451  CCGTTCCAGC GGAACCTGTC GGCTGGTTAT CGCACCCCGC CGAAGGCAA
       P  F  Q   R  N  L  S   A  G  Y   R  T  P   P  E  G  N

1501  CCTGTTTTAT GGCGTGGTGC AGGATGGCAA CGATTTCTGG GATGCGACCT
       L  F  Y   G  V  V   Q  D  G  N   D  F  W   D  A  T

1551  TCTTTTGCGG GTCATGTGCA ATCCTGCGTC GCACGGCGAT TGAGCAGATC
       F  F  C  G   S  C  A   I  L  R   R  T  A  I   E  Q  I

1601  GGCGGCTTTG CGACCCAGAC CGTGACCGAA GACGCGCATA CCGCACTCAA
       G  G  F   A  T  Q  T   V  T  E   D  A  H   T  A  L  K

1651  GATGCAGCGT CTGGGCTGGT CCACGGCCTA TCTGCGTATC CCGCTTGCCG
       M  Q  R   L  G  W   S  T  A  Y   L  R  I   P  L  A

1701  GTGGTCTCGC GACGGAACGC CTGATCCTGC ATATCGGACA GCGCGTGCGC
       G  G  L  A   T  E  R   L  I  L   H  I  G  Q   R  V  R

1751  TGGGCGCGTG GGATGCTGCA GATCTTCCGC ATCGACAATC CTCTGTTCGG
       W  A  R   G  M  L  Q   I  F  R   I  D  N   P  L  F  G

1801  GCGTGGCCTG TCATGGGGGC AGCGGCTTTG TTACCTGTCG GCCATGACGT
       R  G  L   S  W  G   Q  R  L  C   Y  L  S   A  M  T
```

FIG. 1B

```
1851  CGTTCCTGTT CGCTGTCCCG CGCGTCATCT TCCTGAGCTC CCCGCTGGCG
       S  F  L  F  A  V  P  R  V  I  F  L  S  S  P  L  A

1901  TTCCTGTTCT TTGGGCAGAA CATCATTGCC GCGTCGCCGC TCGCGCTGCT
       F  L  F  F  G  Q  N  I  I  A  A  S  P  L  A  L  L

1951  GGCCTATGCC ATCCCGCACA TGTTCCACGC CGTCGGCACG GCGTCGAAGA
       A  Y  A  I  P  H  M  F  H  A  V  G  T  A  S  K

2001  TCAACAAGGG CTGGCGCTAC TCCTTCTGGA GTGAGGTCTA TGAAACCACG
       I  N  K  G  W  R  Y  S  F  W  S  E  V  Y  E  T  T

2051  ATGGCGCTGT TCCTGGTGCG CGTGACGATT GTCACCCTGC TCAGCCCTTC
       M  A  L  F  L  V  R  V  T  I  V  T  L  L  S  P  S

2101  ACGTGGGAAG TTCAACGTGA CGGACAAGGG CGGGTTGCTT GAAAAAGGTT
       R  G  K  F  N  V  T  D  K  G  G  L  L  E  K  G

2151  ATTTCGACCT TGGCGCTGTC TACCCGAACA TCATCCTTGG CCTGATCATG
       Y  F  D  L  G  A  V  Y  P  N  I  I  L  G  L  I  M

2201  TTCGGCGGCC TGGCGCGTGG TGTCTATGAA CTGTCTTTCG GCCATCTCGA
       F  G  G  L  A  R  G  V  Y  E  L  S  F  G  H  L  D

2251  CCAGATCGCC GAACGTGCCT ACCTGCTGAA CTCCGCCTGG GCAATGCTCA
       Q  I  A  E  R  A  Y  L  L  N  S  A  W  A  M  L

2301  GCCTCATCAT CATCTTGCGC CATGCCGTGG GGCGTGAAAC ACAGCAGAAA
       S  L  I  I  I  L  R  H  A  V  G  R  E  T  Q  Q  K

2351  CGCAACAGTC ATCGCATCCC CGCAACCATC CCGGTGGAAG TGGCGAATGC
       R  N  S  H  R  I  P  A  T  I  P  V  E  V  A  N  A

2401  CGATGGGTCC ATCATCGTGA CGGGCGTGAC CGAGGACCTG TCCATGGGTG
       D  G  S  I  I  V  T  G  V  T  E  D  L  S  M  G

2451  GGGCCGCGGT GAAGATGTCA TGGCCTGCGA AGCTGTCGGG GCCGACGCCG
       G  A  A  V  K  M  S  W  P  A  K  L  S  G  P  T  P

2501  GTTTATATCC GTACTGTCCT TGACGGGGAG GAACTGATCC TTCCCGCCAG
       V  Y  I  R  T  V  L  D  G  E  E  L  I  L  P  A  R

2551  GATCATCCGT GCTGGCAACG GACGGGGGAT TTTCATCTGG ACGATTGATA
       I  I  R  A  G  N  G  R  G  I  F  I  W  T  I  D

2601  ACCTGCAGCA GGAATTCTCG GTTATCCGTC TGGTGTTCGG CCGTGCCGAC
       N  L  Q  Q  E  F  S  V  I  R  L  V  F  G  R  A  D
```

FIG.1C

```
2651   GCATGGGTTG ACTTGGGGCA ATTACAAGGC CGACCGCCCG CTGCTCAGCC
        A  W  V    D  L  G  Q   L  Q  G   R  P  P    A  A  Q  P

2701   TCATGGACAT GGTTCTCAGC GTCAAGGGCC TGTTCCGTTC AAGTGGCGAT
        H  G  H    G  S  Q    R  Q  G  P  V  P  F    K  W  R

2751   ATCGTCCATC GCAGTTCCCC AACCAAGCCT TTGGCTGGCA ATGCCCTGTC
 722    Y  R  P  S  Q  F  P    N  Q  A    F  G  W  Q   C  P  V

2801   TGACGATACG AACAACCCGT CACGCAAGGA GCGTGTGCTG AAGGGAACCG
       STOP

2851   TGAAAATGGT TTCGCTTCTG GCGCTGCTGA CATTTGCTTC CTCGGCACAG

2901   GCGGCGTC
```

FIG.1D

RECOMBINANT CELLULOSE SYNTHASE

This is a continuation of co-pending application Ser. No. 08/222,322, filed Apr. 4, 1994, which is a continuation of application Ser. No. 07/986,882, filed Dec. 4, 1992 which is a continuation of application Ser. No. 07,494,093, filed Mar. 15, 1990, each abandoned.

The National Science Foundation provided funding used in part for this invention under grant number 9-397 and the National Aeronautic and Space Administration provided funding used in part for this invention under grant number DCB-8903685. Accordingly, the Federal Government may have certain rights in this invention pursuant to 35 U.S.C. 202.

BACKGROUND OF THE INVENTION

1. Field of the Invention

This invention relates generally to compositions of and methods for obtaining cellulose synthase. The invention relates as well to the DNA sequences encoding cellulose synthase, the recombinant vectors carrying those sequences, the recombinant host cells including either the sequences or vectors and recombinant cellulose synthase polypeptides. More specifically, the invention relates to the cloning and expression of cellulose synthase from *Acetobacter xylinum*.

2. Description of the Related Art

Cellulose biosynthesis is an event largely associated with plant cells, especially certain agronomic species such as cotton where as much as 90–95% of the secondary wall of mature cotton fibers is composed of cellulose. However, studies of cellulose biosynthesis in higher plants have been very frustrating, mainly because cellulose synthase, due to its lability, has evaded isolation and purification. Furthermore, the study of this enzyme has been hampered by the great difficulty in detecting formation of cellulose in vitro using purified preparations of plant and other eukaryotic cells [Delmer 1987: In higher plant preparations, the β-1,3-glucan (callose) chains are synthesized instead of the β-1,4-glucan of cellulose].

Apart from the higher plants, a large number of bacteria synthesize cellulose, including *Acetobacter xylinum* (*A. xylinum*), which converts as much as 35% of the glucose supplied to cultures of this bacterium into cellulose. Unlike the situation in plants and other eukaryotic cells noted above, the cellulose synthase of this bacterium has been isolated to a certain degree. Because of these facts, coupled with the capacity of the bacterium to synthesize a highly purified form of cellulose in vitro using membrane preparations, *A. xylinum* has become a preferred system for studies on the synthesis and organization of cellulose [Delmer 1987: In the bacterium, β-1,4-glucan (cellulose) chains can be detected].

The biosynthesis of cellulose in *A. xylinum* is visualized as a two-step process. The first step involves the polymerization of sugar nucleotides (UDP-glucose; UDP-glc) into a β-1,4,-linked glucan chain. The polymerization reaction is catalyzed by the enzyme cellulose synthase (UDP-glucose:1,4-β-D-glucosyltransferase; E.C. 2.4.1.12) which is present in the cytoplasmic membrane (Bureau and Brown 1987). The activity of this enzyme is regulated by bis-(3', 5')-cyclic diguanylic acid (Ross 1987).

Purification of the cellulose synthase activity from membrane preparations has been accomplished by an entrapment procedure (Lin and Brown 1989) similar in some aspects to one used in the purification of chitin synthase from yeast (Kang 1984). The molecular weight of the native enzyme in Triton X-100 solubilized preparations appears to be 490 kd as determined by gel filtration (Lin and Brown 1989). Electron microscopy of the purified preparation shows doughnut-shaped particles indicating that the cellulose synthase may be organized as a tetramer or octamer (Lin and Brown 1989). Lithium dodecyl sulfate polyacrylamide gel electrophoresis of the purified preparation shows two major bands with molecular weights of 93 kd and 83 kd. The resistance of the cellulose synthase activity and of the 83 kd polypeptide to trypsin treatment has suggested that the 83 kd polypeptide is the active cellulose synthase (Lin and Brown 1989).

Photoaffinity probes have been used with glucan synthases to identify these enzymes in a variety of different species. In red beets, a 57 kd polypeptide has been shown to be the substrate-binding component of (1,3)-β-glucan synthase (Wasserman 1989). In cotton fibers and in mung bean, a 50 kd polypeptide appears to bind the substrate (Delmer and Solomon 1989). In *A. xylinum*, Mayer et al. (1989) suggested a 67 k polypeptide as the substrate-binding subunit and a 57 kd polypeptide as the activator-binding subunit of a 420 kd oligomeric cellulose synthase. These investigators suggested the presence of similarly sized peptides in other cellulose-producing organisms such as *Agrobacterium tumefaciens*, mung bean, wheat, pea and cotton on the basis of immunochemical analyses.

Genes involved in the synthesis of other exopolysaccharides in a number of bacteria have been cloned using the standard approach of genetic complementation [Easson (1987); Harding (1987); Calvin and Hanawalt (1988)]. Mutants of *A. xylinum* defective in the production of cellulose, yet which still possess a normal complement of cellulose synthase have been identified in particular strains. Certain of these mutants have been shown to be deficient in the activity of UDPG-pyrophosphorylase, the enzyme required for the synthesis of the cellulose synthase substrate molecule, UDP-glucose. Complementation of these mutants by cloned fragments from *A. xylinum*-derived DNA has led to the isolation of the gene encoding UDPG-pyrophosphorylase (Valla 1989).

Surprisingly, however, no mutants actually deficient in cellulose synthase activity have been identified. This is despite the fact that there have been a large number of mutants identified which morphologically appear to be cellulose-deficient, but which synthesize small amounts of an altered crystalline polymorph of cellulose (cellulose II) and have the wild type level of cellulose synthase activity when assayed in vitro for cellulose synthesis [Saxena and Brown (1989); Roberts et al. (1989)].

Thus, it has been considerably difficult to apply the standard approaches of classical genetics or even the powerful techniques of molecular biology to the study of cellulose biosynthesis. Lacking purified quantities of the enzyme, lacking detailed information of the subunit architecture, lacking means to specifically identify the substrate-binding subunit, and lacking a simple genetic method of isolating mutants deficient in cellulose synthase activity, have each hampered the ability of researchers to isolate DNA segments encoding cellulose synthase.

SUMMARY OF THE INVENTION

The present invention for the first time, provides the vectors, DNA segments, purified protein, antibodies, methods of cloning, and recombinant host cells, seeds and plants necessary to obtain and use a recombinant cellulose synthase. Thus, the difficulties encountered with applying the standard approaches of classical genetics or techniques of molecular biology to the study of cellulose biosynthesis have been overcome. Accordingly, the present invention concerns generally compositions and methods for the preparation of recombinant cellulose synthase of both prokaryotic and eukaryotic origin.

In certain general and overall embodiments, the invention concerns recombinant vectors and isolated DNA segments encoding a cellulose synthase peptide. The DNA segments of the invention may encode biologically functional equivalent protein or peptides which have variant amino acid sequences, such as with changes selected based on considerations such as the relative hydropathic score of the amino acids being exchanged.

In the context of the present invention, the term cellulose synthase is intended to refer to peptides or proteins having the biological and the immunological identity of the cellulose synthase of the cell enabled lines by the present invention. For example, such cell lines would include cells of *Acetobacter xylinum*. Generally, the cellulose synthase of the invention will refer to a 723 amino acid peptide or protein (SEQ ID NO:2) in that this is the precise length of the only presently sequenced cellulose synthase. However, the invention does not preclude and, in fact enables, preparation or use of shorter or longer peptides or proteins, so long as a peptide or protein has similar in kind biological activity and/or a cross reactive immunological reactivity, for example, as defined by rabbit polyclonal antisera. For instance, the other wild type strain of *A. xylinum* ATCC 23769 which was used by the present inventors possesses a 75 kD polypeptide as a catalytic subunit of cellulose synthase by using the methods of the invention.

In certain general aspects, the invention relates to the preparation and use of DNA segments, including vectors or DNA fragments, having a sequence encoding a cellulose synthase polypeptide. For vectors, any number are known in which DNA sequences of the invention may be incorporated. The vector pUC18 has been demonstrated to be of particular value. Likewise, the related vectors M13mp18 and M13mp19 may be used in certain embodiments of the invention, in particular, in performing dideoxy sequencing.

In certain embodiments, the vector will contain a substantially purified DNA fragment which encodes at least a useful portion of a cellulose synthase polypeptide which includes the amino acids 1 to 723 of FIG. 1A–FIG. 1L, (SEQ ID NO:2) functionally equivalent amino acids. Recombinant vectors and isolated segments may, therefore, variously include the basic cellulose synthase coding region itself or may contain coding regions bearing selected alterations or modifications in the basic coding region of cellulose synthase. Alternatively, such vectors or fragments may encode larger proteins or peptides which nevertheless include the basic coding region. In any event, it should be appreciated that due to codon redundancy, as well as biological functional equivalence, this aspect of the invention is not limited to the particular DNA sequences shown in FIG. 1A–FIG. 1L, (SEQ ID NO:1).

Recombinant vectors such as the foregoing are useful both as a means for preparing quantities of the cellulose synthase-encoding DNA itself, and as a means for preparing the encoded protein and peptides. It is contemplated that where cellulose synthase proteins of the invention are made by recombinant means, one may employ either prokaryotic or eukaryotic expression and shuttle systems.

Prokaryotic host cells are disclosed in a preferred embodiment of the invention. However, in that prokaryotic systems are usually incapable of correctly processing eukaryotic precursor proteins, and since eukaryotic cellulose synthases are anticipated using the teachings of the disclosed invention, one may desire to express such sequences in eukaryotic hosts. However, even where the DNA segment encodes a eukaryotic cellulose synthase, it is contemplated that prokaryotic expression will have some additional applicability. Therefore, the invention can be used in combination with vectors which can shuttle between the eukaryotic and prokaryotic cells. Such a system is that of the Ti plasmids used in conjunction with the bacteria *Agrobacterium tumefaciens*.

Where expression of cellulose synthase in a eukaryotic host is contemplated, it most likely will be desirable to employ a vector such as a plasmid, that incorporates a eukaryotic origin of replication, such as those of the CaMV (cauliflower mosaic virus) and plasmids derived therefrom. Additionally, for the purposes of expression in eukaryotic systems, one will desire to position the cellulose synthase encoding sequence adjacent to and under the control of an effective eukaryotic promoter such as promoters used in combination with Ti plasmids. To bring a coding sequence under control of a promoter, whether it is eukaryotic or prokaryotic, what is generally needed is to position the 5' end of the translation initiation site of the proper translational reading frame of the protein between about 1 and about 50 nucleotides 3' of or "downstream" with respect to the promoter chosen. Furthermore, where eukaryotic expression is anticipated, one will typically desire to incorporate into the transcriptional unit which includes the cellulose synthase, an appropriate polyadenylation site. Typically, the polyadenylation site is placed about 30–2000 nucleotides "downstream" of the termination site of the protein at a position prior to transcription termination.

Accordingly, in certain preferred embodiments, the vectors of the invention are those where the cellulose synthase polypeptide encoding sequence is positioned adjacent to and under the control of an effective promoter. The vectors may be that set of vectors known well to those of skill in the art where the promoter comprises a prokaryotic promoter, the vector being adapted for expression in a prokaryotic host. Alternatively, the vectors may be those of common knowledge to skilled artisans where the promoter comprises a eukaryotic promoter, and the vector further includes a polyadenylation signal positioned 3' of the carboxy-terminal amino acid, and within a transcriptional unit of the encoded protein.

In certain embodiments of the invention, it is contemplated that DNA fragments both shorter and longer which incorporate sequences from FIG. 1A–FIG. 1L, (SEQ ID NO:1) will find additional utilities, including uses as short DNA fragment hybridization probes, e.g., in screening both prokaryotic and eukaryotic recombinant clone banks. In any.event fragm ents, corresponding to the sequence in FIG. 1A–FIG. 1L, (SEQ ID NO:1) stretches as short as 14 or so nucleotides, will generally find utility in accordance with these or other embodiments. By having stretches of at least about 14 nucleotides in common with the cellulose synthase DNA sequence of FIG. 1A–FIG. 1L, (SEQ ID NO:1) or it complement, a DNA segment will typically have the ability to form a preferential hybridization with cellulose synthase species DNA, particularly under more stringent conditions such as 0.15 M sodium chloride and 0.02 M sodium citrate, pH 7.4 at about 50° C. While such a complementary or common stretch will typically ensure the ability to form a stable hybrid, longer stretches of complementary DNA may prove more desirable for certain embodiments. Thus, one may desire to use DNA segments incorporating longer stretches of complementarity, for example, on the order of 18, 22 or even 25 or so bases.

The invention also provides methods for isolating cellulose synthase polypeptides from both recombinant and non-recombinant sources. Such a protein will typically include an amino acid sequence corresponding to amino acids 1 to 723 of FIG. 1A–FIG. 1L, (SEQ ID NO:2). However, them methods, of the invention have been demonstrated to be successful in isolating a 75 kd cellulose synthase polypeptide from *A. xylinum* strain ATCC 23769. It will be obvious to those of skill in the art that this 75 kd polypeptide is different in molecular weight from the 83 kd polypeptide described extensively herein. Furthermore, it will be obvious to such skilled artisans that the differences in molecular weights of these two polypeptides may result from actual differences in the primary structure of the amino acid chains themselves or may result from any number of post-translational modifications. Since such a protein represents the sequence for the catalytic subunit of the cellulose synthase protein, such a protein may be used directly to synthesize cellulose when provided the proper environment and substrate. Additionally, such a protein may be used to prepare an antibody for use in certain embodiments which antibody may be either a polyclonal or a monoclonal antibody and which, in any case, represents an antibody immunologically reactive with any of the polypeptides of the invention.

The invention provides, therefore, a method of producing a recombinant cellulose synthase polypeptide. This method includes the use of a recombinant host cell where the recombinant host cell is capable of expressing a recombinant cellulose synthase polypeptide. Furthermore, the method for producing recombinant cellulose synthase provided in the invention includes culturing the host cell under conditions appropriate for expressing the polypeptide. Finally, the method of production claimed would include collecting the polypeptide thus expressed.

The method is particularly applicable where one desires to obtain a polypeptide corresponding to an 83 kd catalytic subunit of cellulose synthase of *Acetobacter xylinum*. However, it is proposed that the method may be directed to isolation of a cellulose synthase polypeptide and a gene that is encoding a protein that is substantially similar to the 83 kd catalytic subunit.

In particular embodiments, the method will typically involve selecting cells that are capable of cellulose synthesis, particularly cells of *Acetobacter xylinum*. A variety of cells are amenable to the method of the invention, for instance, cells of Agrobacterium, Rhizobium, Alcaligenes and particularly Sarcina. Of course, methods will typically involve culturing cells such that cellulose synthase is produced. In most cases, the cell lines used in the method will be one of those cell lines which can actively engage in cellulose biosynthesis without addition of extraneous activators. Where cells of *Acetober xylinum* will be used, cultures will be grown in aerated and agitated culture medium containing Celluclast in order to free the cells trapped in the product cellulose so that greater numbers of cells can be produced as an inoculum (see U.S. patent application, Ser. No. 022,904, filed Mar. 6, 1987, Brown et al.).

In certain embodiments, cellulose synthase may be partially purified from cells by solubilizing the cellular membranes. Partially purifying cellulose synthase from cells by solubilizing the cellular membranes is preferably accomplished using digitonin. However, other solubilizing agents may be employed as long as the cellulose synthase enzyme thus solubilized retains a substantial amount of its native activity. Other solubilizing agents which may be used include n-octyl glucoside and other nonionic detergents or Triton X-100.

Moreover, one may desire to even further purify the enzyme. If so, it has been found that a particularly useful approach employs "product entrapment". Product entrapment is explained in greater detail in the examples which follow. This technique entails generally layering solubilized enzyme solution on top of a cushion, e.g., of buffered glycerol, allowing synthesis of cellulose to occur, centrifuging the resulting mixture and recovering the supernatant. This may even be followed by a series of chromatographic steps to still further purify the protein.

After obtaining a partially purified cellulose synthase one may desire to admix it with a cellulose synthase activator in order to enhance the activity of the purified cellulose synthase. A useful cellulose synthase activator is bis-(3',5')-cyclic diguanylic acid, this molecule being the only such activator currently identified.

The present inventors have found a photoincorporation method to function in identifying the active subunit of the cellulose synthase. Photoincorporation may be desirable where other modes of labelling the active enzyme are insufficient. Photoincorporation of cellulose synthase is accomplished most readily using a radioactively labeled azidonucleotide analog capable of specifically interacting with the nucleotide binding site of cellulose synthase.

Upon sequencing the purified cellulose synthase one may construct oligonucleotide probes corresponding generally to some portion of the DNA segment which would encode such amino acid sequences as are determined from amino acid sequencing the purified cellulose synthase. Oligonucleotide probes which incorporate particular DNA sequences will preferably correspond to at least a portion of the amino acid sequences or various cellulose synthase polypeptides in accordance herewith, and may be synthesized by a variety of methods. Preferably, these probes will be DNA sequences which encode portions of the *Acetobacter xylinum* 83 kd cellulose synthase polypeptide. In any case, the resulting probes will be used to probe a suitable source of DNA from a cell line capable of cellulose synthesis.

The probing will usually be accomplished by hybridizing the oligonucleotide probes to a DNA source suspected of possessing a cellulose synthase gene. In some cases, the probes will constitute only a single probe, in others, the probes will constitute a collection of probes based on a certain amino acid sequence of the cellulose synthase and will account in their diversity for the redundancy inherent in the genetic code.

A suitable source of DNA from a cell line capable of cellulose synthase expression may be a genomic library of the cell line of interest. Alternatively, the suitable source of DNA may include total DNA from the cell line of interest. Once the hybridization process of the invention has identified a candidate DNA segment, one will desire to confirm that a positive clone has been obtained, e.g., by further hybridization, sequencing and/or expression and testing.

The invention also provides a means for obtaining a variety of recombinant host cells which incorporate a DNA, sequence in accordance with that depicted in FIG. 1A through is (SEQ ID NO:2). The host cell may be either prokaryotic or eukaryotic in nature. In any case, it is understood that the DNA segment encoding a cellulose synthase polypeptide will also possess the regulatory signals functional in the particular host cell. A preferred embodiment includes a recombinant plant entity which may comprise a plant cell (e.g., tissue cultured plant cells), a recombinant seed, or a recombinant plant having an incorporated gene encoding for a cellulose synthase polypeptide. The plant entity will possess the recombinant gene as a result of the in vitro introduction of the gene into a plant cell, wherein the recombinant gene is under the transcriptional control of regulatory signals functional in the particular plant entity. These regulatory signals will be appropriately selected to control the expression of the recombinant cellulose synthase in a manner to allow all the requisite transcriptional and post-transcriptional modification.

Of particular interest in this regard will be plant entities which are cultivated for their content of cellulose and, most particularly, will be such plant entities as species of the genus Gossypium. Alternatively, more primitive entities such as algae or cyanobacterium are included within the description. Importantly, the gene encoding cellulose synthase may either be a gene which is heterologous to the plant cell, seed or plant in which the gene is introduced or it may be a copy of the gene homologous to that found in the plant entity being transformed. As used herein, the terms heterologous and homologous refer to the source of the recombinant DNA in reference to the DNA of the host cell. Thus, *A. xylinum* DNA from a particular strain of this bacterium which is encoding a cellulose synthase polypeptide if used to transform another strain of cellulose synthase-producing host cell bacteria or if used to transform a eukaryotic host cell would be the incorporation into either host cell of a DNA segment heterologous to that of the host cell's DNA. Conversely, the incorporation of the same *A. xylinum* DNA as above by retransforming an identical strain of *A. xylinum* would be the incorporation of a DNA segment homologous to that of the host cell's DNA.

In certain general aspects, then, a method of producing a cellulose synthase polypeptide is provided by the invention. First, one produces a recombinant host cell according to the methods and with the compositions of the invention such that the recombinant cell so produced is capable of expressing the polypeptide. Next, one cultures the host cell under conditions appropriate for expressing the polypeptide. Finally, according to the methods and with the compositions of the invention the recombinant polypeptide is recovered.

In other general aspects, a method of producing a β-1,4 glucan polymer is provided using the methods and compositions of the invention. First, one obtains one of the recombinant host cells of the invention using the methods and compositions of the invention such that the host cell so obtained is capable of producing the β-1,4 glucan polymer. Next, one cultures the host cell under conditions appropriate for producing the β-1,4 glucan polymer. Finally, one recovers the β-1,4 glucan polymer thus produced.

It will be obvious to those of skill in the art that the recombinant cellulose synthase polypeptide expressed by these host cells may use as its sole substrate UDP-glucose and produce the homoploymer cellulose. Alternatively, the substrate for the recombinant polypeptide may be other nucleotide or mixtures of nucleotides with UDP-glucose such as UDP-xylose and will result it heteropolymers. Furthermore, the recombinant cellulose synthase may act alone in these host cells or may act in concert with other enzymes to produce mixed polymer compositions.

BRIEF DESCRIPTION OF THE DRAWINGS

FIG. 1A–FIG. 2L DNA/protein sequences SEQ ID NO:1 of the *A. xylinum* cellulose'synthase catalytic subunit gene. The coding sequence begins at DNA position 636 and ends at DNA position 2804. The protein sequence SEQ ID NO:2begins at amino acid position 1 and ends at amino acid position 723. The three letter code used in the protein sequence here corresponds to amino acyl residues as follows: Ala, alanine; Arg, arginine, Asn, asparagine; Asp, aspartic acid, Cys, cysteine, Glu, glutamine; Glu, glutamicn acid, Gly, glycine; His, histidine; Ile, isoleucine; Leu, leucine; Lys, lysine; Met, methionine; Phe, phenylalanine; Pro, proline; Ser, serine, Thr, threonine; Tyr, tyrosine; Trp, tryptophan; Val, valine.

FIG. 2. 8% LDS-PAGE of cellulose synthase purified from *Acetober xylinum*. Lanes 1 to 5 were stained with Coomassie blue; lanes 6 to 8 were stained with silver. Lane 1, TS (20 μg), Triton X-100-solubilized enzyme preparation; Lane 2, TSt (20 μg), Triton X-100-solubilized enzyme preparation from trypsinized washed membranes; lane 3, TS-$EP_1$ (5 μg), the purified enzyme by one step of entrapment, $EP_1$, from the TS; lane 4, TSt-$EP_1$ (5 μg), the enzyme purified by one step of entrapment, $EP_1$, from TSt; lane 5, TSt-$EP_2$ (40 μg), the enzyme purified by two steps of entrapment, $EP_2$, from the TSt. This lane was overloaded deliberately in order to show the purity of the enzyme; lane 6, TSt-$EP_1$ (3.0 μg); lane 7, TSt-$EP_2$ (p.5 μg); lane 8, TSt-$EP_2$ (1.5 μg).

Figure 2:
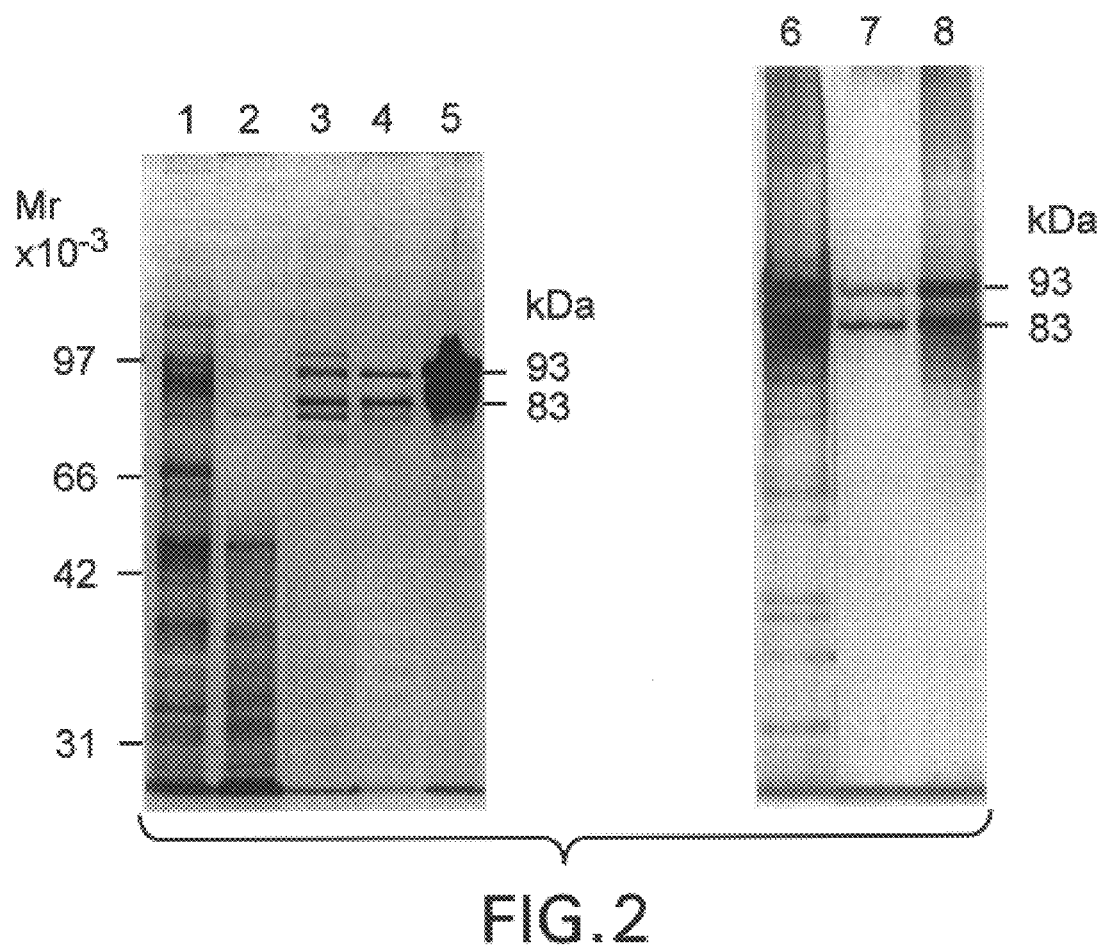

Samples in lanes 5 and 6 are the purified cellulose synthase from digitonin-solubilized preparations (3 μg of protein per lane). Either plus (+) or minus(−) μl of cellulose synthase activator contained in reaction mixture is indicated.

FIG. 9. Coomassie Blue stained 8% gel (A) and its corresponding autoradiography (B) of the cellulose synthase in purified fractions prepared by three detergents, digitonin, Triton X-100, and n-octyl glucoside, respectively. Samples in lanes 1 and 2 are the enzymes purified from the digitonin-extracted preparations (5 μg of protein per lane). The sample in lane 3 is the enzyme purified from the n-octyl glucoside-extracted preparations (2.35 μg of protein). The sample in lane 4 is the enzyme purified from the Triton X-100-extracted preparations (5 μg of protein). The reaction mixture not illuminated with UV light is shown in lane 1.

Figure 10:
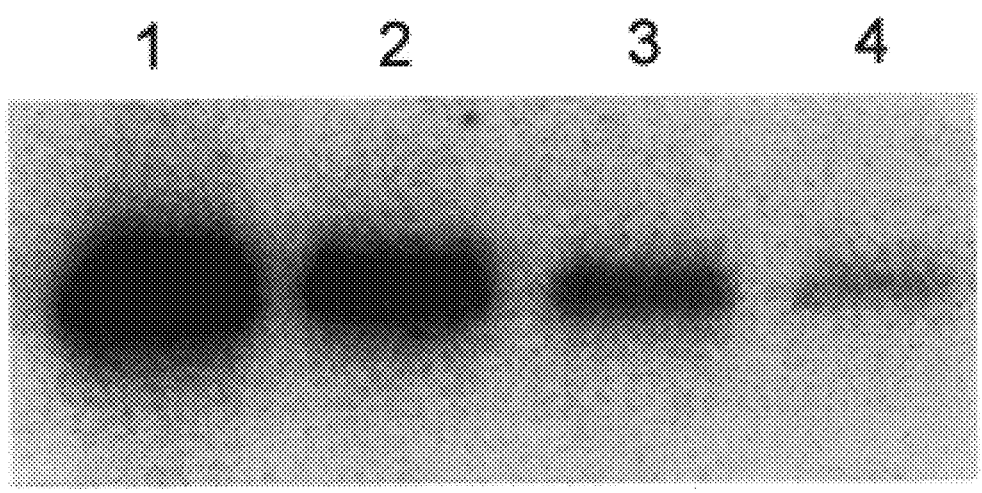

FIG. 10. Autoradiograph demonstrating the prevention of [P-$^{32}$P]5N$_3$UDP-glc photoinsertion into the 83 kd polypeptide by various concentrations of UDP-glc; 3 μg of the enzyme purified from digitonin-extracted preparations for each lane. UDP-glc was added to reaction mixture at final concentrations of 0 (lane 1), 50 (lane 2), 100 (lane 3), and 300 μM (lane 4).

Figure 11:
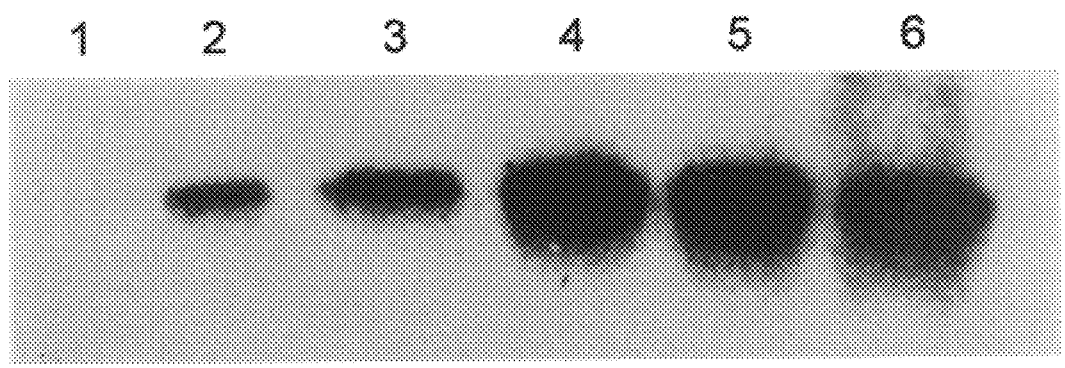

FIG. 11. Autoradiograph demonstrating the saturation of [β-$^{32}$P]5N$_3$UDP-glc photoinsertion into the 83 kd polypeptide. The final molar concentrations of [β-$^{32}$P]5N$_3$UDP-glc in the reaction mixtures were 20 (lanes 1 and 2), 50 (lane 3), 100 (lane 4), 300 (lane 5), and 500 μM (lane 6), respectively. Use of preirradiated [β-$^{32}$P]5N$_3$UDP-glc is shown in lane 1.

Figure 12:
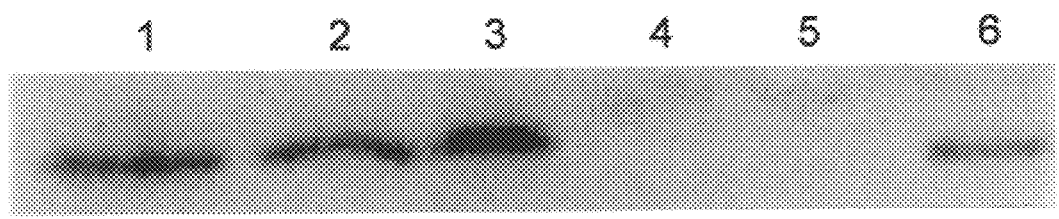

FIG. 12. Autoradiograph demonstrating the labeling of a 57 kd polypeptide in the digitonin-solubilized enzyme preparations. note that contaminating ($^{32}$P)glc-1-P may be present in the preparation of the [β-$^{32}$P]5N$_3$UDP-glc probe. The digitonin-solubilized enzymes, 20 μg of protein per lane, were incubated with 40 μM of [β-$^{32}$P]5N$_3$UDP-glc (4 mCi/μmole) either alone, lanes 1 to 3, or in the presence of 500 μM glc-6-P (lane 4), glc-1-P (lane 5), and glc-1,6-P (lane 6). For the control experiments, the preirradiated [P-$^{32}$P]5N$_3$UDP-glc was used (lane 1) or the reaction mixture not irradiated as shown in lane 2.

DESCRIPTION OF PREFERRED
EMBODIMENTS

In accordance with the present invention, access is provided for the first time to both recombinant and non-recombinant cellulose synthase. Methods are provided herein for the preparation of such enzymes in a substantially purified state. Since cellulose is ubiquitous throughout the plant kingdom, and since great effort has gone into attempts to isolate this highly important plant enzyme, the disclosure of this invention constitutes a true watershed in cellulose biochemistry.

The commercial applications of recombinant cellulose synthase and recombinantly produced cellulose have only begun recently to be explored since up until the present invention, no recombinant gene encoding a catalytic subunit of a cellulose synthase enzyme had been isolated. The present invention, provides such a capability for the first time. In preferred embodiments, the recombinant genes for cellulose synthase represented by this invention are obtained using a microbial cell line. However, the present invention contemplates that recombinant genes for cellulose synthase may be derived from eukaryotic cell lines as well.

Commercial applications of microbially derived cellulose, from the bacterium *Acetobacter xylinum* for instance, has distinct advantages over traditional, non-microbial sources of this ubiquitous natural polymer. For instance, no delignification is required following harvest. Moreover, the product can be synthesized directly into an extremely strong non-woven textile of virtually any shape thereby reducing many steps in the conversion of natural cellulose into a finished product. The invention provides a recombinant cellulose synthase whereby the physical properties of the product of the enzyme (cellulose) such as crystallinity, hydrophobicity, and degree of polymerization can be controlled during synthesis. Most importantly, however, the present invention provides the unique possibility of producing commercially feasible levels of cellulose from a wide variety of substrates. It should be possible, using the recombinant gene of the invention, to transform, for instance, photosynthetic, nitrogen-fixing prokaryotes (cyanobacteria) or single-celled eukaryotes (algae).

The ability to alter physical characteristics of the cellulose in situ may provide an efficient method for producing a broad range of value-added products not possible before the recombinant cellulose of the present invention was obtained. Previously, the development of a commercially feasible fermentation system for producing cellulose from bacteria has presented a significant technological challenge. Even using the most preferred bacterial strain, large-scale fermentation has been complicated by a number of phenomena associated with the biology of acetic acid bacteria including strain instability, the synthesis of gluconic acid as a significant by-product, and poor oxygen diffusion through the cellulose product of this strictly aerobic bacterium.

The present invention overcomes most of the complications of the prior art by providing a means for producing a recombinant cellulose synthase. The recombinant cellulose synthase of the present invention should allow production of a wide array of cellulose based products with significantly higher efficiency than the natural sources of cellulose. In so doing, the present invention may make its greatest contribution by preserving valuable natural resources.

For instance, cellulose from the cell walls of woody plants is formed in close association with lignin, hemicellulose, and other compounds. For many applications, such as in paper manufacture, wood cellulose must first be delignified by an extensive process known as pulping. Depending upon the process employed, pulping requires four or five processing steps following logging to obtain a partially purified cellulose material (Kirk-Othmer *Concise Encyclopedia of Chemical Technology* 1985). In contrast, *Acetobacter xylinum* and the recombinant cellulose synthase derived therefrom will be capable of synthesizing an extracellular ribbon of nearly pure cellulose directly into the incubation medium. The ribbons of individual bacterial cells interweave to form a hydrophilic cellulose membrane known as a pellicle.

The production of relatively high yields of Acetobacter cellulose without the corresponding synthesis of lignin and hemicelluloses greatly facilitates the process required to purify the cellulose. Nearly all of the cellular biomass and incubation medium components can be efficiently removed from the pellicle by a simple cleaning process. If necessary, the pellicle can then be dried by various means as required for a particular end product use. The simpler cleaning process of Acetobacter cellulose may result in higher end product yields with greater purity than can be obtained by the pulping process required for woody cellulose products.

The native Acetobacter pellicle has outstanding hydrophilicity and it is believed that the recombinant cellulose synthase will share this attribute. Depending upon synthetic conditions, it may have a water holding capacity ranging from 60 to 700 times its dry weight. The hydrophilicity of the cellulose pellicle is due in part to the extensive interior surface area of the interstitial spaces of the "never dried" pellicle/microfibril matrix. The presence of pore structures and "tunnels" within the wet pellicle may be the reason for its rapid uptake of post synthetic processing agents or dyes (Thompson 1988). Other sources of cellulose, such as cotton and wood enter the manufacturing process in a more compacted form. This form is not only less hydrophilic than microbial cellulose but is also less susceptible to chemical treatments or to dye uptake. As a consequence, harsher physical and chemical processing is required, reducing cellulose yields and increasing processing costs.

The strictly aerobic nature of Acetobacter may lend itself to industrial application. In undisturbed cultures, Acetobacter forms the cellulose pellicle at the air/liquid interface. Through the use of gas permeable molds, "microwoven" textiles of virtually any shape can be produced (U.S. patent application, Ser. No. 339,889 [continuation of U.S. patent application, Ser. No. 684,844], filed Apr. 17, 1989, Brown et al.). It has been demonstrated that a molded, seamless fabric in the shape of a glove can be formed in situ by an active Acetobacter culture. These microbial textiles can be synthesized into extremely thin, pliable forms which are gas and liquid permeable. The recombinant cellulose synthase of the present invention being derived from these bacterial cells will most likely share these unique advantages. Moreover, the significant advantage presented by the recombinant cellulose synthase will overcome the problems associated with the use of the natural bacterium.

The native Acetobacter pellicle has mechanical properties, including shape retention and tear resistance, which are superior to many synthetic fibers. It has been reported that following heat and pressure treatment, microbial cellulose has a Young's Modulus (a measure of shape retention) of 30 giga-Pascals, 4 times greater than any organic fiber (*The Japan Industrial Journal*, May 15, 1987; *Japanese New York Times*, May 29, 1987). The same report indicates that the tensile strength (tear resistance) of the treated material is five times greater than polyethylene or vinyl chloride films. Sony Corporation (Japan) has taken advantage of the shape retention properties of the treated Acetobacter cellulose in the development of a high fidelity audio speaker diaphragm made from the material (*The Japan Industrial Journal*, May 15, 1987; *Japanese New York Times*, May 29, 1987). The Ajinomoto Company (Japan), a collaborator with Sony in the development of the cellulose treatment process, has begun distributing samples of ultrahigh strength paper manufactured from Acetobacter cellulose (*The Japan Industrial Journal*, May 15, 1987; *Japanese New York Times*, May 29, 1987). These commercial applications are indicative of the types of applications which will benefit significantly from the current inventions compositions and methods.

Perhaps the most significant advantage of the invention, however, stems from the possibility that it presents to produce cellulose from a wide array of potential substrates. *Acetobacter xylinum*, itself, is capable of producing cellulose from a variety of inexpensive carbon substrates. Widely available commodity sources of carbon which may be utilized by Acetobacter include dextrose (glucose), sucrose, fructose, invert sugar, ethanol and glycerol [Tarr and Hibbert (1934); Barsha and Hibbert (1934)]. This diversity of utilizable substrates provides considerable flexibility in the location of the manufacturing facility since at least one of these substrates is produced in virtually every region of the world. Flexibility in the manufacturing process is enhanced by the ability to substitute among a variety of possible fermentation substrates and provides some independence from impact of price increases for an individual substrate. The ability to employ a substrate diversification strategy is particularly advantageous in view of the significant price volatility associated with international agricultural commodity products.

In particular, with the methods and compositions of the present invention, an even wider range of potential substrates becomes possible. It is not unlikely that the recombinant bacterial gene disclosed herein when placed on the appropriate vector and into the appropriate cell line, may be capable of directing cellulose production in a photosynthetic, nitrogen fixing cell thereby converting carbon dioxide and water directly into the desired product. The substantial advantages represented by this embodiment will be apparent to those of skill in the art.

A major advantage of Acetobacter cellulose technology lies in the ability to control the physical characteristics of the native cellulose as it is being synthesized. These advantages will be even more available utilizing the recombinant cellulose synthase of the invention. Previous investigations have demonstrated that the addition of direct dyes such as Congo Red, fluorescent brightening agents such as Tinopal LPW, and carboxycellulose derivatives to the Acetobacter culture can alter the assembly of the cellulose ribbons [Ben-Hayyim and Ohad (1965); Haigler et al. (1982)].

Depending upon the agent employed and its concentration, a variety of cellulose structures can be produced. The variation in these structures can range from individual microfibrils that are loosely associated into ribbons to completely disassociated fibrillar structures, resulting in amorphous cellulose. The extension of this earlier research has resulted in the development of a proprietary process which can significantly effect the absorptive properties of Acetobacter cellulose. This process enables nearly complete rehydration of the pellicle to its original hydrophilicity even after three cycles of wetting followed by drying at elevated temperatures (U.S. patent application, Ser. No. 022,904, filed Mar. 6, 1987, Brown et al.). It may be possible that Acetobacter cellulose synthesized by this process can be used as a reusable super-absorbent material. At any rate, the recombinant cellulose synthase of the present invention greatly enhances the already substantial benefits of these procedures.

The ability to control the cellulose synthesis process within a closed system provides several advantages. It enables the manufacturer to alter the properties of the microbial cellulose to a greater degree than would be possible by post-synthetic processing of other sources of cellulose. By manipulating the cell density, incubation conditions, fermentation vessel configuration, and media components, the opacity, strength and pliability of the harvested cellulose product can also be controlled. It may be possible to control the degree of polymerization of the cellulose as well (U.S. Pat. No. 450,324, issued Dec. 19, 1982).

The compositions and methods of the invention which now make possible these commercially desirable goals, are exemplified below. In order to achieve the considerable advantages of the invention, purification of cellulose synthase to a substantially purified state must first be accomplished. Next, the substantially pure cellulose synthase is used in order to identify the catalytic subunit of this multiple subunit enzyme. Following this identification, the catalytic subunit is at least partially sequenced and used to design oligonucleotide probes for hybridizing to the DNA of a cellulose synthase containing cell line. The resulting hybridizing DNA is cloned and used to derive a full length cellulose synthase gene from the DNA source. Once this has been accomplished, the substantial advantages provided by the compositions of the invention including the substantially purified protein and the DNA segments may be used in a wide range of applications and embodiments including transformation of cells with the recombinant cellulose synthase and use of the DNA probes of the invention to probe for similar genes in other DNA sources including eukaryotic plant DNAs.

Summary of Purification Studies

Beyer et al. (1981) presented several problems that must be overcome if a glycosyltransferase is to be successfully purified. These included: (i) selection of a cell strain which can produce a high yield of active transferase; (ii) an efficient harvest of viable cells from a selected culture method; (iii) a factor for stabilization of the enzyme; (iv) choice of the detergent; and, (v) an efficient purification procedure.

During the course of purification of cellulose synthase, the present inventors encountered a number of similar obstacles as well as ones unique to the cellulose synthases. Several strategies had to be developed in order to overcome these problems. First, an A. xylinum strain ATCC 53582 was selected since it has a greater enzyme activity than ATCC 23769. Second, a method for production of high yields of essentially cellulose-free Acetobacter cells using cellulase was refined [Dillingham (1961); U.S. patent application, Ser. No. 900,384, filed Aug. 26, 1986, Brown et al.). Third, Triton X-100 was used as the detergent and glycerol as the enzyme stabilizer.

The present inventors tested various purification methods, including sucrose or glycerol gradient ultracentrifugation, gel filtration with Sephacryl S-300, metal chelating affinity chromatography, anion-exchange chromatography with DEAE-Sepharose CL-6B, and affinity chromatography with UDP-glucuronic acid-agarose. However, all either failed or resulted in only a 2–3 fold purification of the synthase.

A high degree of purification was achieved by in vitro cellulose-entrapment. The reason for such a high degree of purification being achieved is unclear. However, it could be due to: (a) the enzyme may be tightly enclosed by its insoluble product and thus coprecipitates as speculated by Kang et al. (1984) for chitin synthetase; (b) the density of cellulose is high, about 1.27–1.6 (CRC Handbook of Chemistry and Physics. 1984), which allows the enzyme product complex to pass through the 30% glycerol layer; andor, (c) the 30% glycerol content of the cushion solution keeps most of the proteins in the reaction mixture during centrifugation.

It has been reported that three different subunits of the photosystem II reaction center could be isolated using Triton X-100, whereas five different subunits were obtained using digitonin (Nanba and Satoh 1987). Both purified preparations have the same photochemical activity. From these observations, the inventors proposed that different detergents might solubilize an oligomeric enzyme complex in association either with or without non-essential proteins, even after purification. This may also be the case with the purification of cellulose synthase using different detergents. Under reducing conditions, the 83 kd and 93 kd bands are present in all of the purified preparations. Furthermore, the 93 kd band was degraded and only the 83 kd band remained if the purified preparation was treated with trypsin. These results, in combination with the evidence from the characterization of cellulose synthase as a glycosylated protein, suggested that the 83 kd band is an essential part of the active cellulose synthase. However, the possible involvement of the 93 kd polypeptide with the cellulose synthase could not be excluded since the enzyme may consist of non-identical subunits. In addition, the presence of the other protein bands in the most purified preparations was still a considerable concern. Definitive identification of the subunit composition of cellulose synthase had to await further investigation.

Figure 4:
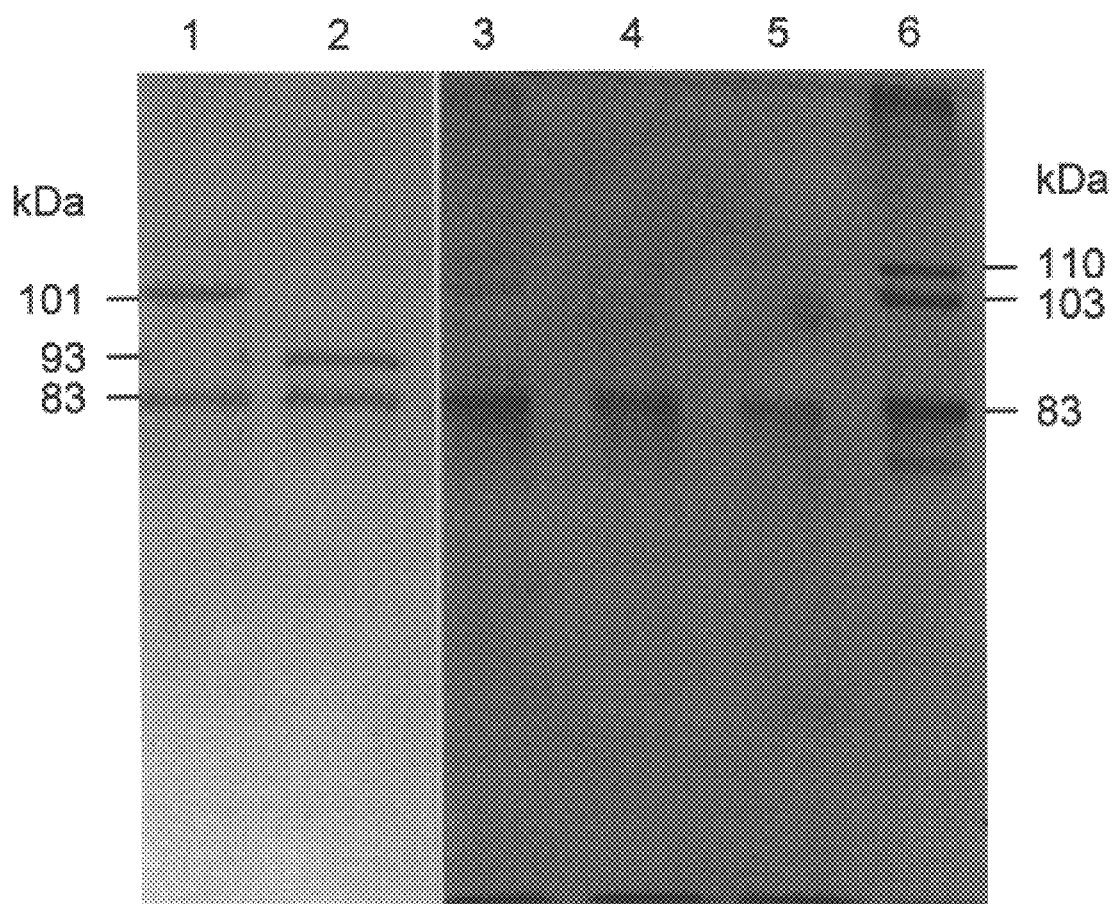
FIG. 4. Subunit composition of the purified enzyme: effect of reduction and trypsin. (A) 8% LDS-PAGE of the $EP_1$ fraction from TS prepared from trypsinized washed membranes. Samples (10 μg protein per lane) were electrophoresed in sample buffer with mercaptoethanol (lane 1) and without it (lane 2). Note the prominence of the 93- and 83 kd bands in lane 2. (B) 8% LDS-PAGE of the $EP_1$ fraction from DS in the absence of reducing agent. Samples (10 μg protein per lane) were gently shaken at 25° C. in the presence of trypsin (trypsin/$EP_1$=4 μg/1,000 μg of protein concentration) for two minutes (lane 3), five minutes (lane 4), 10 minutes (lane 5) and 0 minutes (lane 6).

As shown in FIG. 4 (lane 1 and 2) which is described more fully hereafter, the 93 kd band observed under reducing conditions and the 101 kd band seen under non-reducing conditions could be the same polypeptide with intramolecular disulfide bonds. The presence of two small spots in the position of the 93 kd band under non-reducing conditions (FIG. 4, lane 1, arrowheads), may be due to the partial degradation of intramolecular disulfide bonds during the preparation of the enzyme fraction. This also may explain the occurrence of two peaks present in the gel filtration elution profiles. In any case, such extraneous bands increased considerably the difficulty associated with the identification of the catalytic cellulose synthase polypeptide.

Dennis and Colvin (1965) noted that incubation of lysed cell preparations with trypsin at room temperature for 24 hours completely removed the cytoplasmic membrane and associated materials, and completely inhibited cellulose synthesis. They suggested that the site of synthesis might be the cytoplasmic membrane. Recently, Bureau and Brown (1987) also suggested that the cellulose synthase is located on the cytoplasmic membrane. However, their studies showed that cellulose synthase activity is maintained following brief trypsin treatment. Trypsin is well known for degrading proteins and also is effective for the cleavage of the peptidoglycan attachment region of lipoprotein in Gram-negative bacteria (Braun 1975). In studies disclosed herein, trypsin was found to have no effect on cellulose synthase activity and resulted in more efficient detergent solubilization of the enzyme. However, it was not clear: (i) why trypsin degraded the solubilized form of the 93 kd polypeptide, but did not degrade the membrane-bound form; or (ii) why the specific activity of the peak fraction from trypsin treated (TS; triton solubilized) is twice as great as the non-treated sample in gel filtration chromatographic studies. Elucidation of the interaction between trypsin and cellulose synthase required more study. Certainly, however, the ability to purify cellulose synthase provides a basis for certain surprising aspects of the invention. These techniques represent the first instance of the substantial purification of the cellulose synthase from A. xylinum, in particular, or any cellulose synthase, in general.

Summary of the Studies Designed to Identify the Active Subunit of Cellulose Synthase By using a photoaffinity labeling method, the substrate binding site of cellulose synthase, e.g., from Acetobacter xylinum strain ATCC 53582, has now been shown to be an 83 kd polypeptide. This polypeptide may include or comprise a regulatory subunit of cellulose synthase (i.e., the c-di-GMP binding subunit). The possible involvement of a 93 kd polypeptide in cellulose synthase complex cannot yet be excluded since the enzyme complex may consist of non-identical subunits for various functions in the polymerization and crystallization of cellulose (Lin and Brown 1989).

The 83 kd polypeptide had been partially characterized as a glycoprotein by lectin affinity chromatography, Schiff-periodate and fluorescein isothiocyanate-Concanavalin A staining analyses (Lin and Brown 1989). However, since membrane associated glycoproteins have been widely found to be difficult to purify, the finding that ($\beta$-$^{32}$P]5N$_3$UDP-glc binds to the catalytic subunit of cellulose synthase in A. xylinum provided the present inventors with a powerful tool for elucidation of the structure, function, and regulation of the cellulose synthase. Furthermore, it provided one means for the isolation of recombinant genes encoding the enzyme. Only upon purification did it become feasible to sequence the polypeptide and construct an oligonucleotide probe for cloning.

It is also important to note here that the present inventors have applied the techniques of the invention to the another wild type strain of A. xylinum known to produce cellulose I pellicles, ATCC 23769, and to a pellicle-free mutant derived from the ATCC 53582 strain (called NQ5). In so doing, the present inventors identified a 75-kD polypeptide as the catalytic subunit of cellulose synthase which is in contrast to the 83-kD subunit from ATCC 53582. Thus, the techniques described herein, are generally applicable for identifying the catalytic subunit of purified cellulose synthases.

Cloning and Sequencing Studies

Thus, the present invention provides a predictably successful, albeit difficult, method for the purification of cellulose synthase made feasible by the techniques discussed above. Using solely prior art techniques, others had failed to obtain cellulose synthase of adequate purity and quantity to enable either the identification of the active subunit or the sequencing of the active subunit polypeptide. Furthermore, considerable disagreement existed in the prior art concerning the size and immunological characteristics of the catalytic subunit of the cellulose synthase.

Application of cellulose entrapment, use of the cellulose synthase activator to enhance cellulose synthase activity, and photoincorporation identification of the catalytic subunit, among other techniques, all combined to allow the present inventors to supercede the prior art and go on to sequence the polypeptide and, ultimately, to clone the gene encoding it. It will be appreciated by those of skill in the art that once provided with the techniques for obtaining a substantially purified cellulose synthase, and with the amino acid sequences of the present invention, many of the difficult steps necessary for cloning and sequencing the gene encoding a cellulose synthase polypeptide have been overcome by the present invention.

Armed with the highly purified catalytic subunit of cellulose synthase, the present inventors were poised to utilize the techniques of molecular biology to clone and sequence the gene. However, considerable difficulties were encountered even at this stage.

Initially, the inventors attempted to obtain the amino acid sequence of the purified enzyme and failed. Only an ambiguous sequence resulted from these studies. However, upon proteolytic treatment with trypsin, a relatively non-ambiguous sequence was obtained. Based on the unambiguous sequence of the invention, eight 17-mer oligonucleotide were prepared for use as probes.

These probes were each used independently to determine which probe exhibited strongest binding potential when tested against total DNA derived from A. xylinum. This technique was a substantially high-risk experiment since even strains of E. coli not known to contain a cellulose synthase gene sequence were found to strongly bind to certain of the probes. Therefore, there was certainly no guarantee that any of these probes, even if should one demonstrate binding potential to A. xylinum, would be capable of hybridizing to the actual cellulose synthase DNA.

In fact, a further complication arose from the very demonstration that E. coli strains known to those of skill in the art readily bound the probes of the invention. Since these probes would most likely not be capable of detecting a recombinant gene sequence in such a background, the inventors were forced to forgo the typical technique applied by those of skill in the art, that technique being the creation of a total genomic DNA library based on the genomic DNA from A. xylinum. Instead, the inventors were forced to rely on the much less certain technique of using the selected probe to identify bands of hybridizing DNA from a gel containing total genomic A. xylinum DNA which had been treated with restriction endonuclease.

This only allowed the isolation of a certain subset of DNA which might hybridize specifically with the probe, so the resulting DNA was subcloned into a vector and used to transform host bacteria. Even further difficulties were encountered at this point since only very few recombinants were obtained, most likely due to the restriction of the A. xylinum heterologous DNA in E. coli. Additionally, since it was not possible to screen the host bacteria due to a high background of probe binding even under stringent conditions, the recombinant plasmids had to be reisolated from the clones, pooled into 50 isolates per group and tested once again with the probe DNA for groups which demonstrated binding. Only after the application of these multiple-step techniques were the inventors herein able to isolate the recombinant plasmid which contained the hybridizing DNA, to subclone individual fragments of this DNA to the point that they contained substantially only the sequence encoding cellulose synthase and then to sequence the DNA. The resulting fragments were utilized to obtain a DNA sequence of 2912 base pairs which was a region of the DNA sequence encoding a protein consisting of 723 amino acid residues.

As noted previously, it is believed that modification and changes may be made in the structure of the recombinant cellulose synthase protein and still obtain a molecule having like or otherwise desirable characteristics. For example, certain amino acids may be substituted for other amino acids in a protein structure without appreciable loss of interactive binding capacity with complementary structures such as antigen-binding regions of antibodies (e.g., binding sites on receptor molecules). Since it is the interactive capacity and nature of a protein that defines that proteins biological functional activity, certain amino acid sequence substitutions can be made in a protein sequence (or, of course, its underlying DNA coding sequence) and, nevertheless, obtain a protein with like or even countervailing properties (e.g., antagonistic v. agonistic). It is thus contemplated by the present inventors that various changes may be made in the sequence of the peptides (or underlying DNA) without appreciable loss of their biological utility or activity.

Biological Functional Equivalency

The importance of the hydropathic index of amino acids in conferring interactive biologic function on a protein has been discussed generally by Kyte and Doolittle (1982) wherein it is found that certain amino acids may be substituted for other amino acids having a similar hydropathic index or score and still retain a similar biological activity. As displayed in Table I below, amino acids are assigned a hydropathic index on the basis of their hydrophobicity and charge characteristics. It is believed that the relative hydropathic character of the amino acid determines the secondary structure of the resultant protein, which in turn defines the interaction of the protein with substrate molecules. It is proposed that functional equivalency may typically be maintained where amino acids having no more then a +/−1 to 2 difference in index, and more preferably within about a +/−1 difference, are exchanged.

TABLE I

| Amino Acid | Hydropathic Index |
| --- | --- |
| Isoleucine (Ile) | 4.5 |
| Valine (Val) | 4.2 |
| Leucine (Leu) | 3.8 |
| Phenylalanine (Phe) | 2.8 |
| Cysteine/cystine (Cys) | 2.5 |
| Methionine (Met) | 1.9 |
| Alanine (Ala) | 1.8 |
| Glycine (Gly) | −0.4 |
| Threonine (Thr) | −0.7 |
| Tryptophan (Trp) | −0.9 |
| Serine (Ser) | −0.8 |
| Tyrosine (Tyr) | −1.3 |
| Proline (Pro) | −1.6 |
| Histidine (His) | −3.2 |
| Glutamic Acid (Glu) | −3.5 |
| Glutamine (Gln) | −3.5 |
| Aspartic Acid (Asp) | −3.5 |
| Asparagine (Asn) | −3.5 |
| Lysine (Lys) | −3.9 |
| Arginine (Arg) | −4.5 |

Thus, for example, isoleucine, which has a hydropathic index of +4.5, can be substituted for valine (+4.2) or leucine (+3.8), and still obtain a protein having similar biologic activity. Alternatively, at the other end of the scale, lysine (−3.9) can be substituted for arginine (−4.5), and so on.

Accordingly, these amino acid substitutions are generally based on the relative similarity of R-group substitutents, for example, in terms of size, electrophilic character, charge, and the like. In general, exemplary substitutions which take various of the foregoing characteristics into consideration include the following:

TABLE II

| Original Residue | Exemplary Substitutions |
| --- | --- |
| Ala | gly; ser |
| Arg | lys |
| Asn | gln; his |
| Asp | glu |
| Cys | ser |
| Gln | asn |
| Glu | asp |
| Gly | ala |
| His | asn; gln |
| Ile | leu; val |
| Leu | ile; val |
| Lys | arg |
| Met | met; leu; tyr |
| Ser | thr |
| Thr | ser |
| Trp | tyr |
| Tyr | trp; phe |
| Val | ile; leu |

Site-Specific Mutagenesis

Site-specific mutagenesis is a technique useful in the preparation of individual peptides, or biologically functional equivalent proteins or peptides, derived from the cellulose synthase sequence, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications such as Adelman, et al. (1983), incorporated herein by reference. As will be appreciated, the technique typically employs a phage vector which exists in both a single stranded and double stranded form. Typical vectors useful in site-directed mutagenesis include vectors such as the M13 phage, for example, as disclosed by Messing et al. (1981), incorporated herein by reference. These phage are readily commercially available and their use is generally well known to those skilled in the art.

In general, site-directed mutagenesis in accordance herewith is performed by first obtaining a single-stranded vector which includes within its sequence a DNA sequence which encodes the cellulose synthase sequence. An oligonucleotide primer bearing the desired mutated sequence is prepared, generally synthetically, for example by the methods described herein. This primer is then annealed with the singled-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as E. coli cells and clones are selected which include recombinant vectors bearing the mutated sequence arrangement.

Host Cell Cultures and Vectors

In general, of course, prokaryotes are preferred for the initial cloning of DNA sequences and constructing the vectors useful in the invention. For example, E. coli. HB101 has been shown to be particularly useful. Other microbial strains which may be used include E. coli strains such as E. coli B, and E. coli X 1776 (ATCC No. 31537). These examples are, of course, intended to be illustrative rather than limiting.

Prokaryotes may also be used for expression. The aforementioned strains, as well as E. coli W3110 (F-, lambda-prototrophic, ATCC No. 273325), bacilli such as Bacillus subtilus, or other enterobacteriacea such as Salmonella typhimurium or Serratia marcesans, and various Pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species and well known to those of skill in the art. The vector pBR 322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

Those promoters most commonly used in recombinant DNA construction include the β-lactamase (penicillinase) and lactose promoter systems and a tryptophan (trp) promoter system each of which is well known to those of skill in the art. While these are the most commonly used, other microbial promoters have been discovered and utilized, and details concerning their nucleotide sequences have been published, enabling a skilled worker to ligate them functionally with plasmid vectors.

In addition to prokaryotes, eukaryotic microbes, such as yeast cultures may also be used. *Saccharomyces cerevisiase*, or common baker's yeast is the most commonly used among eukaryotic microorganisms, although a number of other strains are commonly available. For expression in Saccharomyces, the plasmid YRp7, for example, is commonly used. This plasmid already contains the trpl gene which provides a selection marker for a mutant strain of yeast lacking the ability to grow in tryptophan, for example ATCC No. 44076 or PEP4-1. The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes [Hess et al. (1968); Holland et al. (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

Cotton Transformation

An example is provided which illustrates the manner in which an agronomic or other eukaryotic plant species may be transformed with recombinant cellulose synthase. It is based on the successful transformation of cotton (Gossyvium hirsutum) with a recombinant gene for kanamycin resistance from bacteria, a situation not unlike that which the present invention now makes possible for transformation of plant cells with bacterial cellulose synthase. It will be recognized by those of skill in the art, that there be certain limitations unique to the cellulose synthase enzyme of the present invention which may not be addressed in the example below. However, the example demonstrates that there are not insurmountable obstacles to transforming a cotton plant with a bacterial cellulose synthase.

The technique basically utilizes a binary plant vector strategy based on the *Agrobacterium tumefaciens* Ti plasmid. It further involves the cloning of the cellulose synthase gene in a plant transformation vector (PTV). This modified vector is then mated from *E. coli* into the Agrobacterium and recombinant colonies are selected which contain the recombinant gene. The Agrobacteruim strain carries a "disarmed" Ti-plasmid. Virulence functions on the Ti-plasmid interact in trans with the border sequence on the PTV thereby mobilizing the cellulose synthase gene into the plant cell and inserting the gene into one of the host plant's chromosomes. Callus derived from these transformed cotyledons is treated with various plant hormones and stimulated to regenerate whole recombinant plants according to techniques known to those of skill in the art.

There are, of course, a variety of methods known to those of skill in the art for introducing recombinant genes into plants as well as a number of plant species into which recombinant DNA has been introduced (see generally, Gasser and Fraley 1989). In those systems where Agrobacterium-mediated transformation is efficient, such as in cotton as noted herein, it is the method of choice because of the ease and defined nature of the gene transfer system utilized. However, few monocotyledonous plants appear to be hosts for Agrobacterium, thus, extensive efforts have been directed toward alternative delivery systems for recombinant DNA into these species.

Certain of these techniques rely on physical means of introducing DNA into the plant cell. Transformation of protoplasts has been achieved through facilitating DNA uptake by calcium phosphate precipitation, polyethylene glycol treatment, electroporation, or combinations of these methods. These techniques rely on introduction of recombinant DNA into protoplasts of the plant cells. Where regeneration of protoplasts has been shown to be difficult, mechanical means to introduce recombinant DNA into intact cells or tissues has been successfully used. In particular, the use of particle guns (high-velocity microprojectile technology) has been shown to affect transformation of plant cells. Other methods with the potential to achieve plant cell transformation with recombinant DNA include transfer into pollen, direct injection into reproductive organs, 'microinjection into cells of immature embryos and rehydration of dessicated embryos.

Furthermore, a growing number of species have been reported from which the production of transgenic plants has been achieved with one or another of the techniques noted above. The following is a recently updated list of such plants and a reference to the method used to affect the transformation (see generally, Gasser and Fraley 1989: Abbreviations; AT, *Agrobacterium tumefaciens*; AR *Agrobacterium rhizogenes*; FP, free DNA introduction into protoplasts; PG, particle gun; MI, microinjection; IR, injection of reproductive organs).

| PLANT SPECIES | METHOD |
|---|---|
| Herbacious Dicots | |
| Petunia | AT |
| Tomato | AT |
| Potato | AT |
| Tobacco | AT, FP, PG |
| Arabidopsis | AT |
| Lettuce | AT |
| Sunflower | AT |
| Oilseed Rape | AT, MI |
| Flax | AT |
| Cotton | AT |
| Sugarbeet | AT |
| Celery | AT |
| Soybean | AT, PG |
| Alfalfa | AT |
| *Medicago varia* | AT |
| Lotus | AT |

-continued

| PLANT SPECIES | METHOD |
|---|---|
| *Vigna aconitifolia* | FP |
| Cucumber | AR |
| Carrot | AR |
| Cauliflower | AR |
| Horseradish | AR |
| Morning Glory | AR |
| Woody Dicots | |
| Poplar | AT |
| Walnut | AT |
| Apple | AT |
| Monocots | |
| Asaparagus | AT |
| Rice | FP |
| Corn | FP |
| Orchard Grass | FP |
| Rye | IR |

Plant DNA Hybridization

Another example is provided to illustrate a proposed use of the recombinant cellulose synthase of the present invention to probe plant DNA sources for hybridizing sequences. This method allows for a rapid microscale isolation of plant DNA without the use of CsCl gradients. The technique was developed for *Zea mays* but has been successfully applied to a variety of other plant species including *Nicotiana tabacum, N. plumbaginifolium, N. sylvestris,* Lyscopericum sp., Amaranthus sp., Glycine max, and *Petunia hybrida*.

In general, the technique involves isolating plant tissue DNA from leaf tissue by disrupting the cells of the leaf frozen in liquid nitrogen. The disrupted cell debris is then solubilized in detergent and buffer in order to remove most of the proteinaceous and polysaccharide materials. After filtering the debris from the buffered solution, plant DNA is then precipitated with alcohol, dried and resuspended in a buffered solution, then precipitated using a high salt-alcohol method. The resulting DNA may be used with restriction endonucleases and other DNA-modifying enzymes. It has also been demonstrated to be useful in filter hybridization using DNA probes such as those of the present invention.

As mentioned, in certain aspects, the DNA sequence information provided by the invention allows for the preparation of relatively short DNA (or RNA) sequences having the ability to specifically hybridize to gene sequences of the cellulose synthase gene. In these aspects, nucleic acid probes of an appropriate length are prepared based on a consideration of the sequence shown in FIG. 1. The ability of such nucleic acid probes to specifically hybridize to the cellulose gene sequences lend them particular utility in a variety of embodiments. Most importantly, the probes can be used in a variety of assays for detecting the presence of complementary sequences in a given sample such as the plant DNA samples described here. However, other uses are envisioned, including the use of the sequence information for the preparation of mutant species primers, or primers for use in preparing other genetic constructions.

To provide certain of the advantages in accordance with the invention, the preferred nucleic acid sequence employed for hybridization studies or assays includes sequences that are complementary to at least a 14 to 25, or so, nucleotide stretch of the sequence shown in FIG. 1. A size of at least 14 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102, or by introducing selected sequences into recombinant vectors for recombinant production.

Certain nucleotide sequences of the invention will be important for their ability to selectively form duplex molecules with complementary stretches of the gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids, for example, one will select relatively low salt and/or high temperature conditions, such as provided by 0.02M–0.15M NaCl at temperatures of 50° C. to 70° C. These conditions are particularly selective, and tolerate little, if any, mismatch between the probe and the template or target strand. Of course, for some applications, for example, where one desires to prepare mutants employing a mutant primer strand hybridized to an underlying template or where one seeks to isolate cellulose synthase coding sequences for related species, functional equivalents, or the like, less stringent hybridization conditions are called for in order to allow formation of the heteroduplex. In these circumstances, one would desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including radioactive, enzymatic or other ligands, such as avidin/biotin, which are capable of giving a detectable signal.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

While it is not specifically addressed in this example, the use of the methods and the compositions of the present invention may be applicable in certain instances to non-plant eukaryotes. In particular, oriented cellulose has been shown to be a component of certain mammalian tissues. There is considerable evidence that polysaccharides play an important role in the stabilization of connective tissue fibers and as such may play a role in certain disease conditions in humans such as scleroderma conditions [see generally, Hall et al., *Proc. Royal Soc. B* 151; 497 (1960)].

In any event or from whatever source, once the DNA fragments have been detected via these techniques, standard approaches known well to those of skill in the art may be utilized to further isolate and clone the fragments. As alternative sources of recombinant cellulose synthases, these new fragments will share all the utilities of the compositions described specifically herein.

Transformation of Cyanobacteria with Cellulose Synthase

Cyanobacteria (blue-green algae) are a diverse group of microorangisms that have two things in common: they are Gram negative prokaryotes and they carry out oxygenic, plantlike photosynthesis. Many strains of cyanobacteria are also capable of fixing atmospheric nitrogen. These properties make cyanobacteria prime candidates for transformation with recombinant cellulose synthase gene from *A. xylinum* in order to develop commercial scale cellulose production in a prokaryotic species capable of photosynthesis and nitrogen fixation.

Typically, no cellulose biosynthesis has been demonstrated in cyanobacteria under normal growth conditions. However, cellulose produced in the form of a slime has been reported in Nostoc [A. Frey-Wyssling, *The Plant Cell Wall*, p.227, Gebruder Borntager, Berlin (1976)]. The transfer of *A. xylinum* cellulose synthase gene into cyanobacteria is made possible with the methods and compositions of the present invention.

Gene transfer has been established and host-vector systems have been developed for gene cloning in Cyanobacteria (Kuhlemeier and Van Arkel 1987). Two strategies have been employed for gene cloning in Cyanobacteria. One uses shuttle plasmid vectors that carry both a cyanobacterial and an *E. coli* replicon, each of which functions in its indigenous host. Depending on the sequence of the cloned gene, the selection applied, and the cyanobacterial host, the cloned gene can be maintained on the autonomous plasmid or can be integrated into the cyanobacterial chromosome.

The other strategy exploits the efficient recombination system of certain cyanobacterial strains (*Anacystis nidulans* R2, Synechocystis sp. 6803) for a directed integration of the cloned gene into the chromosome (Golden et al. 1987). In the latter strategy a DNA vector that lacks a cyanobacterial replicon, but carries similar chromosomal sequences, is used. According to the imposed selective conditions, the cloned gene, either alone or together with the vector sequences, integrates into the chromosome.

Gene transfer in cyanobacteria is known to take place by conjugation and transduction as well as by transformation (Herdman 1982). Up to now, however, the only system of practical importance has been the transformation system (Porter 1988) and that is the preferred method described herein.

A number of bacterial antibiotic resistance genes are expressed in cyanobacteria, where they are used for selecting transformed cells (Golden et al. 1987). Apart from these, the larvicidal gene of *Bacillus sphearicus* 1593M was transformed into the cyanobacterium *Anacystis nidulans* R2, where it exhibited expression and toxin activity comparable to that observed with *E. coli* carrying the respective recombinant plasmids (Tandeau de Marsac et al. 1987). Use has also been made of the coding sequences of cat, lacZ, and lux to function as reporter genes in determining efficient promoter sequences (Friedberg 1988). The gene products of these genes can be assayed in cyanobacteria allowing scoring or selection of cells expressing the gene.

EXAMPLE I

Purification of Cellulose Synthase

Materials—Reagents were obtained from the following sources: UDP-[$^{14}$C]glc, lithium dodecyl sulfate, ICN; polyethylene glycol (PEG)-3350, Triton X-100, n-octyl glucoside, trypsin (EC 3.4.21.4), trypsin inhibitor, Concanavalin A (Con A) Sepharose 4B, methyl x-D-mannopyranoside, dansyl hydrazine, fluorescein isothiocyanate-labeled Con A (FITC-Con A), Sigma; digitonin, Serva; Celluclast, Novo Enzymes; guanosine-5'-triphosphate (GTP) dilithium salt, Boehringer Mannheim. All operations were performed at 0–5° C., unless otherwise indicated.

Cells—Two bacterial strains of *A. xylinum*, ATCC 53582 and ATCC 23769, were used. Cultures were maintained on Schramm and Hestrin's glucose medium as previously described (Schramm and Hestrin 1954). A single colony, grown for 5–7 days at 28° C. on agar plates, was transferred to a flask containing 200 ml of culture medium and 75 µl filtered Celluclast, and cultured at 28° C. on a rotary shaker set at 120 rpm for 42–48 hour [Dillingham (1961); U.S. patent application Ser. No. 900,384, filed Aug. 26, 1986]. A 5 ml aliquot of the starting culture was then transferred to a new flask having the same amount of medium and Celluclast and cultured under the same conditions. After 48 hours, the cell suspension was passed through 8 layers of cheesecloth and then centrifuged at 10,000×g for 10 minutes. The pellets were washed once in a buffer of 50 mM Tris-10 mM $MgCl_2$-1 mM EDTA, pH 7.5 (TME) as described by Glaser (Glaser 1958). The yield was about 1 gm of cells, dry weight, per liter of culture. The washed cell pellets were resuspended in TME containing 20% (weight/volume) PEG-3350.

Preparation of Membranes and Activator—"Washed membranes" and "crude factor" were prepared as described previously (Ross 1986) except that the cells were disrupted in an Aminco French pressure cell at 16,000 lb/in$^2$. Trypsinized membranes were prepared as follows: to 10 ml of washed membranes (protein concentration, 5 mg/ml), 0.2 mg of trypsin was added and gently shaken at 25° C. for 30 minutes. After the addition of 0.2 mg of trypsin inhibitor for 20 minutes, the mixture was centrifuged at 18,000×g for 20 minutes and washed once in TME.

Cyclic diguanylic acid, an activator of the cellulose synthase (Lin et al. 1985), was obtained in two ways as described (Ross 1986), but with several modifications: (i) 8 ml of crude factor was mixed with 1 ml 10 mM GTP, 0.1 ml 100 mM $CaCl_2$ and 0.9 ml TME buffer, and incubated at 37° C. for two hours. The reaction was terminated by heating in boiling water for three minutes, followed by centrifugation at 2,000×g for 10 minutes. This supernatant was called "crude Gx"; (ii) the activator was prepared as in (i) except that the reaction was terminated by addition of 0.6 M $HClO_4$ instead of heating. After centrifugation, the supernatant was neutralized with 5 M KOH and recentrifuged at room temperature. This supernatant was designated "N-Gx."

Solubilization by Nonionic Detergent—Either the washed membranes or the trypsinized membranes were resuspended in TME containing 20% glycerol, 0.6% (weight/volume) Triton X-100 to give a final protein concentration of 5.0 mg of membrane protein per ml. After homogenization with a Teflon homogenizer, the suspension was gently shaken for one hour, followed by centrifugation at 100,000×g for one hour. The supernatant represented the Triton-solubilized enzyme which was designated "TS" if the washed membranes were used, and "TSt" if the trypsinized membranes were used. The n-octyl glucoside-solubilized enzyme (OGS and OGSt are equivalent to TS and TSt) was prepared as TS except that 1% (weight/volume) n-octyl glucoside was used with a two hour shaking time. The digitonin-solubilized enzyme (DS) was prepared as described (Aloni 1983).

Cellulose Entrapment Method—The entrapment method used was described earlier (Kang 1984), with the following modifications: cellulose nitrate tubes, 9/16×3 ¾ in., were used. A 2.6 ml of cushion solution, consisting of TME buffer and 30% glycerol (v/v), were added to the bottom of the tubes. Subsequently, a mixture of 6.8 ml of the solubilized enzyme, 0.2 ml of 100 mM UDP-glucose and 3.4 ml of N-Gx, was layered on the top of cushion solution. The tubes were incubated in a 30° C. water bath for 11 minutes, then were placed on ice for two hours, and centrifuged for 20 minutes in a Beckman SW 40 Ti rotor at 50,000×g. After overnight storage at −80° C., each pellet was resuspended in extraction buffer to 1/30 the original loading volume and homogenized with a Teflon homogenizer. Extraction buffer was prepared with 0.1% detergent in TME buffer containing 20% glycerol. The suspension was centrifuged for 10 minutes at 15,000×g. The supernatant was designated $ES_1$ and the pellet, $EP_1$. The $EP_1$ was resuspended in extraction buffer to the same volume as $ES_1$.

$ES_2$ and $EP_2$ were the resulting supernatant and pellet respectively, from a second entrapment step of $ES_1$. All purified enzymes were stored at −80° C.

Con A-Sepharose Chromatography—Triton X-100 solubilized enzyme preparation, TS, was applied at a flow rate of one column volume/hour to a column (1×10 cm) of Con A-Sepharose 4B previously equilibrated in an "enzyme buffer" of TME, 1 mM $MnCl_2$, 1 mM $CaCl_2$, 20% glycerol and 0.1% Triton X-100. The flow was stopped after the entire sample was applied and allowed to stand for one hour. The column was washed with 25 ml of enzyme buffer, and the bound protein was then eluted with 0.3 M methyl alpha-D-manno-pyranoside in enzyme buffer.

One ml fractions were collected for enzyme assay.

Sephacryl S-300 Chromatography—A column (1.6×85 cm) of Sephacryl S-300 was equilibrated with TME buffer containing 0.1% Triton X-100 and 20% glycerol. The enzyme preparation, TS, was applied and eluted with the same buffer, at a flow rate of 11.0 ml/hr. Fractions of 3 ml were collected and assayed for enzyme activity. The column was calibrated with a series of molecular weight markers (Pharmacia), usually Blue Dextran 2000, thyroglobulin, ferritin, catalase, aldolase and albumin.

Enzyme Assay—Assays contained a final volume of 0.2 ml: 20 μl of 0.5 M Tris-HCl (pH 9.6) containing 50 mM $MgCl_2$ and 5 mM EDTA, 20 μl of 0.1 M $MgCl_2$, 20 μl of 10 MM $CaCl_2$, 25 μl of TME buffer, 25 μl of $H_2O$, 20 μl of crude Gx, and 50 μl of enzyme sample. Incubation was carried out in a 30° C. water bath for either (a) 5 minutes in the final concentration of 20 μM (110 cpm/pmol) UDP-[$^{14}$C] glc or (b) 30 minutes in the final concentration of 1 mM (2.2 cpm/pmol) UDP-[14C]glc. The reaction was stopped with 2 ml of 0.5 M NaOH, and the radioactivity in alkali-insoluble materials was counted after filtration through glass-fiber filters, as described in detail (Bureau and Brown 1987).

Protein Determination—Protein concentrations were determined according to the method of Bradford (1976), using the protein assay kit of Bio-Rad Laboratories. A modification of the Lowry procedure (Markwell 1978) was used only with membrane preparations. In both cases, bovine serum albumin was used as a standard.

Polyacrylamide Gel Electrophoresis—The samples were dissolved in sample buffer containing 2% lithium dodecyl sulfate (LDS), 62.5 mMN Tris-HCl (pH 6.8), 12.5% 2-mercaptoethanol and 20% glycerol with 0.02% bromophenol blue. The incubation was carried out on ice for 1–2 hours, instead of boiling water for 3–5 minutes, because the heating frequently caused the purified protein bands on the gel to smear. Substitution of LDS for sodium dodecyl sulfate resulted in greater resolution for the purified enzyme preparations. Discontinuous LDS/polyacrylamide gel electrophoresis (LDS-PAGE) was performed as described by Laemmli (1970) using 1.5-mm slab gels containing 8% acrylamide. The gels were stained with Coomassie brilliant blue or silver stained (Wray 1981). The molecular mass standards (Biorad) were phosphorylase b (97 kd), bovine serum albumin (66 kd), ovalbumin (42 kd), carbonic anhydrase (31 kd), soybean trypsin inhibitor (21 kd) and hen egg white lysozyme (14 kd).

Photographs of Coomassie blue or silver stained gels were digitized with an IBAS Interactive Image Analysis System (Zeiss, Thornwood, New York). The optical densities of the protein bands were measured by the image edit program.

Identification of Glycoproteins—Approximately 10 μg protein of the $EP_1$ fraction purified from DS was separated by LDS-PAGE in an 8% gel. Subsequently, the periodic acid-Schiff base method using dansyl hydrazine (Eckhardt 1979) and FITC-labeled lectin method (Furlan 1979) were respectively used for glycoprotein identification.

Purification of the Cellulose Synthase—Gel filtration, anion exchange or Con A-Sepharose chromatography were separately combined with the cellulose entrapment step for the purification of the cellulose synthase. However, the recovery of enzyme activity was not high enough and the protein composition of the purified preparation was similar to that when directly purified by the cellulose entrapment (data not shown). Therefore, the cellulose entrapment method was used to purify the cellulose synthase.

The detergent-solubilized enzyme preparation was mixed with the substrate and the enzyme activator. After incubation at 30° C. for 11 minutes, the reaction mixture was centrifuged, and most of the in vitro cellulose was sedimented. Enzyme activity was found primarily in the pellets. Generally, the $ES_1$ contained 20–30% of total protein in the pellets and showed only 10–15% of total enzyme activity. Over 80% of cellulose synthase activities still remained in the $EP_1$. Therefore, the $EP_1$ and $EP_2$ were used as the samples of purified preparations for further characterization.

Cellulose synthase from Acetobacter is very labile. More than half of the activity of solubilized enzyme (such as DS, TS and OGS preparations) was lost after incubation, either at 4° C. for 16 hours, or at 25° C. for one hour. In contrast, entrapped enzyme ($EP_1$) still maintains over half of its original activity after four hours at 25° C., while the activities in the $EP_1$, DS and TS are almost completely lost. It is suggested that the entrapment of the enzyme by the in vitro cellulose product has a stabilizing effect.

As shown in Table III, the purification in the first entrapment step was 42-fold for $EP_1$. The second entrapment showed a 2 to 3-fold purification, in comparison with $EP_1$. The total purification in both steps was about 96-fold. The recovery of cellulose synthase activity was low: 9% for the first entrapment, and 2% for the second entrapment. Therefore, each entrapment step lost 80% of enzyme activity. This may be indicative of why the fold-purification is so low.

TABLE III

Purification of Cellulose Synthase from *Acetobacter xylinum*

| Activity Recovery Step | Total Protein | | Specific Activity nmol/min/mg# | | |
|---|---|---|---|---|---|
| | mg | % | Mean | Best | % |
| Washed membranes | 396* | 100 | 10 | — | 100 |
| Triton extract (TSt) | 65 | 16.4 | 36 | 45 | 59 |
| Cellulose entrapment | | | | | |
| Step 1 (EP$_1$) | 0.85 | 0.2 | 420 | 630 | 9 |
| Step 2 (EP$_2$) | 0.085 | 0.02 | 960 | 1560 | 2 |

*Values were derived from 8 gm (dry weight) of cells.
Mean specific activity represents the values from 5 sets of purifications. Best specific activity represents the value for the individual set of highest specific activity.

Gel Electrophoresis of the Purified Enzyme—The enzyme preparations from each purification step were analyzed by LDS-PAGE. In contrast to the protein bands from TS (FIG. 2, lane 1), very few of the protein bands over 66 kd were observed from TSt (FIG. 2, lane 2). For the purified preparations from the trypsinized washed membranes, two major bands, 93 kd and 83 kd, were found in the gel from the EP$_1$ or EP$_2$ fraction (FIG. 2, lane 4 and 5). Overloading of EP$_2$ in the gel (FIG. 2, lane 5) produced 93 kd and 83 kd bands which accounted for 90% of the total density of stain in the gel lane. These two protein bands also were seen in the EP$_1$ fraction purified from TS, which was prepared from the trypsin-untreated washed membranes (FIG. 2, lane 3).

In addition to two major protein bands, silver staining indicated some minor protein bands in the gel from the TSt-EP$_1$ fraction (FIG. 2, lane 6). For the most purified fraction, TSt-EP$_2$, minor protein bands were still present in the gel (FIG. 2, lane 7 and 8). The 93 and 83 kd polypeptides also accounted for about 90% of the total stain density.

Figure 3:
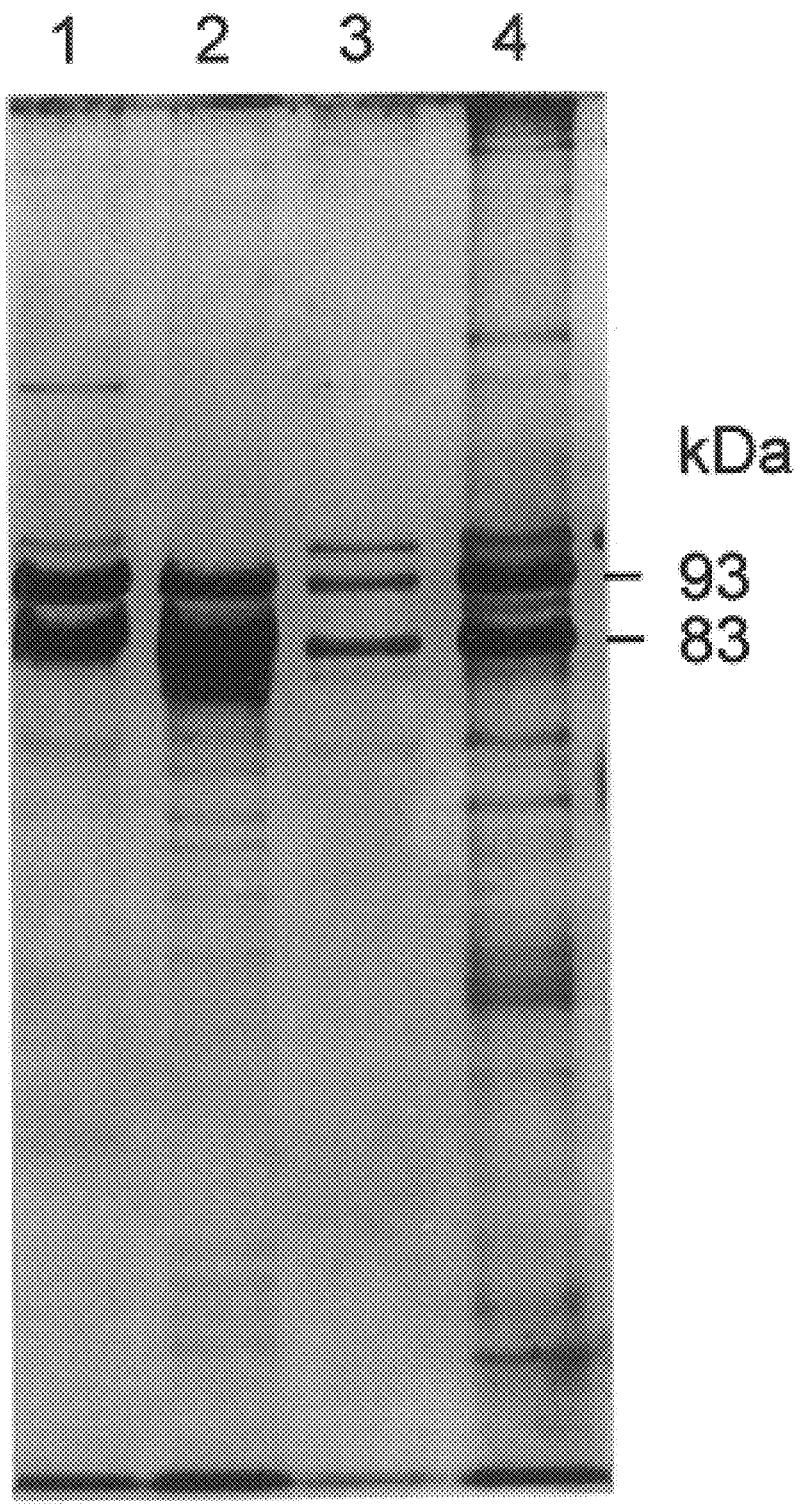
FIG. 3. 8% LDS-PAGE of cellulose synthase in various purified fractions by using two detergents. Lane 1 to lane 4 were stained with Coomassie blue. Lane 1, OGS-$EP_1$ (10 μg), the $EP_1$ purified from the n-octyl glucoside-solubilized enzyme preparation (OGS); lane 2, OGST-$EP_1$ (10 μg), the $EP_1$ purified from OGSt; lane 3, DS-$EP_1$ (5 μg), the $EP_1$ purified from digitonin-solubilized enzyme; lane 4, DS-$EP_1$ (10 μg), the purified preparation from DS, but without 30% glycerol cushion during the entrapment.

By using n-octyl glucoside or digitonin, and following a similar purification procedure, the EP$_1$ fractions also produced 93 kd and 83 kd bands as the major components (FIG. 3, lane 1, 2 and 3). Analysis of the protein composition in the EP$_1$ fraction from the DS with and without a cushion solution (FIG. 3, lane 3 and 4) revealed that more protein contaminants were removed in the presence of the cushion solution.

Without a reducing agent treatment, a 101 kd band appeared instead of the 93 kd band (FIG. 4, lane 1 and 2). Two small protein spots remained at the 93 kd position (FIG. 4, lane 1, arrowheads). The 83 kd band exhibited no change in mobility (FIG. 4, lane 1 and 2).

Trypsin Effect on the Enzymes—Incubation of either the washed membranes or TS with trypsin did not effect enzyme activity after 30 minutes at 25° C. Also, if the trypsin was added to the EP$_1$ fraction from DS, enzyme activity was still maintained after 1 hour at 25° C.; however, only the 83 kd polypeptide was still present in LDS-PAGE while the other polypeptides were degraded after 10 minutes incubation at 25° C. (FIG. 4, lane 3, 4 and 5).

Figure 5:
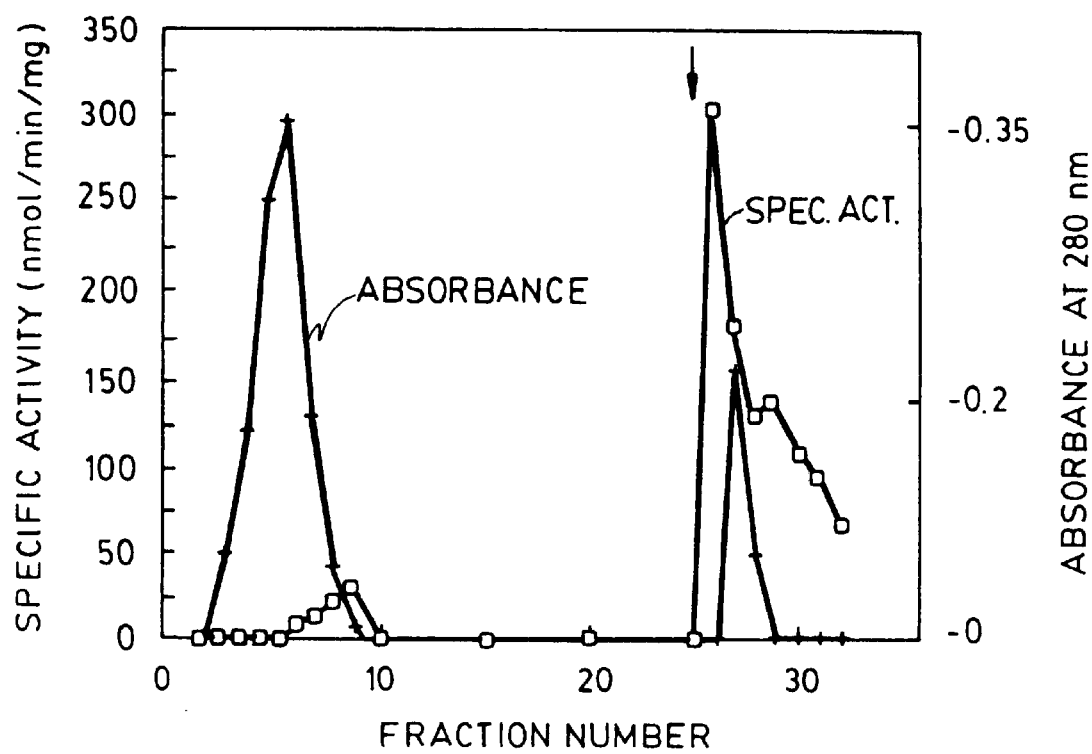
FIG. 5. Elution of cellulose synthase from a Con-A-Sepharose column. A 3 ml sample of the TS fraction was passed through a 7.5-ml Con A-Sepharose column which was then washed with enzyme buffer. The enzyme was eluted with 0.3 M methyl x-D-mannopyranoside in the enzyme buffer (arrow). Fractions of 1 ml were collected.

Characterization of the Glycosylated Protein—The binding of cellulose synthase to Con A-Sepharose was examined. The TS was applied and passed through the column. After washing with buffer, the cellulose synthase was bound with Con A. It could be easily eluted by addition of the enzyme buffer with 0.3 M methyl x-D-mannopyranoside (FIG. 5). More than 90% of the total enzyme activity and about 17% of the protein was recovered, and a 12-fold purification was achieved by this method.

Figure 6:
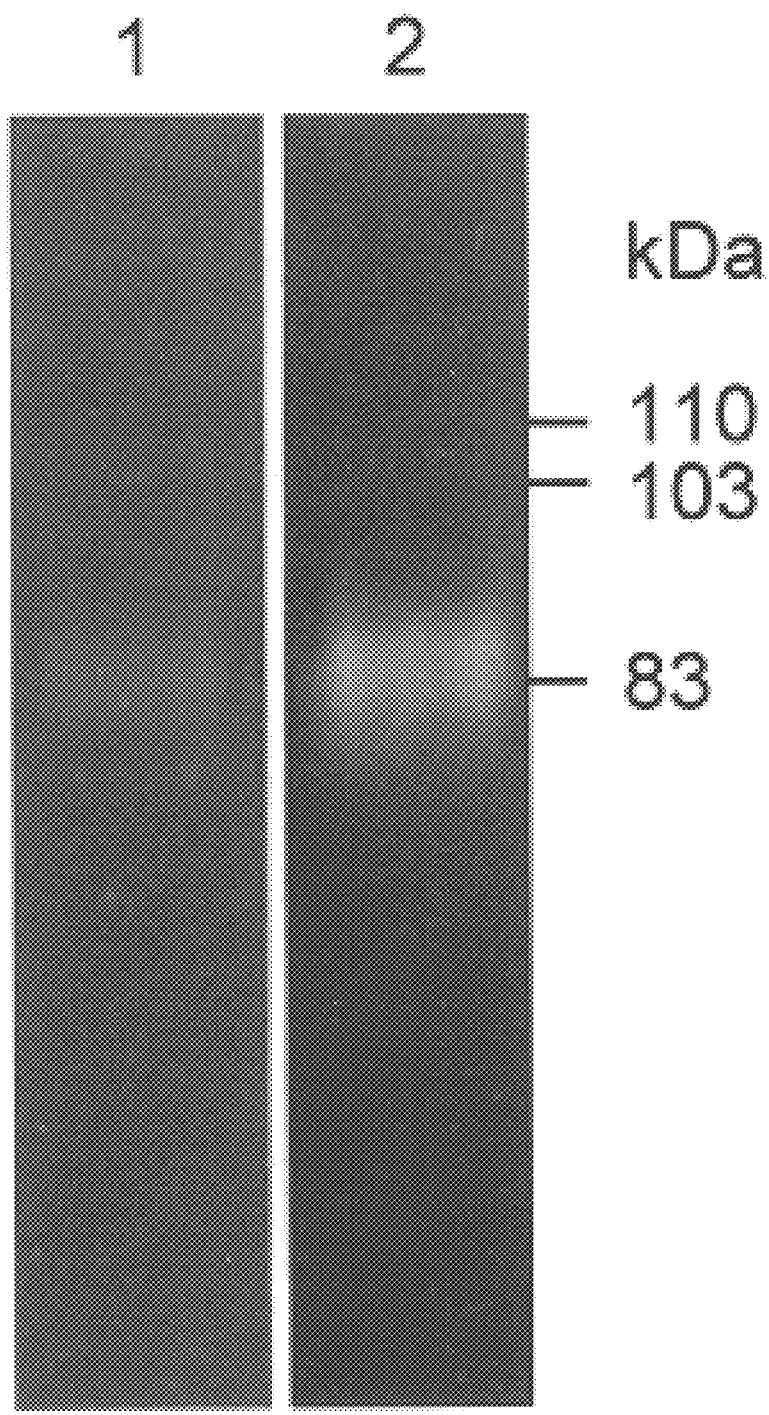
FIG. 6. Photographs of 8% LDS-PAGE without reducing agent, and stained either by the Schiff-periodate method using dansyl hydrazine (lane 1) or with a FITC-Con A (lane 2). Each lane contains 10 μg of the $EP_1$ purified from DS.

When the purified EP$_1$ fraction from DS was separated by LDS-PAGE in the absence of reducing agents, and then stained using FITC-Con A, three bands of 110 kd, 103 kd and 83 kd were found to react with the stain (FIG. 6, lane 2). The 83 kd polypeptide fluoresced much more strongly than the other two bands. This band also fluoresced more strongly when stained with the Schiff-periodate method using dansyl hydrazine (FIG. 6, lane 1).

Figure 7A:
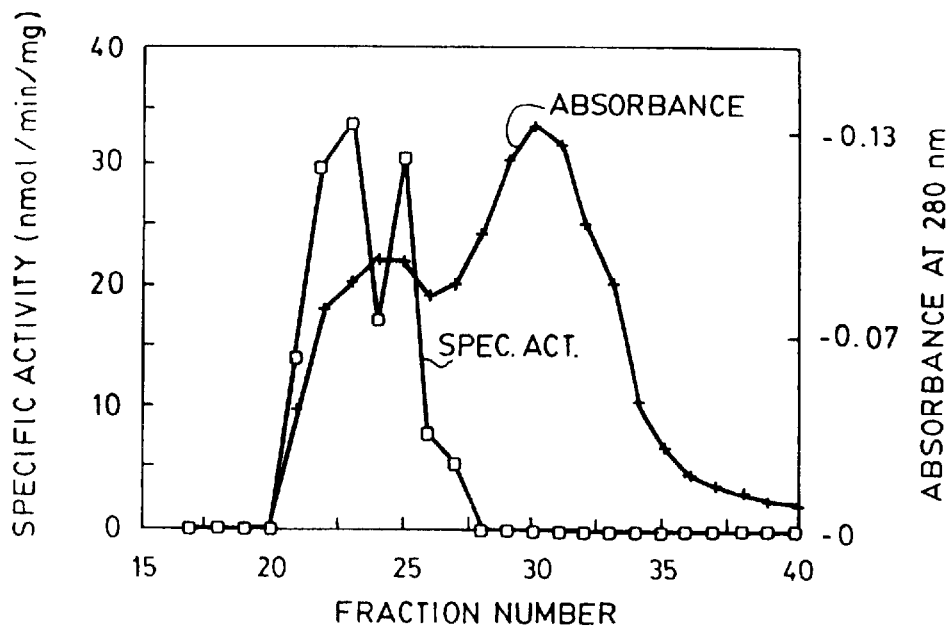
FIG. 7. Gel filtration elution pattern of TS and trypsin-treated TS on Sephacryl S-300. A 3 ml sample was applied. Fractions of 3 ml were collected. (A) elution profile for TS; (b) elution profile for TS which was treated with trypsin (5 μg/ml) at 25° C. for 10 minutes.
Figure 7B:
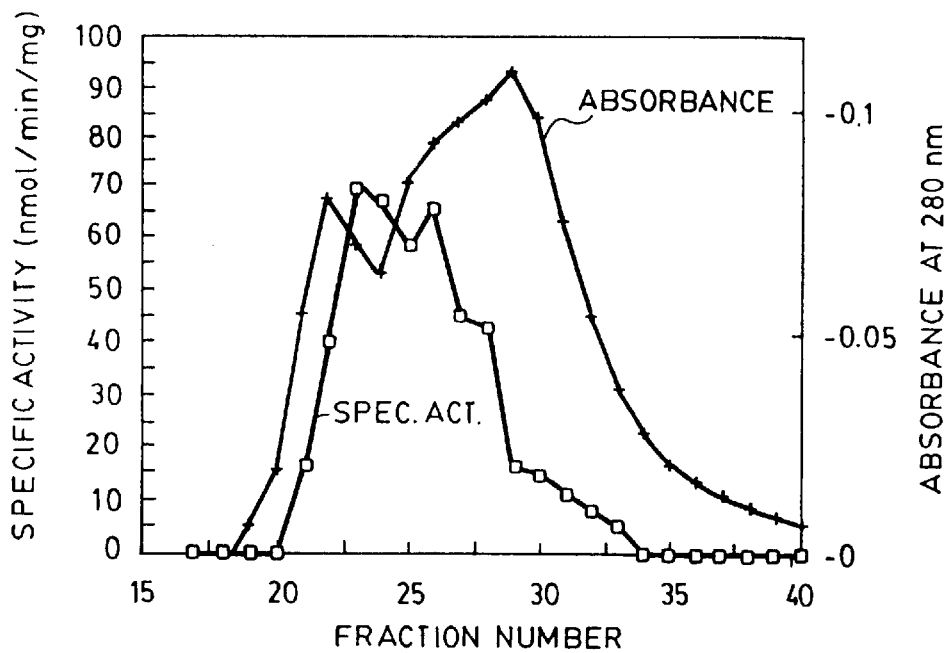

Gel Filtration Chromatography—The Triton-solubilized enzyme preparation, TS, was applied to a Sephacryl S-300 column for determination of the molecular weight of native cellulose synthase. The elution profile of cellulose synthase was determined by measuring the enzyme activity in the column fractions (FIG. 7A). There were two peaks of enzyme activity in the elution profiles. By the use of molecular weight markers as standards of Stokes' radii, the molecular weights of 490 kd and 360 kd for TS were shown to correspond to the two peaks of activity (FIG. 7A). The range was between 650 kd to 300 kd in TS. Therefore, the Stokes' radius of this enzyme was shown to be about 5.5–7.5 nm. After treatment with trypsin at 25° C. for 10 minutes, the TS was applied to the column. The molecular weight range of the cellulose synthase was broadened to between 650 kd and 100 kd, and two peaks were observed to correspond with the molecular weights of 490 kd and 300 kd (FIG. 7B).

After gel filtration, the recovery of cellulose activity was about 60% of total enzyme activity in the originally applied Triton-solubilized preparation (TS). For the trypsin-treated TS, there was no loss of enzyme activity as compared with total activity of the original sample. In addition, the specific activity of the peak fraction from trypsin treated sample was approximately twice as large as the nontreated sample (FIGS. 7A and 7B).

EXAMPLE II

Identification of the Active Subunit of Cellulose Synthase

Photoaffinity labeling—[β-$^{32}$P]5N$_3$UDP-glc was synthesized by a procedure described by Drake et al. (1989). In addition to 20 µl of activator for cellulose synthase, each reaction mixture contained 50 mM Tris-HCl, 10 mM MgCl$_2$, 1 mM CaCl$_2$, 1 mM EDTA, the indicated protein quantity of enzyme sample, and 20 µM of [β-$^{32}$P]5N$_3$UDP-glc (specific activity, 24 mCi/µmol) in a final reaction volume of 50 µl at pH 8.0–8.5. For competition experiments, the competitor, namely UDP-glc, was added at final concentrations of 0, 50, 100, and 300 µM, respectively. For saturation studies, [B-$^{32}$P]5N$_3$UDP-glc was added at final concentrations of 20, 50, 100, 300 and 500 µM, respectively. Reactions were incubated for at 30 degrees centigrade for 30 seconds, followed by short wavelength UV irradiation (254 nm) with a hand-held UV lamp (Model UVSL-58, Ultraviolet Products, Inc.) in open Eppendorf microcentrifuge tubes at a distance of 4 cm for 60 sec. Reactions were terminated by the addition of 0.3 ml of 7% perchloric acid. After 20 minutes, the samples were centrifuged for 3 minutes in an Eppendorf model 5412 centrifuge. The pellet was resuspended in LDS sample buffer for subsequent LDS-PAGE as previously described (Lin and Brown 1989). The Coomassie blue stained gel was dried and autoradiographed. Autoradiography was performed at −80° C. with Kodak X-Omat AR film and a Dupont Cronex intensifying screen. The molecular mass standards (Bio-Rad) were phosphorylase b (97kd), bovine serum albumin (66 kd), ovalbumin (45 kd), and carbonic anhydrase (31 kd).

The quantitation of the autoradiographs was measured by grey value discrimination of a digitized image (recorded on a Kontron/Zeiss IBAS Image Processing System). From this data, the corresponding molecular weight was calculated.

Figure 8:
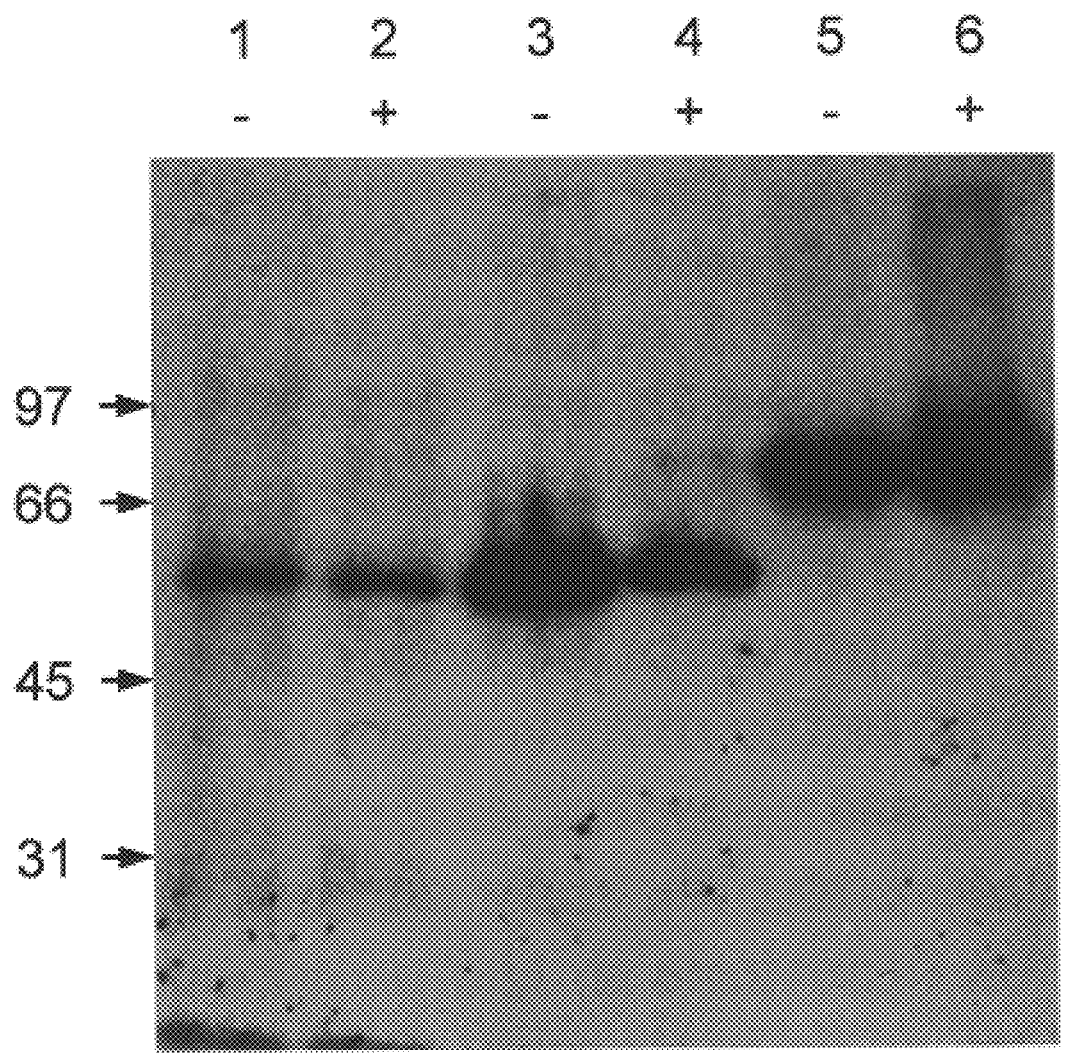
FIG. 8. Photoaffinity labeling of cellulose synthase in various enzyme samples using 20 μM of [β-$^{32}$P]$5N_3$UDP-glc. Samples in lanes 1 and 2 are the membrane fractions, 40 μg of protein per lane. Samples in lanes 3 and 4 are the digitonin-solubilized enzyme (20 μg of protein per lane).

Results of Purification and Photoaffinity Labeling Studies—Two crude enzyme preparations, membranous and digitonin-solubilized forms, and the purified enzyme were tested for their ability to photoincorporate [$\beta$-$^{32}$P]5N$_3$UDP-glc (FIG. 8). With or without the presence of c-di-GMP, there was no labeling of the 83 kd band found in the membrane fraction except for the 57 kd protein band (FIG. 8, lanes 1 and 2). A similar labeling of a 57 kd band was observed in the digitonin-solubilized enzyme preparation (FIG. 8, lanes 3 to 4); however, a faintly labeled band corresponding to the 83 kd polypeptide was seen in the presence of c-di-GMP (FIG. 8, lanes 2 and 4). In the purified preparation, the 83 kd band became intensely labeled (FIG. 8, lane 5) and the photoincorporation increased 45% more in the presence of c-di-GMP (FIG. 8, lane 6).

Figure 9A:
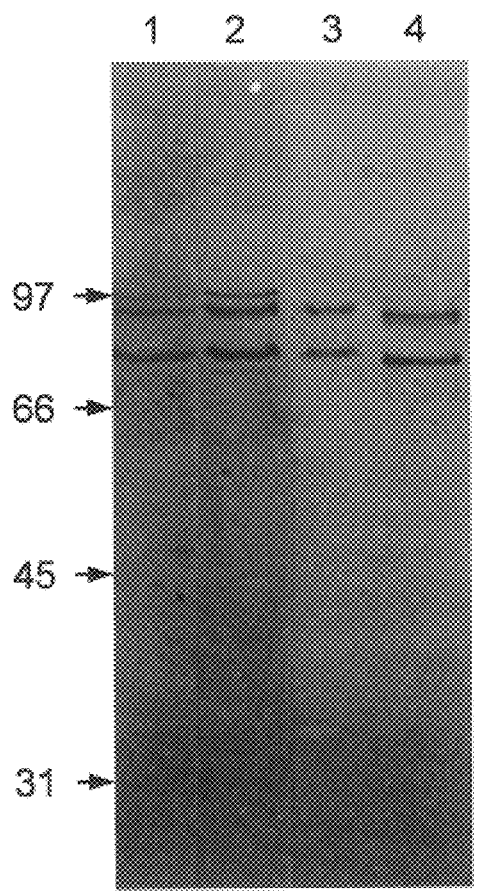
Figure 9B:
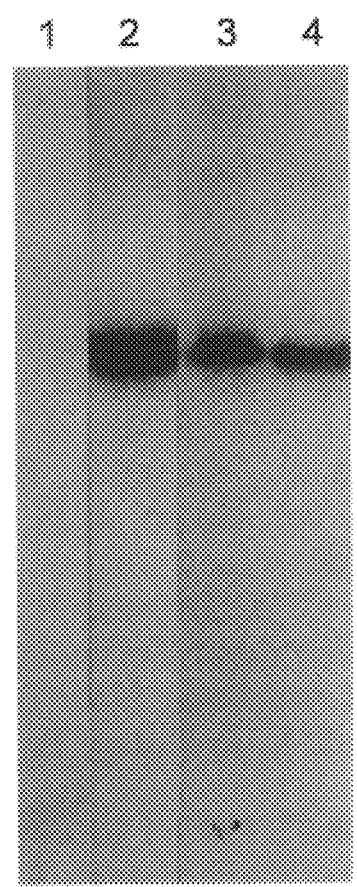

FIG. 9 shows a Coomassie blue stained gel with the corresponding autoradiograph, demonstrating photolabeling of the cellulose synthase in various fractions purified using different detergents. In all cases, the 83 kd protein band was exclusively labeled with [$\beta$-$^{32}$P]5N$_3$UDP-glc (FIG. 9B, lanes 2–4). Control experiments in which the reaction mixtures were not irradiated with UV light (FIGS. 9A and 9B, lane 1) or in which pre-irradiated [$\beta$-$^{32}$P]5N$_3$UDP-glc was used (FIG. 11, lane 1), yielded no labeling of the 83 kd polypeptide or any other polypeptides.

UDP-glucose was known to be the glucosyl donor for cellulose synthase and was selected as a competitor against photoinsertion of [$\beta$-$^{32}$P5N$_3$UDP-glucose. As competitor concentrations increased from 50 to 300 $\mu$M ($\beta$-$^{32}$P] 5N$_3$UDP-glc, the photoinsertion of the probe into the 83 kd polypeptide became reduced (FIG. 10), with a Kd of 82 $\mu$M. These UDP-glc protection studies provided further evidence to validate the specificity of the photoaffinity labeling.

A test of a probe's utility for active site studies has been shown to be the ability to saturate the available binding sites. FIG. 11 shows the saturation of cellulose synthase photolabeling by [$\beta$-$^{32}$P]5N$_3$UDP-glc, with a kd value of 68 $\mu$M. The photoinsertion of the probe into the 83 kd protein band showed that saturation was being obtained with [$\beta$-$^{32}$P] 5N$_3$UDP-glc at concentrations just above 100 $\mu$M. This demonstrated that the photoprobe was binding to a limited number of sites and that nonspecific photoinsertion under these conditions was minimal.

The 57 kd band in the digitonin-extracted enzyme preparations was labeled either by using preirradiated [$\beta$-$^{32}$P] 5N$_3$UDP-glc solutions (FIG. 12, lane 1) or in the absence of photoactivation by UV irradiation (FIG. 12, lane 2), as well as by normal photolysis (FIG. 12, lane 3). These results indicated that the 57 kd protein was not interacting with the photoprobe and that labeling was independent of a photoactive precursor. Furthermore, the labeling of this protein was inhibited in the presence of 500 $\mu$M glc-1-P or glc-6-P (FIG. 12, lanes 4 and 5). It was not inhibited in the presence of glc-1,6-P (FIG. 12, lane 6) which fact was consistent with the properties of phosphoglucomutase [Drake (1989); Ray and Peck (1972)].

There are three major requirements for demonstrating the validity of specific protein binding in photolabeling studies: (a) only a specific protein(s) in an enzyme preparation is photolabeled with the photoprobe; (b) specific photoincorporation at the active site is measured by the ability of the probe to saturate the binding sites and by prevention of photolabeling with the native substrate at appropriate concentrations; and (c) the photolabeling is dependent on the presence of activating light to exclude pseudo-photoaffinity labeling.

The present inventor's results with the purified cellulose synthase preparation met all of these criteria. Thus, these studies confirmed the earlier suggestion (Lin and Brown 1989) and provided solid evidence that the 83 kd polypeptide was the catalytic subunit of the cellulose synthase from *Acetobacter xylinum* strain ATCC 53582. Further strong evidence was that c-di-GMP substantially increased the photoinsertion of [$\beta$-$^{32}$P]5N$_3$UDP-glc with the 83 kd protein. This cyclic nucleotide has been shown to be a true activator for cellulose synthase in *A. xylinum* (Ross 1987). The fibrillar structure and cellulosic nature of in vitro product has been visualized and characterized by electron microscopy (Lin 1985) Using X-ray diffraction analysis, the in vitro product from purified enzyme preparation or membrane fraction (Bureau and Brown 1987) was identified as cellulose II.

In the presence of the cellulose synthase activator, a weakly labeled 83 kd polypeptide in the membrane fraction or the digitonin-solubilized preparation was still detectable (FIG. 8, lanes 2 and 4). In contrast, no detectable labeling was observed when no activator was added (FIG. 8, lanes 1 and 3). Again, this demonstrated that c-di-GMP, the specific activator of cellulose synthase, truly increased the affinity of cellulose synthase for UDP-glc binding and produced a detectable photoactivated labeling of [$^{32}$P]5N$_3$UDP-glc. Two possible reasons for the weak labeling of the 83 kd protein band from these enzyme preparations are as follows: (a) these crude preparations contain trace amounts of the cellulose synthase and therefore would be expected not to label as heavily as the purified enzyme preparation, and *(b) the efficiency of photoinsertion as well as protein concentration affects this labeling.

The 57 kd protein band labeled in the crude membrane fraction and the digitonin-solubilized enzyme preparation is close to the molecular weight previously reported for phosphoglucomutase in the Gram-negative bacteria (Ray and Peck 1972). Though phosphoglucomutase was reported as a soluble enzyme, labeling of a 62–64 kd protein following incubation with [$\beta$-$^{32}$P]5N$_3$UDP-glc has been observed in several membrane preparations (Drake and Haley, unpublished). This labeling has been attributed to trace levels of [$^{32}$P]glc-1-P present in the photoprobe preparations or due to enzymatic hydrolysis of the photoprobe. Whether the 57 kd protein was a membrane-bound isozyme of phosphoglucomutase or was an artifact of the membrane isolation technique was not determined. These experiments confirmed that the 57 kd protein was a phosphoglucomutase.

EXAMPLE III

Cloning and Sequencing of the Gene for the Catalytic Subunit of Cellulose Synthase from Acetobacter Xylinum The purification of cellulose synthase activity and identification of the 83 kd polypeptide by LDS-PAGE to be the catalytic subunit of cellulose synthase provided the present inventors the necessary tools for attempting to clone the DNA encoding this important enzyme. N-terminal amino acid sequencing of the 83 kd polypeptide was carried out as follows. Samples of the highly purified protein were loaded onto gels containing 8% polyacrylamide and electrophoresed according to Lin and Brown (1989). After electrophoresis, the gels were electrophoretically transferred to a polyvinylidene difluoride (PVDF) membrane (Matsudaria 1987). The 83-kd polypeptide band was cut out with a clean razor. The protein from the excised bands were sequenced using an Applied Biosystems model 477A pulse liquid phase sequenator (carried out at the Department of Zoology at the University of Texas at Austin, Tex.).

The amino acid sequence of the 83 kd polypeptide was initially attempted on the purified cellulose synthase of the present invention without being treated with trypsin but this approach resulted in ambiguities at a number of positions during the sequencing and was not used in the design of the oligonucleotide probes. The initial sequence obtained is shown below: (Amino acid residues believed to be ambiguous are italicized.)

Met-Glu-Val-Arg-Gly SEQ ID NO:3/Ser-Leu/unknown-Thr-Gln-Leu-Arg-Leu-Gly-Asn-Thr-Leu-SEQ ID NO:4

While not of use for designing probes, the sequence above was useful in localizing the coding sequence eventually obtained.

The amino acid sequence of the 83 kd polypeptide from purified cellulose synthase was obtained from trypsin-treated membrane preparations as described earlier herein. Specifically, trypsinized membranes were prepared as follows: to 10 ml of washed membranes (protein concentration, 5 mg/ml), 0.2 mg of trypsin was added and gently shaken at 25° C. for 30 minutes. After the addition of 0.2 mg of trypsin inhibitor for 20 minutes, the mixture was centrifuged at! 18,000×g for 20 minutes and washed once in TME.

The trypsinized membranes were resuspended in TME containing 20% glycerol, 0.6% (wt/vol) Triton X-100 to give a final protein concentration of 5.0 mg of membrane protein per ml. After homogenization with a teflon homogenizer, the suspension was gently shaken for one hour, followed by centrifugation at 100,000×g for one hour. The supernatant represents the Triton-solubilized enzyme which is designated "TSt" since the trypsinized membranes are used.

The entrapment method used here was similar to that used previously (Lin and Brown 1989) and is described as follows: cellulose nitrate tubes, 9/16×3 ¾ in., were used. 2.6 ml of cushion solutions, consisting of TME buffer and 30% glycerol (v/v), were added to the bottom of the tubes. Subsequently, a mixture of 6.8 ml of the solubilized trypsin-treated enzyme, 0.2 ml of 100 mM UDP-glucose and 3.4 ml of N-Gx was layered on the top of cushion solution. The tubes were incubated in a 30° C. water bath for 11 minutes then were placed on ice for two hours, and centrifuged for 20 minutes in a Beckman SW 40 Ti rotor at 50,000×g. After overnight storage at −80° C., each pellet was resuspended in extraction buffer to 1/30 the original loading volume and homogenized with a Teflon homogenizer. (Extraction buffer was prepared with 0.1% of detergent in TME buffer containing 20% glycerol). The suspension was centrifuged for 10 minutes at 15,000×g. The supernatant was designated ES1. The EP1 was resuspended in extraction buffer to the same volume as ES1. The purified protein was then used for protein sequencing studies as described above. The resulting trypsinized peptide sequence is shown below:

Ser-Ser-Thr-Gln-Ser-Glu-Ser-Gly-Met-Ser-Gln-Trp SEQ ID NO:5/Leu-Met-Gly-Lys SEQ ID NO:15

As can be readily determined by comparison with the, amino acid sequence of FIG. 1A–FIG. 1L (SEQ ID NO:2), the resulting sequence was fortuitously close to the amino terminal end of the cellulose synthase (amino acid residues 6–20). Once an amino acid sequence was determined with a sufficiently low level of ambiguity, design and synthesis of oligonucleotide (17-mers) from the amino acid sequence data was undertaken for use as probes in DNA-DNA hybridization. For designing oligonucleotide probes from the amino acid sequence, the inventors, selected.a stretch of six amino acids (-Met-Ser-Gln-Trp SEQ ID NO:6/Leu-Met-Gly-) from the trypsin treated 83 kd polypeptide sequence. Eight 17-mer oligonucleotides, each with a unique sequence and having deoxyinosine (I) by the ambiguous position of the serine codons, were synthesized at Operon Technologies, Inc., California. The sequences of the oligonucleotide so constructed are given below: (SEQ ID NOS:7–14 respectively

| 83-1A | 5'-ATGTCICAATGGATGGG-3' |
| 83-1G | 5'-ATGTCICAGTGGATGGG-3' |
| 83-2A | 5'-ATGAGICAATGGATGGG-3' |
| 83-2G | 5'-ATGAGICAGTGGATGGG-3' |
| 83-3A | 5'-ATGTCICAACTGATGGG-3' |
| 83-3G | 5'-ATGTCICAGCTGATGGG-3' |
| 83-4A | 5'-ATGAGICAACTGATGGG-3' |
| 83-4G | 5'-ATGAGICAGCTGATGGG-3' |

Hybridization of the oligonucleotide probes with *A. xylinum* DNA was carried out using the eight oligonucleotides that were thus synthesized. The probe that showed maximum homology with DNA from *A. xylinum* ATCC 53582 was determined by DNA-DNA hybridization. In order to accomplish these studies, total DNA from *A. xylinum* ATCC 53582, *A. xylinum* ATCC 23769, and *E. coil* HB101 (a common strain of *E. coli* used in recombinant DNA experiments) was digested with HindIII and the fragments were separated on an agarose gel. After separation, the fragments were transferred by capillary action to a nylon membrane (GeneScreen; NEN Research Products) according to the procedure of Reed and Mann (1985). The DNA thus transferred was next hybridized with the $^{32}$P-labeled oligonucleotide of the invention using standard procedures. Hybridization was accomplished in a solution with 5×SSC [1×SSC: 0.15M NaCl, 0.015M sodium citrate] at 45° C. for 16–24 hours. The filters were then washed with a solution containing reduced salt concentration. In all cases, the hybridization temperature was 5–7° C. below the dissociation temperature as described by Suggs, et al. (1981) applying the formula Td=2(A+T)+4(G+C).

Oligonucleotide 83-1G showed homology with a single HindIII fragment from *A. xylinum* strains ATCC 53582 and ATCC 23769 under stringent hybridization conditions during which none of the other oligonucleotides exhibited significant homology. To the surprise of the present inventors, all eight oligonucleotides showed hybridization to DNA from *E. coli* HB101 even under stringent conditions (at least 5 HindIII fragments hybridized). This fact prevented the use of standard procedures utilizing recombinant DNA libraries in *E. coli*.

That the 83-1G oligonucleotide was hybridizing with a unique DNA sequence from *A. xylinum* was confirmed by hybridizations with DNA digested with NruI, NarI, SmaI, ClaI, and BalII. In all cases, hybridization was observed with a single fragment of *A. xylinum* DNA.

Once the hybridization studies had been accomplished, cloning of the *A. xylinum* ATCC 53582 DNA fragment homologous to oligonucleotide 83-1G was carried out. The HindIII fragment of *A. xylinum* ATCC 53582 (~9.5 kb) showing homology to 83-1G oligonucleotide was cloned following isolation of *A. xylinum* DNA fragments in that size range from an agarose gel and ligating them to HindIII-cleaved pUC18. DNA fragments were isolated from low melting temperature agarose using the elution tip technique. The fragments were ligated with HindIII cleaved pUC18 using T4 DNA ligase (BRL) at 15° C. for 8 hours. The ligation mixture was transformed into *E. coli* DH5-alpha where colonies carrying recombinant plasmids could be screened for the absence of β-galactosidase activity on medium with X-gal. Very few recombinants were obtained in this strain, possibly due to restriction of *A. xylinum* DNA in the Mcr+ background of this strain, and none of the recombinant plasmids carried the fragment homologous to 83-1G.

Therefore, the ligation mixture was next transformed into *E. coli* HB101 (a recA strain) and transformed colonies were selected on medium containing ampicillin (the selectable marker on pUC18). As pointed out earlier, this strain of *E. coli* made it difficult to screen colonies for recombinant plasmids since there was strong hybridization of the probes with the DNA of these cells. Therefore, plasmid DNA was isolated from pooled collections containing 50 Amp$^r$ colonies each and was analyzed by hybridization with $^{32}$P-labelled 83-1G as probe This screening resulted in the identification of the plasmid pIS532 that carried a HindIII fragment of 9.5 Kb from *A. xylinum* ATCC 53582 homologous to 83-1G.

Sequencing of the *A. xylinum* cellulose synthase catalytic subunit gene was accomplished by first constructing a restriction map of pIS532 using various restriction enzymes. An EcoRI fragment of ~950 bp was identified by hybridization to carry the DNA sequence homologous to 83-1G oligonucleotide. This fragment was cloned into the vector M13mp19 in both orientations and DNA sequencing was performed by the dideoxy chain-termination method. The sequence of the 83-1G oligonucleotide was identified from the sequence obtained and the reading frame was established from the known amino acid sequence of the 83 kd polypeptide. Cloning and sequencing of other fragments from pIS532 was done using M13mp18 and M13mp19 vectors. An analysis of the sequence obtained led to the identification of an open reading frame of approximately 2166 bp coding for a polypeptide of approximately 80 kd. The first 20 amino acids deduced from the DNA sequence matched those obtained for the approximately 83 kd polypeptide corresponding to the purified cellulose synthase subunit.

In summary, the DNA sequence for the catalytic-subunit of cellulose synthase from *A. xylinum* ATCC 53582 was identified using oligonucleotide probes designed from the amino acid sequence of an 83 kd polypeptide that was obtained following purification of the cellulose synthase activity outlined in the examples above. A 9.5 kb HindIII fragment of *A. xylinum* DNA carrying the gene for the cellulose synthase catalytic-subunit was cloned in the vector pUC18. DNA sequencing was performed by the dideoxy chain-termination method following cloning of smaller fragments in M13mp18 and M13mp19. An open reading frame of 2166 bp coding for a polypeptide of 80 kd was identified from the sequencing data in which the first 20 amino acids matched with the N-terminal amino acid sequence of the 83 kd polypeptide.

EXAMPLE IV

Transformation of Cotton With Recombinant Cellulose Synthase

The following example follows the method of Firoozabady (1987). It is proposed that this method may be used in combination with the present invention for transforming cotton with a bacterial recombinant cellulose synthase gene and for obtaining transgenic plants therefrom. As a control for efficacy of the method when applied to cellulose synthase, it is proposed that one may duplicate as closely as possible the method described below and make only those changes as are required from the inherent differences between the bacterial antibiotic resistance gene and the cellulose synthase gene. It will be obvious to those of skill in the art that cotton and other plant species already possess a functional cellulose synthase. It is proposed here that certain utilities and advantages may be realized in improving the target host plant. This may be accomplished by introducing a modified (such as by site-directed mutagenesis or by construction of fusion proteins or by coupling with alternative promoter systems) homologous gene from the same plant species itself back into the same plant's cells. For instance, such a transformation might be accomplished by reintroducing the recombinant cellulose synthase gene derived from cotton by the methods and compositions of the present invention back into cotton cells but which gene was modified by placing the gene under the control of different promoters which then express the recombinant gene. Alternatively, the transformations described here may be accomplished using recombinant cellulose synthase-encoding fragments from sources other than the host cell.

Bacterial Strains and Plasmids

*Escherichia coli* strains MC1061 (Casadaban and Cohen 1980) or K802 (Wood 1966) are employed in the recombinant DNA procedures. MM294(pRK2013) is employed as a plasmid-mobilizing strain (Ruvkun and Ausubel 1981) in triparental matings and 2174 (pPH1J1) as an excluding plasmid donor in marker exchange experiments (Garfinkel 1981). *A. tumefaciens* strains include 15955 (American Type Culture Collection) and LBA4404 (Hoekema 1983). *E. coli* strains are grown in medium (Maniatis 1982) at 37° C. and *A. tumefaciens* strains in YEP (1% yeast extract, 1% peptone, 0.5% NaCl) or Schilperoort's minimal (SM) medium (Klapwijk 1975) with 0.2% sucrose, at 28° C. Antibiotics (mg/i) are used for selecting *E. coli* and include: ampicillin, 50; kanamycin, 25; tetracycline, 10; gentamycin, 10. The latter three antibiotics are typically used for Agrobacterium selection at 25, 10, and 100 mg/l, respectively and streptomycin at 250 mg/l. Plasmids pRK292 (Ditta 1985) and pTJS75 may be obtained from the laboratory of D. Helinski (University of California, San Diego).

Binary Vector System

The details of the construction of the binary vector pH575 are available elsewhere (Sutton 1987). The cloning and recombinant DNA manipulations (Maniatis 1982) of pH575 and its derivatives are all performed using *E. coli* MC1061 as the host strain. Because this strain is resistant to streptomycin, it is unsuitable for use as a donor strain for conjugations into LBA4404. Consequently, the binary vector is transformed into *E. coli* strain K802 for use in triparental matings (Kemp 1983).

For the control experiments, streptomycin- and kanamycin-resistant colonies are purified, and transconjugants are identified by a miniprep procedure adopted from the alkaline lysis procedure (Maniatis 1982). The DNA between the border repeats of the transposon carrying the kanamycin gene is mobilized in trans for integration into plant cells by vir gene functions borne on the co-resident Ti plasmid pAL4404. For the purposes of integrating cellulose synthase into the plant cells, a suitable fragment of the cellulose synthase containing plasmid of Example III above (pIS532) is used to replace the kanamycin gene in pH575 while maintaining the transposable characteristics of the end repeats. This plasmid is designated pH575-cellulose synthase.

Cis Vector System

As a control line of experiments, a cis vector system based on *A. tumefaciens* 15955 is constructed by using the T-region from pH575 to replace the wild-type Ti sequences of pTi15955. The 9530-bp HindIII-partial fragment of pH575 that contains the T-region is re-cloned into the unique HindIII site of pRK292. The resulting plasmid, pH592, is then mated from K802 into a streptomycin-resistant spontaneous mutant of wild type 15955, and transconjugants 15955(pH592) are selected for resistance to streptomycin, kanamycin, and tetracycline on SM medium. Single crossover events, by which a cointegrate plasmid containing pH592 and pTi15955 sequences is generated, is selected on SM by resistance to kanamycin, tetracycline and gentamycin following a second triparental mating in which plasmid pPH1J1 is introduced into 15955(pH592). At least one of these colonies is then subjected to five rounds of cycloserine enrichment as described (Koziel 1983), and at least approximately 2150 single colonies are screened for sensitivity to tetracycline. At least one colony is selected, and the expected structure of the T-DNA, resulting from a second crossover event that eliminates both the pRK292 sequences and $T_L$-DNA bp 1016 to 11207 sequences (Barker 1983), is verified by DNA blot analysis.

A cis vector system based on *A. tumefaciens* 15955 is also constructed by using the T-region from pH575-cellulose synthase to replace the wild-type Ti sequences of pTi15955. The HindIII-partial fragment of pH575-cellulose synthase, or some other suitable fragment that contains the T-region is re-cloned into the unique HindIII site, or some other suitable site, of pRK292. The resulting plasmid is then mated from K802 into a streptomycin-resistant spontaneous mutant of wild type 15955, and transconjugants 15955(pH592-cellulose synthase) are selected for resistance to streptomycin and tetracycline on SM medium. since kanamycin selection is not possible with the cellulose synthase marker, an approach similar to that used in the present invention including reprobing pooled plasmid DNA derived from transconjugants is used (Example III above). Single crossover events, by which a cointegrate plasmid containing pH592-cellulose synthase and pTi15955 sequences are generated, is selected on SM by resistance to tetracycline and gentamycin following a second triparental mating in which plasmid pPH1J1 is introduced into 15955(pH592-cellulose synthase). At least one of these colonies is then subjected to five rounds of cycloserine enrichment as described (Koziel 1983), and at least approximately 2150 single colonies are screened for sensitivity to tetracycline. At least one colony is selected, and the expected structure of the T-DNA, resulting from a second crossover event that eliminates both the pRK292 sequences and $T_L$-DNA bp 1016 to 11207 sequences (Barker 1983), is verified by DNA blot analysis.

Plant Material

Seeds of *G. hirsutum* cv. Coker 201 are surface-sterilized as described (Firoozabady and DeBoer 1986) except that seeds are exposed to bleach for only 8–10 minutes, germinated on MSO medium [hormone-free MS medium (Murashige and Skoog 1962), solidified with 0.2% Gel-rite (Kelko) and incubated as described (Firoozabady and DeBoer 1986).

Transformation and Selection

The bacteria used for inoculation of cotyledon segments are scraped off the agar medium and suspended to a concentration of $\approx 10^8$ ells/ml in a cotton callus initiation liquid medium ($G_2$) containing MS salts (Gibco), 100 mg/l myo-inositol, 0.4 mg/l thiamine HCl, 5 mg/l 6-(y,y-dimethylallylamino)-purine (2iP), 0.1 mg/I cx-naphthaleneacetic acid (NAA) (all from Sigma), 3% (w/v) glucose, pH 5.9. Cotyledon pieces ($\approx 0.5$ cm$^2$ surface area) from sterile 12-day-old seedlings are dipped in the *A. tumefaciens* suspension in petri dishes and gently shaken for a few seconds to ensure contact of all cotyledon edges with the bacterial cultures. The cotyledon pieces are then blotted dry and placed on Whatman No. 1 filter paper on callus initiation medium $G_2$ solidified with 0.2% Gel-rite. Inclusion of the filter paper is not necessary for transformation but is suggested to greatly reduced bacterial overgrowth on plant tissues. Tissues are incubated at 25° C. with a 16-h photoperiod (90 $\mu$E m$^{-2}$ s$^{-1}$).

After three days cocultivaton, cotyledon pieces are transferred to petri plates (without the filter paper) containing the same medium supplemented with 500 mg/I carbenicillin (to control bacterial growth) and, for control experiments, 15–35 mg/I kanamycin sulfate (U.S. Biochemicals). Tissues are incubated at 30° C. with a 16-h photoperiod (op $\mu$E m$^{-2}$ s$^{-1}$). After 3–4 weeks, calli are excised from the original explants, transferred to fresh medium, for control experiments to fresh kanamycin-containing medium, and incubated under lower light intensity (10 $\mu$E m$^{-2}$ s$^{-1}$).

Regeneration of Transgenic Plants

After two to three weeks, calli are placed and maintained on embryogenic medium ($G_2$ with no hormones) and for experimental controls calli are placed under kanamycin selection (25 mg/I). Mature somatic embryos (5–10 mm in length with cotyledons, hypocotyl, and radicle structures) are transferred to GRMgn medium, which is a lower ionic strength medium (Stewart and Hsu 1977) modified by addition of 0.1 mg/l gibberellic acid (Sigma, filter-sterilized), 0.01 mg/l NAA (Sigma) and 0.5% glucose instead of sucrose (with no antibiotics), and incubated at 30° C., 16-h photoperiod (90 $\mu$E m$^{-2}$ s$^{-1}$) to germinate and form plantlets. Plantlets are transferred to GA-7 Magenta cubes (Magenta Corp.) containing GRMgn medium and incubated at 25° C. with a 16-h photoperiod (90 $\mu$E m$^{-2}$ s$^{-1}$). Plants with 3 to 5 leaves are transferred to a commercial peat moss/perlite mixture (Growing Mix No. 2; Fafard Ltd., Canada), maintained in a growth chamber at 25° C. night, 30° C. day, 16-h photoperiod (150 $\mu$E m$^{-2}$ s$^{-1}$) and watered and fertilized as needed. Plants are gradually hardened off, repotted in soil and moved to a greenhouse.

TLC Octopine Assay

To detect octopine in callus or shoot material (as an indication of successful transformation), 10–20 mg fresh weight of tissue is incubated overnight on MSO medium containing 5 mM L-arginine to enhance octopine formation. Tissues are homogenized in microfuge tubes, centrifuged (15000 g. 2 min), and 6 $\mu$l of the supernatants is spotted (2 $\mu$l at a time) on Whatman K-5 silica gel plates (20×20 cm) 1 cm apart. The plate is placed upright in a thin-layer chromatography (TLC) developing tank containing 20 ml of TLC buffer (methanol:2-butanol:0.1 M sodium acetate (pH 4.6), 15;1;4). After one hour, plates are removed, air-dried, sprayed faintly (under a fume hood) with a 1:1 fresh mixture of 10% NaOH in 60% ethanol: 0.04% phenanthrenequinone (Aldrich Chemical Co.) in 100% ethanol, and immediately visualized under UV light (254 nm).

The octopine assay described herein is suggested to be highly reliable. With this method, background artifacts or endogenous opines produced by feeding tissues on arginine (Christou 1986) are not anticipated to be present on the TLC plates at the time of scoring. This is due to the use of TLC buffer in which arginine migrates much more slowly on the plate than opines. It is also important that phenanthrenequinone staining be very light, and that the plate be read immediately after staining under UV light. The intensity of octopine production may be expected to vary, with some plants showing much stronger octopine production than others. In general, the improved sensitivity of the assay is likely to enhance the probability of detecting successful tranformation of cotton callus with recombinant cellulose synthase.

NPT II and Cellulose Synthase Assays: Enzyme-linked Immunoadsorbent Assay (ELISA) and Immunoblot NPT II (ncomycinphosphotransferase II, the enzyme which confers kanamycin resistance) is detected and quantified in cotton extracts by an ELISA assay. The ELISA is constructed with rabbit anti-NPT II immunoglobulin G (IgG), a biotin conjugate of this antibody (Guesdon 1986) and streptavidin alkaline phosphatase conjugate (Bethesda Research Laboratories). Rabbit anti-NPT II antiserum is raised against NPT II purified from *E. coli* containing plasmid pKS4 (Murai 1983). Purified NPT II is used as the standard for calculating NPT II content in tissue extracts. Similarly, rabbit anti-cellulose synthase antiserum is raised against the highly purified cellulose synthase derived from *A. xylinum* or from the other cellulose synthase polypeptides of the present invention.

Plant extracts for ELISA is made by grinding four 5-mm leaf discs in 200 µl of phosphate-buffered saline (127 mM NaCl, 2.6 mM KC1, 8.5 mM $NaH_2PO_4$, 1.1 mM $KH_2PO_4$) containing 0.05% Tween-20, and 1% polyvinyl pyrollidone 40000 (Sigma). Extracts are centrifuged (15000 g, 5 min) and three three-fold dilutions of the sample supernatants are loaded into ELISA plates. Soluble protein concentrations are determined by the Bradford (Bradford 1976) dye-binding assay (Biorad). NPT II levels are expressed as ng NPT II per mg of soluble protein in the extracts, while a similar measurement and analysis is carried out with cellulose synthase.

Cotton leaf extracts for immunoblot analysis are prepared in 4% SDS, 5% 2-mercaptoethanol, 20% glycerol in 0.068 M Tris-HCl (pH 6.8), electrophoresed in 13% polyacrylamide gels (Laemmli 1970), and blotted to nitrocellulose. Blots are processed in either rabbit anti-NPT II IgG (0.1 µg/ml) or rabbit anti-cellulose synthase followed by goat anti-rabbit IgG alkaline phosphatase conjugate (0.2 µg/ml, Kirkegarrd and Perry) by standard procedures (Towbin 1979). Radioimmune precipitation assay buffer (RIPA) (Gilead 1976) is used as the wash buffer and RIPA containing 3% BSA and 1% goat serum is used as the antibody dilution buffer. Blots are developed in nitroblue tetrazolium/ 5-bromo-4-chloro-3-idolyl phosphate (both from Sigma) substrate solution (Balke 1984).

DNA Isolation and Blot Hybridization

DNA is prepared by isolation of nuclei from cotton leaf tissues using a modification of the method of Murray and Kennard (Murray and Kennard 1984). Young leaf tissues are ground in a Bellco glass-glass homogenizer at 4° C. in nuclei buffer (20 mM 1,4-piperazinediethane sulfonic acid (pH 7), 3 mM $MgCl_2$, 0.5 M hexylene glycol, 10 mM orthophenanthroline, 10 mM $NaHSO_3$). Triton X-100 is added to a final concentration of 1% and the mixture centrifuged at 300 g, 4° C. for 5 minutes. The nuclear pellet is resuspended in nuclei buffer and lysed by the addition of an equal volume of 30 mM EDTA, 1.5 M NaCl, and 1% cetyltrimethylammonium bromide in the presence of proteinase K (30 µg/ml, Bethesda Research Laboratories) for 30 minutes at 65° C. DNA is precipitated in 2.5 M $NH_4(Ac$, 50% isopropanol precipitation. Five Ag of DNA is digested with BamHI, electrophoresed through 0.8% agarose, and transferred (Southern 1975) onto nylon membrane (GeneScreen Plus, New England Nuclear). Hybridization is carried out with $^{32}P$-labeled synthetic OCS transcripts and nick-translated NPT II fragments from pH575, as a control, or with the various cellulose synthase probes of the invention. Filters are prehybridized overnight (in heat-sealed bags) at room temperature in 100 mM $NaH_2PO_4$ (pH 7.8), 20 mM $Na_4P_2^{\char`\^}O_7$, 5 mM EDTA, 1 mM orthophenanthroline, 0.1% SDS, 500 µg/ml heparin sulfate, 10% sodium dextran sulfate, and 50 µg/ml each, of heparin sulfate, herring sperm DNA and yeast RNA (Sigma). A portion of the prehybridization solution is removed from the bag, thoroughly mixed with the probe, and then returned to the bag containing the filter. The filter is hybridized for 6–12 h at 65° C. and washed (20 MM $NaH_2PO_4$, 5 mM $Na_4P_2O_7$, I mM EDTA and 0.1% SDS) at 65° C. for 1 h with five buffer changes. Autoradiography is performed on Kodak XAR-5 film with an intensifier screen at –70° C.

Plants whose tissue extracts indicate the presence of cellulose as measured above are selected and tested for enhanced cellulose fiber production. Where applicable, those plants demonstrating improved characteristics will be crossed in order to produce transgenic seed. Any number of indicia may be important to improvement of the plant species thus transformed.

Enchanced or altered cellulose production as a result of the recombinant DNA experiments is deduced by any one or any combination of any of several tests in which the control (non-transformed) and experimental (transformed) plants are compared:

(a) The amount of total cellulose per ovule or per fiber is compared, on a dry weight basis, either before or after alkaline extraction to remove non-cellulosic substances from the cell wall;

(b) The amount of cellulose per fiber as based on a stereology analysis (Zeiss IBAS Image Analysis and Almage Processing System and Image Analysis manual) of cotton fiber cell wall thickness and fiber length or cotton fiber volume is compared;

(c) The polymorph of cellulose present is compared, as determined by x-ray diffraction :Df untreated cotton fibers or electron diffraction oE the cellulose (see procedures described by Alfred D. French in "Cellulose Chemistry and its Applications", Ed. T. P. Nevell and S. H. Zeronian (1985), John Wiley and Sons, New York, Chapter 3, pp 84–111); Also, "El(ectron Diffraction: An Introduction for Biologists", by D. L. Misell and E. B. Brown, Vol. 12, *Practical Method In Electron Microscopy*, Ed. A. M. Glauert (1937), Elsevier, New York, p. 287). Such polymorphs in addiLtion to the. native cellulose I might include but may, not be limited to cellulose II, cellulose III or cellulose IV (note: only cellulose I is expected to be synthesized in vivo in the control plants);

(d) Changes in the average molecular weight of the cellulose are compared, using procedures known to those of skill in the art such as those described by S. B. Ross-Murphy in "Cellulose Chemistry and Its Application", Ed. T. P. Nevell and S. H. Zeronian (1985), John Wiley and Sons, New York, Chapter 8, pp. 202–222;

(e) X-ray or electron diffraction patterns of cellulose are compared as described in (c) above to determine changes in the percent crystalinity of the cellulose;

(f) Changes in total plant size or changes in specific organ size such as cotton boll size, ovule size, leaf size, stem size, root size, and the like as reflected by average cell size within the various tissues and organs of the plant are compared;

(g) Ultrastructural morphology of the cellulose, either in the form of microfibrils, elementary fibrils, sub-fibrils, and the like, are compared using transmission electron microscopy and the typical processing known as "negative staining" or standard heavy metal replication techniques whereby the cellulose is made visj-ble-for analysis and measurement are carried out [Typical procedures are those found in *Experimental High-Resolution Electron Microscopy* (second edition) by John C. H. Spence, p. 427, Oxford University-Press, New York, 1988];

(h) Ultrastructural morphology of the cellulose synthesizing complexes is compared, using the freeze-etch/freeze fracture method, as exemplified in "Replica, Shadowing and Freeze-Etching Techniques" by J. H. M. Willison and A. J. Rowe, Vol. 8 of *Practical Methods In Electron Microscopy* Ed. A. M. Glauert, North-Holland Publishing Co., New York (1980) p. 301. See also, "Cellulose Biogenesis and a Decade of Progess: A Personal Perspective", by R. Malcolm Brown, Jr. (1989) pp. 639–657, *In Cellulose and Wood-Chemistry and Technology*, Ed. C. Schuerch, John Wiley and Sons, New York, p. 1638;

(i) Uptake of cellulose direct dyes and/or fluorescent brightening agents is compared in which case, the patterns of the controls and experimental plants are differentiated, suggesting changes or alterations in cellulose crystalinity, orientation, etc. See Haigler et al. (1980) "Calcofluor White ST Alters the In vivo Assembly of Cellulose Microfibrils", *Science*, 210:903–906; and (j) $^{13}$C, carbon-solid state NMR analysis is carried out to differentiate $I_{alpha}$ and $I_{beta}$ forms of the native cellulose polymorph [Atalla (1984), pp. 881–891, *Structure, Friction and Biosynthesis of Plant Cell* Walls, Ed. Dugger and Bartnicki-Garcia].

The references noted in (a)–(j) above, to the extent that they provide procedural details supplementary to those set forth herein, are specifically incorporated herein by reference.

EXAMPLE V

Probing Plant DNA for Cellulose Synthase Hybridizing to Recombinant Cellulose Synthase Probes The following example is patterned after the method of Dellaporta et al. (1985) and is proposed as general method for isolating and probing plant DNA with which the methods and compositions of the present invention may be combined. It is suggested to be used herein for probing plant DNA for cellulose synthase hybridizing to recombinant cellulose synthase probes.

In general, this protocol is a rapid microscale method for isolation of plant DNA without the use of ultracentrifugation of CsCl gradients. The DNA produced is of moderately high molecular weight and serves as a satisfactory substrate for most restriction endonucleases and is suitable for genomic blot analysis. In addition to the rapidity and convenience of minipreps which permit a large number of samples to be processed in just a few hours, the small amount of tissue required (less than 1.0 gram) allows for molecular analysis of plants at a very young stage. Miniprep DNA yields from leaf tissue of most species tested in the prior art are typically 40–100 ug per gram of tissue, greater than 50 kb in average length, and remarkably uniform from sample to sample.

Several modifications have been applied to the method described herein in order to extend the application of miniprep procedures to other plant species and it is anticipated that one may use similar alterations in order to fit the technique to specific species. The selection of a particular protocol depends to a large degree on the plant species used. However, the procedure reported here is selected to be suitable for most situations.

Procedure

Approximately 1 gm of leaf tissue is quick frozen in liquid nitrogen and ground to a fine powder in a 3" mortar and pestle. The resulting powder is transferred with liquid nitrogen into a 30 ml Oak Ridge tube. It is imperative not to let the tissue thaw once frozen until the buffer is added and not to cap the tubes while nitrogen is evaporating.

Next, 15 ml of Extraction Buffer (EB: 100 mM Tris pH 8, 50 mM EDTA pH 8, 500 mM NaCl, 10 mM mercaptoethanol) is added. For maximum DNA yields, the cells are further broken by grinding the mixture at a low setting (about 3) with a Polytron (Brinkmann Instruments, Inc.). This step is optional and is tested for its efficacy prior to routine use on a specific tissue source.

Approximately 1.0 ml of 20% SDS is added to the tubes and is mixed thoroughly by vigorous shaking. The tubes are then incubated at 65° C. for 10 minutes. A volume of 5.0 ml of 5 M potassium acetate is then added to the tubes and the tubes are shaken vigorously and incubated 0° C. for 20 minutes. This procedure is expected to remove most proteins and polysaccharides as a complex with the insoluble potassium dodecyl sulfate precipitate. Precipitation from 0.3 M sodium acetate using relatively small amounts of isopropanol (about 0.6 volumes) has been reported to separate high molecular weight DNA from polysaccharides (Marmur, 1961). The sodium acetate also yields a tight fibrous precipitate that is easily washed and dried. The DNA dissolves readily if allowed to rehydrate at 4° C. for 1 hour followed by light vortexing.

The tubes are then centrifuged at 25,000×g for 20 minutes. The supernatant is poured through a Miracloth filter (Calbiochem) into a clean 30 ml tube containing 10 ml isopropanol. The resulting solution is mixed and incubated at −20° C. for 30 minutes.

The DNA is pelleted at 20,000×g for 15 minutes. The supernatant is gently decanted and the resulting pellets are lightly dried by inverting the tubes on paper towels for 10 minutes. DNA pellets are redissolved with 0.7 ml of 50 mM Tris, 10 mM EDTA, ph 8 and the-solution is transferred to an Eppendorf tube. These tubes are then centrifuged in a microfuge for 10 minutes to remove insoluble debris.

The supernatant is then transferred to a new Eppendorf tube containing 75 µl 3M sodium acetate and 500 µl isopropanol, mixed well and the clot of DNA is pelleted in a microfuge for 30 seconds. The pellet is then washed with 80% ethanol, dried, and redissolved in 100 µl of 10 mM Tris, 1 mM EDTA, pH 8.

Minipreps can be stored for several months without evidence of degradation and can be restricted with a variety of restriction enzymes and ligated without further purification. It has been found previously that 10.0 µl of miniprep DNA is sufficient for a single 8 mm lane in an agarose gel which is to be used for filter hybridization with single-copy probes. Heat-treated RNAase must be added to the restriction reaction to digest contaminating RNA in each prep. Hence, a typical reaction contains the following:

| Miniprep DNA | 10.0 μl |
|---|---|
| 10X Restriction Buffer | 3.0 μl |
| 0.5 mg/ml RNAase | 2.0 μl |
| EcoRI | 8 units |
| dH2O to 30 μl. | |

Digestion is usually complete after 3 hours at 37° C. Occasionally, minipreps are difficult to digest with certain enzymes. This problem can be overcome by adding 5.0 μl of 0.1 M spermidine to the entire miniprep before digestion (Focus 1982).

Studies by the present inventors and others support the conclusion that many cellulose synthases will be similar enough in primary structure to allow detection by the technique outlined above or by similar techniques. For instance, based on the similarities observed between the terminal synthesizing complexes found at the growing tip of microfibrils of cellulose and similarities in the cellulose organization, it has been possible to construct a phylogenetic pathway for cellulose biogenesis. Where such similarities are adequate, the methods and compositions of the present invention allow the detection and isolation of the similar gene and/or the similar polypeptide.

EXAMPLE VI

Cloning of *A. Xylinum* Cellulose Synthase Gene in Cyanobacterial/*E. Coli* Shuttle Vectors Using the methods and compositions of the present invention, two recombinant plasmids are constructed for transfer of the *A. xylinum* cellulose synthase gene into cyanobacteria. First, a DNA fragment from the plasmid pIS532, carrying the intact cellulose synthase gene along with the promoter sequences from *A. xylinum*, is cloned in the shuttle vector pUC303 (Kuhlemeier et al. 1983). Expression of the cellulose synthase gene is under the control of the *A. xylinum* promoter in this recombinant plasmid. Second, the coding region of cellulose synthase is cloned in the shuttle vector pPL191 (Friedberg 1988) where it is under the control of the operator promoter regions $O_LP_L$, $O_RP_R$, and the temperature-sensitive repressor gene cI857 of bacteriophage lambda. These regulatory sequences are used for monitoring activity of reporter genes in a cyanobacterium background (Friedberg and Seijffers, 1986).

Transformation of Anacystis Nidulans R2-SPc

Anacystis nidulans R2 is the strain of choice for molecular genetic studies in cyanobacteria for which a complete system of gene cloning and analysis has been developed. This strain carries two plasmids of molecular weights 8 Kb and 50 Kb. The 8 Kb plasmid (pUH24) is used for the construction of most shuttle vectors, including pUC303 and pPL191 mentioned above. In order to avoid recombination between the vector and the pUH24 present in *A. nidulans* R2, use is made of the pUH24-cured strain, R2-SPc, for transformation with these vectors.

*A. nidulans* R2-SPc is grown in BG-11 medium (Rippka et al. 1979) at 30° C. with continuous illumination of 250–800 foot candles of fluorescent or mixed tungsten-fluorescent light. Cells from a 30 ml culture are pelleted by centrifugation at 5000 rpm in a Sorvall SS34 rotor for 5 minutes. The pellet is resuspended in 15 ml of 10 mM NaCl and the centrifugation repeated. The pellet is finally resuspended in 3 ml of BG-11 medium ($5\times10^8$ to $1\times10^9$ cells/ml). 300 μl aliquot of cells are transferred to sterile 1.5 ml Eppendorf tubes and 10 ng to 1 μg of recombinant plasmid DNA is added. The tubes are then incubated in the dark at 30° C. for 4–16 hours with gentle agitation, following which 100–150 μl aliquots of each transformation reaction are spread on 100 mm plates containing 40 ml of BG-11 μgar. The plates are incubated under standard illuminated growth conditions for 4–6 hours prior to the addition of the required selective agent. For pUC303 derived plasmid, either chloramphenicol (7.5 μl/ml) or streptomycin (10 μg/ml) is used. Where transformation has been done with pPL191 derived plasmid, kanamycin (25 μg/ml) is used for selecting the transformed cells. The antibiotics are added by lifting the agar slab with an alcohol-flamed spatula and dispensing 400 μl of a 100× concentrated stock underneath. Transformed colonies typically appear within 4–7 days of incubation in the light at 30°. The transformants are purified on BG-11 agar plates containing the suitable antibiotic, and analyzed for their plasmid content.

Expression of *A. Xylinum* Cellulose Synthase Gene in *A. Nidulans*

The expression of cellulose synthase gene from its own promoter (cloned in pUC303) and the bacteriophage lambda promoter (cloned in pPL191) are monitored at the level of RNA synthesis, cellulose synthase polypeptide synthesis, cellulose synthase activity and cellulose biosynthesis. RNA from the transformed cells is isolated essentially as described by Golden et al. (1987) and analyzed by Northern analysis. The synthesis of the cellulose synthase polypeptide in these transformants is determined by western blot analysis using polyclonal antibodies raised against the *A. xylinum* cellulose synthase. Cellulose synthase activity is assayed using $^{14}$C-UDPG as the substrate according to standard procedures herein. Whether the transformed cells synthesize cellulose is determined by isolating the alkali-insoluble material from these cells and analyzing it by X-ray diffraction.

REFERENCES CITED

The following references, to the extent that they provide procedural details supplementary to those set forth herein, are specifically incorporated herein by reference.

1. Aloni, et al., *J. Biol. Chem.* 258; 4419 (1983)
2. Balke, et al., *Anal. Biochem.* 136; 175 (1984)
3. Barker et al., *Plant Molec. Biol.* 2; 335 (1983)
4. Ben-Hayyim and Ohad, *J. Cell. Biol.* 25; 191 (1965)
5. Beyer, et al., *Adv. Enzymol.* 52; 23 (1981)
6. Bradford, *Anal. Biochem.* 72; 248 (1976)
7. Braun, *Biochem Biophys. Acta* 415; 335 (1975)
8. Brown, Jr., et al., *J. Appl. Pol. Sci.: Applied Polymer Symposium* 37; 33 (1983)
9. Bureau and Brown, Jr., *Proc. Natl. Acad. Sci. USA* 84; 6985 (1987)
10. Calvin and Hanawalt, *J. Bact.* 170; 2796 (1988)
11. Christou et al., *Plant Physiol* 82; 218 (1986)
12. Dellaporta et al., *Maize Genetics Cooperation Newsletter* (1983)
13. Dellaporta, et al., In *Molecular Biology of Plants: A Laboratory Course Manual*, Cold Spring Harbor Press, New York (1985)
14. Delmer, *Ann. Rev. Plant Physiol.* 38; 259 (1987)
15. Delmer and Solomon, In *Abstracts of the Fifth Cell Wall Meetings*, #36, (1989)

16. Dennis and Colvin, In *Cellular Ultrastructure of Woody Plants*, W. A. Cote, Ed. Syracuse Univ. Press, Syracuse, N.Y., pp. 199–212 (1965)
17. Dillingham, et al., *Bacteriological Proc*. ASM, p. 67 #A68, (1961)
18. Ditta, et al., *Plasmid* 13; 149 (1985)
19. Drake, et al., *J. Biol. Chem*. 264; 11928 (1989)
20. Easson, et al., *J. Bact*. 169; 4518 (1987)
21. Eckhardt, et al., *Anal. Biochem*. 73; 192 (1979)
22. European Patent Publication O, 223, 417; May 27 (1987)
23. Friedberg, *Methods in Enzymology* 167; 736 (1988)
24. Friedberg and Seijffers, *Mol. Gen. Genet*., 203; 505 (1986)
25. *Focus* 4; 12 (1982)
26. Furlan, et al., *Anal. Biochem*. 96; 208 (1979)
27. Garfinkel, et al., *Cell* 27; 143 (1981)
28. Gasser and Fraley, *Science* 244; 1293 (1989)
29. Gilead et al., *Nature* 264; 263 (1976)
30. Glaser, *J. Biol. Chem*. 232; 627 (1958)
31. Golden et al., *Methods in Enzymology* 153; 215 (1987)
32. Guesdon, et al., *Plant Physiol*. 82; 218 (1986)
33. Haigler, et al., *J. Cell Biol*. 94; 64 (1982)
34. Harding, et al. (1987) *J. Bact*. 169; 2854
35. Herdman, In "*The Biology of Cyanobacteria*", N. G. Carr an d B. A. Whitton, eds., p. 263 (1982)
36. Hess et al., *J. Adv. Enzyme Reg*. 7; 149 (1968)
37. Hoekema, et al., *Nature* 303; 179 (1983)
38. Holland et al., *Biochemistry* 17; 4900 (1978)
39. Kang, et al., *J. Biol. Chem*. 259; 14966 (1984)
40. Kirk-Othmer Concise Encyclopedia of Chemical Technology, M. In *CRC Handbook of Chemistry and Physics*., R. C. Weast, M. J. Astle and W. H. Beyer, Eds. Boca Raton, Fla., pp. C-223 (1984)
41. *The Japan Industrial Journal*, May 15, (1987)
42. *Japanese New York Times*, May 29 (1987)
43. Kemp et al., Owens (ed.), *Genetic Engineering: Application to Agriculture*, Rowman and Allanheld, Toronto (1983) pp. 216–228
44. Klapwijk, et al., *J. Gen. Microbiol*. 91; 177 (1975)
45. Koziel, et al., *J. Molec. Appl. Genet*. 2; 549 (1983)
46. Kuhlemeier, *Plasmid* 10; 156 (1983)
47. Kuhlemeier and van Arkel, *Methods in Enzymology* 153; 199 (1987)
48. Kyte and Doolittle, *J. Molec. Biol*. 157:105 (1982)
49. Laemmli, *Nature* (London) 227; 680 (1970)
50. Lin and Brown, In *Cellulose and Wood—Chemistry and Technology* (Schuerch, C., Ed.), pp. 473–492, Wiley, New York (1989)
51. Lin, et al., *Science*, 230; 822 (1985)
52. Maniatis, et al., *Molecular Cloning: A Laboratory Manual*, Cold Spring Harbor Press, New York (1982)
53. Markwell, et al., *Anal. Biochem* 87; 206 (1978)
54. Matsudaria, *J. Biol. Chem*. 262; 10035 (1987)
55. Mayer, et al., In *Abstracts of the Fifth Cell Wall Meetings*, #38, (1989)
56. Mescher, et al., *J. Bacteriol*. 120; 945 (1974)
57. Mescher and Strominger, *J. Biol. Chem*. 251; 2005 (1976)
58. Messing et al., In *Third Cleveland Symposium on Macromolecules and Recombinant DNA*, ed. A. Walton, Elsevier, Amsterdam (1981)
59. Moescher and Strominger, *Proc. Natl. Acad. Sci. USA* 73; 2687 (1976)
60. Murashige and Skoog, *Physiol. Plant* 15; 473 (1962)
61. Murray and Kennard, *Biochemistry* 23; 4225 (1984)
62. Nanba and Satoh, *Proc. Natl. Acad. Sci. USA* 84; 109 (1987)
63. Porter, *Methods in Enzymology*, 167; 703 (1988)
64. Ray and Peck, In *The Enzymes*, Boyer, P. D., ed., Vol. 6, pp. 407–477, Academic Press, New York (1972)
65. Reed and Mann, *Nuc. Acids Res*. 13; 7207 (1985)
66. Rippka, *J. Gen. Microbiol*. 111; 1 (1979)
67. Roberts, et al., In *Cellulose and Wood:Chemistry and Technology*, C. Schuerch (ed.) pp. 689–704 (1989)
68. Ross, et al., *Carbohydrate Research* 149; 101 (1986)
69. Ross, et al., *Nature* 325; 279 (1987)
70. Ruvkun and Ausubel, *Nature* 289; 85 (1981)
71. Saxena and Brown, In *Cellulose and Wood:Chemistry and Technology*, C. Schuerch (ed.) 537–557 (1989)
72. Schramm and Hestrin, *J. Gen. Microbiol*. 11; 123 (1954)
73. Stewart and Hsu, *Planta* 137:113 (1977)
74. Suggs et al., *ICN-UCLA Symp. Mol. Cell. Biol*. 231; 683 (1981)
75. Tandeau de Marsac et al., *Mol. Gen. Genet*., 209; 396 (1987)
76. Thompson, et al., *Int. J. Biol. Macromol*. 10; 127 (1988)
77. Towbin et al., *Proc. Natl. Acad. Sci. USA* 76; 4350 (1979)
78. Valla, et al., *Mol. Gen. Genet*. 217; 26 (1989)
79. Wasserman, et al., In *Abstracts of the Fifth Cell Wall Meetings*, #35, (1989)
80. Woese, *Microbiol. Rev* 51; 221 (1987)
81. Wood, *J. Mol. Biol*. 16; 118 (1966)
82. Wray, et al., *Anal. Biochem*. 118; 197 (1981)

The present invention has been described in terms of particular embodiments found or proposed by the present inventors to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in the protein structure without affecting in kind or amount of the biological action. All such modifications are intended to be included within the scope of the appended claims.

What is claimed is:

1. A recombinant vector containing a DNA sequence as defined in SEQ ID NO: 1, said DNA sequence encoding an Acetobacter cellulose synthase and being free of Acetobacter DNA sequences not encoding said Acetobacter cellulose synthase.

2. A recombinant vector containing a nucleic acid sequence encoding amino acids 1 to 723 of SEQ ID NO: 2, wherein said nucleic acid sequence is free of nucleic acid sequences not encoding amino acids 1 to 723 of SEQ ID NO: 2.

3. The vector of claim 1, where the cellulose synthase encoding sequence is positioned adjacent to and under the control of an. effective promoter.

4. The vector of claim 3, where the promoter comprises a prokaryotic promoter, the vector being adapted for expression in a prokaryotic host.

5. The vector of claim 3, where the promoter is a eukaryotic promoter, and the vector further includes a polyadenylation signal positioned 3' of the carboxy-terminal amino acid of the cellulose synthase encoding sequence, and within a transcriptional unit for the cellulose synthase.

6. An isolated DNA segment having a nucleic acid sequence encoding Acetobacter cellulose synthase as defined by the nucleic acid sequence of SEQ ID NO: 1 or its complement, wherein said nucleic acid sequence is free of Acetobacter nucleic acid sequences not encoding said Acetobacter cellulose synthase.

7. A recombinant host cell transformed by the vector of claim 1.

8. The recombinant host cell of claim 7 further defined as a eukaryotic host cell.

9. The recombinant host cell of claim 7 further defined as a prokaryotic host cell.

10. The prokaryotic host cell of claim 9 further defined as a cyanobacterium.

11. The recombinant host cell of claim 7 where the Acetobacter cellulose synthase is derived from *Acetobacter xylinum* and the DNA sequence is under transcriptional control of regulatory signals functional in the recombinant host cell to control the expression of the cellulose synthase.

12. The recombinant host cell of claim 8 where the host cell is a plant cell.

13. The recombinant host cell of claim 11, wherein said host cell is from a species of the genus Gossypium.

14. The recombinant host cell of claim 11, wherein said host cell is from an algae.

15. A recombinant vector incorporating an isolated DNA sequence that encodes a cellulose synthase polypeptide comprising, the amino acid sequence of SEQ ID NO:2.

16. The vector of claim 15, wherein the isolated DNA sequence is defined in SEQ ID NO:1.

17. The vector of claim 15, wherein the DNA sequence is positioned adjacent to and under the control of an effective promoter.

18. The vector of claim 17, wherein the promoter is a prokaryotic promoter, the vector being adapted for expression in a prokaryotic host.

19. The vector of claim 17, wherein the promoter is a eukaryotic promoter, and the vector further includes a polyadenylation signal positioned 3' to the DNA sequence that encodes said cellulose synthase.

20. A recombinant vector containing a nucleic acid sequence encoding amino acids 1 to 723 of SEQ ID NO:2.

21. An isolated DNA segment having a nucleic acid sequence that encodes a cellulose synthase polypeptide comprising the amino acid sequence of SEQ ID NO:2.

22. The DNA segment of claim 21, wherein the nucleic acid sequence is defned in SEQ ID NO:1.

23. A recombinant host cell which incorporates an isolated DNA segment or a recombinant vector, the DNA segment or vector encoding a cellulose synthase polypeptide comprising the amino acid sequence of SEQ ID NO:2.

24. The recombinant host cell of claim 23, wherein said DNA segment or vector comprises a nucleic acid sequence as defined: in SEQ ID NO: 1.

25. The recombinant host cell of claim 23, further defined as a eukaryotic host cell.

26. The recombinant host cell of claim 23, further defined as a prokaryotic host cell.

27. The prokaryotic host cell of claim 26, further defined as a cyanobacterium.

28. The recombinant host cell of claim 23, wherein the host cell expresses the cellulose synthase.

29. The recombinant host cell of claim 25, wherein the host cell is a plant cell.

30. The recombinant host cell of claimn 28, wherein said host cell is from a species of the genus Gossypiutn.

31. The recombinant host cell of claim 28, wherein said host cell is from an algae.

* * * * *

UNITED STATES PATENT AND TRADEMARK OFFICE
CERTIFICATE OF CORRECTION

PATENT NO.     : 6,541,238 B1
DATED          : April 1, 2003
INVENTOR(S)    : Inder Mohan Saxena, Fong Chyr Lin and R. Malcolm Brown, Jr.

It is certified that error appears in the above-identified patent and that said Letters Patent is hereby corrected as shown below:

<u>Column 61,</u>
Line 14, after "an", please delete "." therefor.

<u>Column 62,</u>
Line 43, please delete "Gossypiutn" and insert -- Gossypium -- therefor.

Signed and Sealed this

First Day of July, 2003

JAMES E. ROGAN
*Director of the United States Patent and Trademark Office*

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
       (A) LENGTH: 2912 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: CDS
       (B) LOCATION: 636..2804

(xi) SEQUENCE DESCRIPTION: SEQ ID NO:1:

```
CGCTTCCCGC ACATCAGCAT CGTCCATAAG TGAGCGTCCG GTGACAGGGT GTTGCCGATG      60

AATGGAGTCC TGTTCCGAAG CACGCCTCAG CCGCGGGACG TCCGCGTCCC GGCGATCTGA     120

GCTTTTTCTT TCAGGGGATG CGCGACACCC GTGATGAAAA GAAGTTCTTT CCCGTGGCGT     180

CCACGCGATC AGTTCGTTCT AATGTTTCCA GGATGACCAG CATGACCAAG ACAGACACGA     240

ATTCCTCTCA GGCTTCTCGT CCCGGCAGCC CCGTCGCCTC GCCTGATGGG TCGCCCACAA     300

TGGCCGAAGT GTTCATGACG CTGGGTGGTC GTGCGACGGA ACTCCTCAGC CCCCGTCCTT     360

CGCTGCGGGA GGCGCTGTTG CGTCGTCGTG AAAACGAAGA AGAATCCTAA GGCCCTATAT     420

TCAGGCGACC GCCTGTCCCT GTGTCCTGCC TGGTGAAATG GCGGGGGCAG GGGCAGACAC     480

GCTGCACTGG CTCGGCGATC TATTCCGTCT TTGGCCTGGG TGATGTTTCC GCAGCCCAGG     540

CGGGCCCGCT TTGCCCCGAT GTGACCGCAG ATGGTCGGGG TCAGGTTTTT TTTGACGTAA     600

TTTTTCTGTT TTACAGCATT TCGGACGAGT TGTTT ATG CCA GAG GTT CGG TCG       653
                                       Met Pro Glu Val Arg Ser
                                         1               5

TCA ACG CAG TCA GAG TCA GGA ATG TCA CAG TGG ATG GGG AAA ATT CTT      701
Ser Thr Gln Ser Glu Ser Gly Met Ser Gln Trp Met Gly Lys Ile Leu
         10                  15                  20

TCC ATT CGC GGT GCT GGG CTG ACT ATT GGT GTT TTT GGC CTG TGT GCG      749
Ser Ile Arg Gly Ala Gly Leu Thr Ile Gly Val Phe Gly Leu Cys Ala
     25                  30                  35

CTG ATT GCG GCT ACG TCC GTG ACC CTG CCG CCA GAA CAG CAG TTG ATT      797
Leu Ile Ala Ala Thr Ser Val Thr Leu Pro Pro Glu Gln Gln Leu Ile
 40                  45                  50

GTG GCA TTT GTA TGT GTC GTG ATC TTT TTT ATT GTC GGT CAT AAG CCC      845
Val Ala Phe Val Cys Val Val Ile Phe Phe Ile Val Gly His Lys Pro
 55                  60                  65                  70

AGC CGT CGG TCC CAG ATT TTC CTT GAA GTG CTG TCA GGG CTG GTT TCG      893
Ser Arg Arg Ser Gln Ile Phe Leu Glu Val Leu Ser Gly Leu Val Ser
             75                  80                  85

CTG CGC TAT CTG ACA TGG CGC CTG ACG GAA ACG CTT TCA TTC GAT ACA      941
Leu Arg Tyr Leu Thr Trp Arg Leu Thr Glu Thr Leu Ser Phe Asp Thr
             90                  95                 100

TGG TTG CAG GGT CTG CTT GGG ACA ATG CTT CTG GTG GCG GAA CTT TAC      989
Trp Leu Gln Gly Leu Leu Gly Thr Met Leu Leu Val Ala Glu Leu Tyr
        105                 110                 115

GCC CTG ATG ATG CTG TTC CTC AGC TAT TTC CAG ACG ATC GCG CCA TTG     1037
Ala Leu Met Met Leu Phe Leu Ser Tyr Phe Gln Thr Ile Ala Pro Leu
        120                 125                 130
```

```
CAT CGT GCG CCT CTG CCG CTG CCG CCG AAC CCT GAC GAA TGG CCC ACG         1085
His Arg Ala Pro Leu Pro Leu Pro Pro Asn Pro Asp Glu Trp Pro Thr
135                 140                 145                 150

GTC GAT ATC TTC GTC CCG ACC TAC AAC GAA GAA CTG AGC ATT GTC CGC         1133
Val Asp Ile Phe Val Pro Thr Tyr Asn Glu Glu Leu Ser Ile Val Arg
                155                 160                 165

CTG ACG GTG CTG GGA TCA CTG GGG ATT GAC TGG CCA CCG GAA AAG GTG         1181
Leu Thr Val Leu Gly Ser Leu Gly Ile Asp Trp Pro Pro Glu Lys Val
        170                 175                 180

CGG GTT CAT ATC CTT GAT GAC GGT CGT CGT CCT GAA TTC GCC GCC TTT         1229
Arg Val His Ile Leu Asp Asp Gly Arg Arg Pro Glu Phe Ala Ala Phe
            185                 190                 195

GCC GCT GAA TGT GGC GCG AAT TAT ATC GCC CGC CCG ACG AAC GAA CAT         1277
Ala Ala Glu Cys Gly Ala Asn Tyr Ile Ala Arg Pro Thr Asn Glu His
200                 205                 210

GCA AAG GCC GGT AAT CTT AAC TAT GCC ATT GGT CAT ACC GAT GGT GAT         1325
Ala Lys Ala Gly Asn Leu Asn Tyr Ala Ile Gly His Thr Asp Gly Asp
215                 220                 225                 230

TAC ATC CTG ATC TTT GAC TGC GAC CAC GTC CCG ACC CGC GCC TTC CTG         1373
Tyr Ile Leu Ile Phe Asp Cys Asp His Val Pro Thr Arg Ala Phe Leu
                235                 240                 245

CAG TTG ACA ATG GGC TGG ATG GTC GAA GAC CCG AAG ATC GCG CTG ATG         1421
Gln Leu Thr Met Gly Trp Met Val Glu Asp Pro Lys Ile Ala Leu Met
        250                 255                 260

CAG ACC CCG CAT CAC TTC TAT TCC CCC GAC CCG TTC CAG CGG AAC CTG         1469
Gln Thr Pro His His Phe Tyr Ser Pro Asp Pro Phe Gln Arg Asn Leu
            265                 270                 275

TCG GCT GGT TAT CGC ACC CCG CCC GAA GGC AAC CTG TTT TAT GGC GTG         1517
Ser Ala Gly Tyr Arg Thr Pro Pro Glu Gly Asn Leu Phe Tyr Gly Val
280                 285                 290

GTG CAG GAT GGC AAC GAT TTC TGG GAT GCG ACC TTC TTT TGC GGG TCA         1565
Val Gln Asp Gly Asn Asp Phe Trp Asp Ala Thr Phe Phe Cys Gly Ser
295                 300                 305                 310

TGT GCA ATC CTG CGT CGC ACG GCG ATT GAG CAG ATC GGC GGC TTT GCG         1613
Cys Ala Ile Leu Arg Arg Thr Ala Ile Glu Gln Ile Gly Gly Phe Ala
                315                 320                 325

ACC CAG ACC GTG ACC GAA GAC GCG CAT ACC GCA CTC AAG ATG CAG CGT         1661
Thr Gln Thr Val Thr Glu Asp Ala His Thr Ala Leu Lys Met Gln Arg
        330                 335                 340

CTG GGC TGG TCC ACG GCC TAT CTG CGT ATC CCG CTT GCC GGT GGT CTC         1709
Leu Gly Trp Ser Thr Ala Tyr Leu Arg Ile Pro Leu Ala Gly Gly Leu
            345                 350                 355

GCG ACG GAA CGC CTG ATC CTG CAT ATC GGA CAG CGC GTG CGC TGG GCG         1757
Ala Thr Glu Arg Leu Ile Leu His Ile Gly Gln Arg Val Arg Trp Ala
360                 365                 370

CGT GGG ATG CTG CAG ATC TTC CGC ATC GAC AAT CCT CTG TTC GGG CGT         1805
Arg Gly Met Leu Gln Ile Phe Arg Ile Asp Asn Pro Leu Phe Gly Arg
375                 380                 385                 390

GGC CTG TCA TGG GGG CAG CGG CTT TGT TAC CTG TCG GCC ATG ACG TCG         1853
Gly Leu Ser Trp Gly Gln Arg Leu Cys Tyr Leu Ser Ala Met Thr Ser
                395                 400                 405

TTC CTG TTC GCT GTC CCG CGC GTC ATC TTC CTG AGC TCC CCG CTG GCG         1901
Phe Leu Phe Ala Val Pro Arg Val Ile Phe Leu Ser Ser Pro Leu Ala
        410                 415                 420

TTC CTG TTC TTT GGG CAG AAC ATC ATT GCC GCG TCG CCG CTC GCG CTG         1949
Phe Leu Phe Phe Gly Gln Asn Ile Ile Ala Ala Ser Pro Leu Ala Leu
            425                 430                 435

CTG GCC TAT GCC ATC CCG CAC ATG TTC CAC GCC GTC GGC ACG GCG TCG         1997
Leu Ala Tyr Ala Ile Pro His Met Phe His Ala Val Gly Thr Ala Ser
```

```
                    440                 445                 450
AAG ATC AAC AAG GGC TGG CGC TAC TCC TTC TGG AGT GAG GTC TAT GAA        2045
Lys Ile Asn Lys Gly Trp Arg Tyr Ser Phe Trp Ser Glu Val Tyr Glu
455                 460                 465                 470

ACC ACG ATG GCG CTG TTC CTG GTG CGC GTG ACG ATT GTC ACC CTG CTC        2093
Thr Thr Met Ala Leu Phe Leu Val Arg Val Thr Ile Val Thr Leu Leu
                475                 480                 485

AGC CCT TCA CGT GGG AAG TTC AAC GTG ACG GAC AAG GGC GGG TTG CTT        2141
Ser Pro Ser Arg Gly Lys Phe Asn Val Thr Asp Lys Gly Gly Leu Leu
            490                 495                 500

GAA AAA GGT TAT TTC GAC CTT GGC GCT GTC TAC CCG AAC ATC ATC CTT        2189
Glu Lys Gly Tyr Phe Asp Leu Gly Ala Val Tyr Pro Asn Ile Ile Leu
        505                 510                 515

GGC CTG ATC ATG TTC GGC GGC CTG GCG CGT GGT GTC TAT GAA CTG TCT        2237
Gly Leu Ile Met Phe Gly Gly Leu Ala Arg Gly Val Tyr Glu Leu Ser
    520                 525                 530

TTC GGC CAT CTC GAC CAG ATC GCC GAA CGT GCC TAC CTG CTG AAC TCC        2285
Phe Gly His Leu Asp Gln Ile Ala Glu Arg Ala Tyr Leu Leu Asn Ser
535                 540                 545                 550

GCC TGG GCA ATG CTC AGC CTC ATC ATC ATC CTT GCG GCC ATC GCC GTG        2333
Ala Trp Ala Met Leu Ser Leu Ile Ile Ile Leu Ala Ala Ile Ala Val
                555                 560                 565

GGG CGT GAA ACA CAG CAG AAA CGC AAC AGT CAT CGC ATC CCC GCA ACC        2381
Gly Arg Glu Thr Gln Gln Lys Arg Asn Ser His Arg Ile Pro Ala Thr
            570                 575                 580

ATC CCG GTG GAA GTG GCG AAT GCC GAT GGG TCC ATC ATC GTG ACG GGC        2429
Ile Pro Val Glu Val Ala Asn Ala Asp Gly Ser Ile Ile Val Thr Gly
        585                 590                 595

GTG ACC GAG GAC CTG TCC ATG GGT GGG GCC GCG GTG AAG ATG TCA TGG        2477
Val Thr Glu Asp Leu Ser Met Gly Gly Ala Ala Val Lys Met Ser Trp
    600                 605                 610

CCT GCG AAG CTG TCG GGG CCG ACG CCG GTT TAT ATC CGT ACT GTC CTT        2525
Pro Ala Lys Leu Ser Gly Pro Thr Pro Val Tyr Ile Arg Thr Val Leu
615                 620                 625                 630

GAC GGG GAG GAA CTG ATC CTT CCC GCC AGG ATC ATC CGT GCT GGC AAC        2573
Asp Gly Glu Glu Leu Ile Leu Pro Ala Arg Ile Ile Arg Ala Gly Asn
                635                 640                 645

GGA CGG GGG ATT TTC ATC TGG ACG ATT GAT AAC CTG CAG CAG GAA TTC        2621
Gly Arg Gly Ile Phe Ile Trp Thr Ile Asp Asn Leu Gln Gln Glu Phe
            650                 655                 660

TCG GTT ATC CGT CTG GTG TTC GGC CGT GCC GAC GCA TGG GTT GAC TTG        2669
Ser Val Ile Arg Leu Val Phe Gly Arg Ala Asp Ala Trp Val Asp Leu
        665                 670                 675

GGG CAA TTA CAA GGC CGA CCG CCC GCT GCT CAG CCT CAT GGA CAT GGT        2717
Gly Gln Leu Gln Gly Arg Pro Pro Ala Ala Gln Pro His Gly His Gly
    680                 685                 690

TCT CAG CGT CAA GGG CCT GTT CCG TTC AAG TGG CGA TAT CGT CCA TCG        2765
Ser Gln Arg Gln Gly Pro Val Pro Phe Lys Trp Arg Tyr Arg Pro Ser
695                 700                 705                 710

CAG TTC CCC AAC CAA GCC TTT GGC TGG CAA TGC CCT GTC TGACGATACG        2814
Gln Phe Pro Asn Gln Ala Phe Gly Trp Gln Cys Pro Val
                715                 720

AACAACCCGT CACGCAAGGA GCGTGTGCTG AAGGGAACCG TGAAAATGGT TTCGCTTCTG      2874

GCGCTGCTGA CATTTGCTTC CTCGGCACAG GCGGCGTC                              2912

(2) INFORMATION FOR SEQ ID NO:2:

(i) SEQUENCE CHARACTERISTICS:
        (A) LENGTH: 723 amino acids
```

(B) TYPE: amino acid
          (D) TOPOLOGY: linear (ii) MOLECULE TYPE: protein (xi) SEQUENCE DESCRIPTION: SEQ ID NO:2:

Met Pro Glu Val Arg Ser Ser Thr Gln Ser Glu Ser Gly Met Ser Gln
  1               5                  10                  15

Trp Met Gly Lys Ile Leu Ser Ile Arg Gly Ala Gly Leu Thr Ile Gly
                 20                  25                  30

Val Phe Gly Leu Cys Ala Leu Ile Ala Ala Thr Ser Val Thr Leu Pro
             35                  40                  45

Pro Glu Gln Gln Leu Ile Val Ala Phe Val Cys Val Val Ile Phe Phe
         50                  55                  60

Ile Val Gly His Lys Pro Ser Arg Arg Ser Gln Ile Phe Leu Glu Val
 65                  70                  75                  80

Leu Ser Gly Leu Val Ser Leu Arg Tyr Leu Thr Trp Arg Leu Thr Glu
                 85                  90                  95

Thr Leu Ser Phe Asp Thr Trp Leu Gln Gly Leu Leu Gly Thr Met Leu
            100                 105                 110

Leu Val Ala Glu Leu Tyr Ala Leu Met Met Leu Phe Leu Ser Tyr Phe
        115                 120                 125

Gln Thr Ile Ala Pro Leu His Arg Ala Pro Leu Pro Leu Pro Pro Asn
    130                 135                 140

Pro Asp Glu Trp Pro Thr Val Asp Ile Phe Val Pro Thr Tyr Asn Glu
145                 150                 155                 160

Glu Leu Ser Ile Val Arg Leu Thr Val Leu Gly Ser Leu Gly Ile Asp
                165                 170                 175

Trp Pro Pro Glu Lys Val Arg Val His Ile Leu Asp Asp Gly Arg Arg
            180                 185                 190

Pro Glu Phe Ala Ala Phe Ala Glu Cys Gly Ala Asn Tyr Ile Ala
        195                 200                 205

Arg Pro Thr Asn Glu His Ala Lys Ala Gly Asn Leu Asn Tyr Ala Ile
    210                 215                 220

Gly His Thr Asp Gly Asp Tyr Ile Leu Ile Phe Asp Cys Asp His Val
225                 230                 235                 240

Pro Thr Arg Ala Phe Leu Gln Leu Thr Met Gly Trp Met Val Glu Asp
                245                 250                 255

Pro Lys Ile Ala Leu Met Gln Thr Pro His His Phe Tyr Ser Pro Asp
            260                 265                 270

Pro Phe Gln Arg Asn Leu Ser Ala Gly Tyr Arg Thr Pro Pro Glu Gly
        275                 280                 285

Asn Leu Phe Tyr Gly Val Val Gln Asp Gly Asn Asp Phe Trp Asp Ala
    290                 295                 300

Thr Phe Phe Cys Gly Ser Cys Ala Ile Leu Arg Arg Thr Ala Ile Glu
305                 310                 315                 320

Gln Ile Gly Gly Phe Ala Thr Gly Thr Val Thr Glu Asp Ala His Thr
                325                 330                 335

Ala Leu Lys Met Gln Arg Leu Gly Trp Ser Thr Ala Tyr Leu Arg Ile
            340                 345                 350

Pro Leu Ala Gly Gly Leu Ala Thr Glu Arg Leu Ile Leu His Ile Gly
        355                 360                 365

Gln Arg Val Arg Trp Ala Arg Gly Met Leu Gln Ile Phe Arg Ile Asp
    370                 375                 380

-continued

```
Asn Pro Leu Phe Gly Arg Gly Leu Ser Trp Gly Gln Arg Leu Cys Tyr
385                 390                 395                 400

Leu Ser Ala Met Thr Ser Phe Leu Phe Ala Val Pro Arg Val Ile Phe
            405                 410                 415

Leu Ser Ser Pro Leu Ala Phe Leu Phe Phe Gly Gln Asn Ile Ile Ala
                420                 425                 430

Ala Ser Pro Leu Ala Leu Leu Ala Tyr Ala Ile Pro His Met Phe His
            435                 440                 445

Ala Val Gly Thr Ala Ser Lys Ile Asn Lys Gly Trp Arg Tyr Ser Phe
        450                 455                 460

Trp Ser Glu Val Tyr Glu Thr Thr Met Ala Leu Phe Leu Val Arg Val
465                 470                 475                 480

Thr Ile Val Thr Leu Leu Ser Pro Ser Arg Gly Lys Phe Asn Val Thr
                485                 490                 495

Asp Lys Gly Gly Leu Leu Glu Lys Gly Tyr Phe Asp Leu Gly Ala Val
            500                 505                 510

Tyr Pro Asn Ile Ile Leu Gly Leu Ile Met Phe Gly Gly Leu Ala Arg
        515                 520                 525

Gly Val Tyr Glu Leu Ser Phe Gly His Leu Asp Gln Ile Ala Glu Arg
    530                 535                 540

Ala Tyr Leu Leu Asn Ser Ala Trp Ala Met Leu Ser Leu Ile Ile Ile
545                 550                 555                 560

Leu Ala Ala Ile Ala Val Gly Arg Glu Thr Gln Gln Lys Arg Asn Ser
                565                 570                 575

His Arg Ile Pro Ala Thr Ile Pro Val Glu Val Ala Asn Ala Asp Gly
            580                 585                 590

Ser Ile Ile Val Thr Gly Val Thr Glu Asp Leu Ser Met Gly Gly Ala
        595                 600                 605

Ala Val Lys Met Ser Trp Pro Ala Lys Leu Ser Gly Pro Thr Pro Val
    610                 615                 620

Tyr Ile Arg Thr Val Leu Asp Gly Glu Glu Leu Ile Leu Pro Ala Arg
625                 630                 635                 640

Ile Ile Arg Ala Gly Asn Gly Arg Gly Ile Phe Ile Trp Thr Ile Asp
                645                 650                 655

Asn Leu Gln Gln Glu Phe Ser Val Ile Arg Leu Val Phe Gly Arg Ala
            660                 665                 670

Asp Ala Trp Val Asp Leu Gly Gln Leu Gln Gly Arg Pro Pro Ala Ala
        675                 680                 685

Gln Pro His Gly His Gly Ser Gln Arg Gln Gly Pro Val Pro Phe Lys
    690                 695                 700

Trp Arg Tyr Arg Pro Ser Gln Phe Pro Asn Gln Ala Phe Gly Trp Gln
705                 710                 715                 720

Cys Pro Val
```

(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Met Glu Val Arg Gly (2) INFORMATION FOR SEQ ID NO:4:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Thr Gln Leu Arg Leu Gly Asn Thr Leu
1            5

(2) INFORMATION FOR SEQ ID NO:5:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Ser Ser Thr Gln Ser Glu Ser Gly Met Ser Gln Trp
1            5                10

(2) INFORMATION FOR SEQ ID NO:6:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Met Ser Gln Trp
1

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 6
        (D) OTHER INFORMATION: /mod_base= OTHER
            /note= "N = Inosine"

(xi) SEQUENCE DESCRIPTION: SEQ ID NO:7:

ATGTCNCAAT GGATGGG                                        17

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 6
        (D) OTHER INFORMATION: /mod_base= OTHER
            /note= "N = Inosine"

(xi) SEQUENCE DESCRIPTION: SEQ ID NO:8:

ATGTCNCAGT GGATGGG                                                   17

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 6
        (D) OTHER INFORMATION: /mod_base= OTHER
            /note= "N = Inosine"

(xi) SEQUENCE DESCRIPTION: SEQ ID NO:9:

ATGAGNCAAT GGATGGG                                                   17

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 6
        (D) OTHER INFORMATION: /mod_base= OTHER
            /note= "N = Inosine"

(xi) SEQUENCE DESCRIPTION: SEQ ID NO:10:

ATGAGNCAGT GGATGGG                                                   17

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 6
        (D) OTHER INFORMATION: /mod_base= OTHER
            /note= "N = Inosine"

(xi) SEQUENCE DESCRIPTION: SEQ ID NO:11:

ATGTCNCAAC TGATGGG                                                   17

(2) INFORMATION FOR SEQ ID NO:12:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 6
        (D) OTHER INFORMATION: /mod_base= OTHER
            /note= "N = Inosine"

(xi) SEQUENCE DESCRIPTION: SEQ ID NO:12:

ATGTCNCAGC TGATGGG                                                  17

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 6
        (D) OTHER INFORMATION: /mod_base= OTHER
            /note= "N = Inosine"

(xi) SEQUENCE DESCRIPTION: SEQ ID NO:13:

ATGAGNCAAC TGATGGG                                                  17

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 6
        (D) OTHER INFORMATION: /mod_base= OTHER
            /note= "N = Inosine"

(xi) SEQUENCE DESCRIPTION: SEQ ID NO:14:

ATGAGNCAGC TGATGGG                                                  17

(2) INFORMATION FOR SEQ ID NO:15:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Leu Met Gly Lys
1